(12) United States Patent
Li

(10) Patent No.: US 12,011,691 B2
(45) Date of Patent: Jun. 18, 2024

(54) FLUID TREATMENT METHOD, CYCLE TREATMENT DEVICE AND SYSTEM

(71) Applicant: SHANGHAI XINGUANG BIO-PHARMACEUTICAL LTD., Shanghai (CN)

(72) Inventor: Xianghai Li, Shanghai (CN)

(73) Assignee: SHANGHAI XINGUANG BIO-PHARMACEUTICAL LTD., Shanghai (CN)

( * ) Notice: Subject to any disclaimer, the term of this patent is extended or adjusted under 35 U.S.C. 154(b) by 0 days.

(21) Appl. No.: 18/020,623

(22) PCT Filed: Aug. 27, 2020

(86) PCT No.: PCT/CN2020/111885
§ 371 (c)(1),
(2) Date: Feb. 10, 2023

(87) PCT Pub. No.: WO2022/036739
PCT Pub. Date: Feb. 24, 2022

(65) Prior Publication Data
US 2023/0321603 A1 Oct. 12, 2023

(30) Foreign Application Priority Data
Aug. 19, 2020 (CN) .......................... 202010837981.0

(51) Int. Cl.
*B01D 61/02* (2006.01)
*B01D 61/14* (2006.01)

(52) U.S. Cl.
CPC ......... *B01D 61/027* (2013.01); *B01D 61/025* (2013.01); *B01D 61/145* (2013.01); *B01D 61/147* (2013.01)

(58) Field of Classification Search
CPC .. B01D 61/025; B01D 61/027; B01D 61/145; B01D 61/147; A61M 1/3482; A61M 1/3486
See application file for complete search history.

(56) References Cited

U.S. PATENT DOCUMENTS

| 4,508,622 A | 4/1985 | Polaschegg et al. |
| 2013/0102948 A1 | 4/2013 | Reich et al. |

FOREIGN PATENT DOCUMENTS

| CN | 1572332 A | 2/2005 |
| CN | 1845935 A | 10/2006 |
| CN | 1934129 A | 3/2007 |

(Continued)

*Primary Examiner* — Bradley R Spies
(74) *Attorney, Agent, or Firm* — Globle IP Services; Tianhua Gu

(57) ABSTRACT

A fluid treatment method, cycle treatment device, system and medical device are provided, wherein a cycle is formed by allowing a fluid to flow in a pipeline, and the cycle includes a treatment unit to treat the fluid to selectively change structures or concentrations of molecules or combinations thereof in the fluid, thereby avoiding loss of beneficial components; the fluid is treated by at least one cycle, and in any cycle, dynamic equilibrium of the total amount of the fluid in the cycle can be maintained through controlling the rate of adding the to-be-treated fluid into the cycle and the rate of the treated fluid leaving the cycle, so that the cycle is sustainable, and therefore the duration of the fluid treatment method is adjustable and can be determined based on a preset treatment target.

63 Claims, 8 Drawing Sheets

(56) References Cited

FOREIGN PATENT DOCUMENTS

| | | | |
|---|---|---|---|
| CN | 101500701 | A | 8/2009 |
| CN | 102378636 | A | 3/2012 |
| CN | 103732271 | A | 4/2014 |
| CN | 104225698 | A | 12/2014 |
| CN | 105408467 | A | 3/2016 |
| CN | 105916532 | A | 8/2016 |
| CN | 106039448 | A | 10/2016 |
| EP | 0382772 | B1 | 3/1993 |
| WO | 9628198 | A1 | 9/1996 |
| WO | 2020004602 | A1 | 1/2020 |

FLUID TREATMENT METHOD, CYCLE TREATMENT DEVICE AND SYSTEM

CROSS REFERENCE TO RELATED PATENT APPLICATION

The present application is the US national stage of PCT/CN2020/111885 filed on 2020 Aug. 27, which claims the priority of the Chinese patent applications No. 202010837981.0 filed on 2020 Aug. 19, which application is incorporated herein by reference.

FIELD OF TECHNOLOGY

The present disclosure relates to a field of fluid treatment technology, in particular to a fluid treatment method, a cycle treatment device and system, and a medical device.

BACKGROUND

Traditional methods for selective treatment of liquid components include, membrane separation, heating, sedimentation, catalysis, adsorption, chemical reaction, ion exchange, optical treatment, and electrical treatment, etc., however, these treatment methods usually have a poor selectivity or sustainability. For example, the membrane separation cannot achieve an effective and highly selective separation for small molecules; a catalyst is easily mixed into a reaction system in the catalytic reaction; the optical and electrical treatment have poor selectivity; the ion exchange cannot distinguish molecules with same charges; the adsorption is easy to reach a saturation state, and needs high cost; and the chemical reaction is too violent, which is easy to affect other components in the liquid. How to selectively change the concentration of specific molecules or combinations thereof without affecting other components in a system of mixed fluid is still a technical challenge.

For example, in the medical scenario, when a body's metabolic function is insufficient or a body intakes excessively, it will lead to the accumulation of certain molecules in the body, thus inducing metabolic diseases, for example, genetic metabolic defects caused by gene defects, such as phenylketonuria and mucopolysaccharidosis; acute alcoholism caused by excessive alcohol intake; and senile metabolic diseases, such as diabetes, hyperlipidemia and gout. The technology of membrane separation has been used clinically to remove pathogenic factors or toxins in human body, such as hemodialysis, plasma exchange, etc. However, for traditional membrane separation technologies, especially in the medical field, it is inevitable to separate or remove other similar components such as glucose, amino acids, albumin, vitamins, hormones, electrolytes, etc., when dialysis or filtering out certain components from a solution. Meanwhile, waste liquid to be discarded contains the certain harmful components mentioned above and other beneficial components. That is, it is difficult for the traditional membrane separation technology to achieve selective separation or removal of specific components. Since the membrane separation process leads to the loss of beneficial components, there are many limitations in the clinical application of membrane separation to avoid a large amount of loss of beneficial components. For example, the time of the separation process is limited, and the removal effect or clearance rate of membrane separation, such as the concentration of specific components, is also difficult to control. Meanwhile, the continuous production of waste liquid not only causes damage to patients, but also brings the risk of infection and spread of pathogenic microorganisms.

SUMMARY

The present disclosure provides a fluid treatment method, a cycle treatment device and system, and a medical device, which solves problems in the related art such as low efficiency, poor selectivity, impurification of beneficial components causing continuous loss of the beneficial components, and low sustainability.

The first aspect of the present disclosure discloses a fluid treatment method, which includes: introducing a to-be-treated fluid into a pipeline to flow to form a cycle; and discharging a treated fluid from the cycle, and retaining a fluid margin in the cycle; wherein the fluid treatment method is carried out by at least one cycle, the at least one cycle further comprises a treatment unit, the treatment unit is used to perform treatment of a fluid in the cycle to selectively change a composition or concentration of molecules or molecular combinations in the fluid in the cycle, wherein the treatment comprises one or more of a catalytic treatment, a filtration treatment, an adsorption treatment, a heating treatment, an enrichment treatment, a chemical treatment, an optical treatment, and an electrical treatment.

The second aspect of the present disclosure discloses a cycle treatment device, comprising at least one cycle module, wherein a cycle is formed by introducing a to-be-treated fluid into a pipeline of the cycle module, wherein a treated fluid is generated in the cycle and then is discharged from the cycle module, and a fluid margin is retained in the cycle module; wherein the at least one cycle module further comprises a treatment unit, the treatment unit performs treatment on the fluid in the cycle to selectively change structures or concentrations of molecules or molecular combinations in the fluid, wherein the treatment comprises at least one of a catalytic treatment, a filtration treatment, an adsorption treatment, a heating treatment, an enrichment treatment, a chemical treatment, an optical treatment, and an electrical treatment.

The third aspect of the present disclosure discloses a cycle treatment system, which includes the cycle treatment device according to any embodiment provided in the second aspect of the present disclosure; and a pipeline system, including a fluid-introducing pipeline and a fluid-returning pipeline.

The fourth aspect of the present disclosure discloses a medical device, which includes a cycle treatment system according to any embodiment provided in the third aspect of the present disclosure.

The fifth aspect of the present disclosure discloses a non-transitory computer-readable storage medium, which stores at least one program, wherein when the at least one program is executed by a processor, the fluid treatment method described in any embodiment provided in the first aspect of the present disclosure is implemented.

In summary, the fluid treatment method, cycle treatment device, system and medical device of the present disclosure have the following beneficial effects: the cycle is formed by allowing the fluid to flow in the pipeline, and the cycle includes the treatment unit to treat the fluid to selectively change structures or concentrations of molecules or combinations thereof in the fluid; the fluid is treated by at least one of the cycles, and in any of the cycles, dynamic equilibrium of the total amount of fluid in the cycle can be maintained through controlling the rate of adding the to-be-treated fluid into the cycle and the rate of the treated fluid leaving the cycle, so that the cycle is sustainable, and therefore, the duration of the fluid treatment method is adjustable and can be determined based on a preset treatment target.

In general, the treatment unit is provided in the at least one cycle of the present disclosure for cyclic treatment of the fluid. The cyclic treatment enables the process to be more efficient and sufficient. Meanwhile, based on treatment functions of the treatment unit, the fluid treatment method can achieve highly selective removal or generation of target molecules or combinations thereof and avoid continuous loss of beneficial components.

BRIEF DESCRIPTION OF THE DRAWINGS

The specific features of the present disclosure to which this disclosure relates are shown in the appended claims. The features and advantages of the present disclosure can be better understood by referring to the exemplary embodiments and drawings described in detail below. A brief description of the attached drawings is as follows:

DETAILED DESCRIPTION

Figure 1:
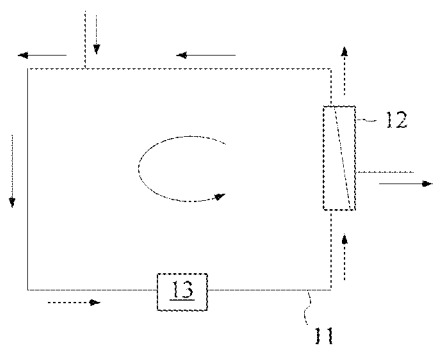
FIG. 1 shows a simplified schematic diagram of a first-type cycle module in an embodiment of the present disclosure.

The specific embodiments of the present disclosure are described below. Those familiar with this technology can easily understand other advantages and effects of the present disclosure from the contents disclosed in this specification.

In the following description, several embodiments of the present disclosure are described by referring to the drawings. It should be understood that other embodiments can also be used to implement the present disclosure, and changes in mechanical composition, structure, electricity and operation can be made without departing from the spirit and scope of the present disclosure. The following detailed description should not be considered as limited, and the scope of the present disclosure is limited only by the claims of the published patent. The terms used herein are only intended to describe specific embodiments and are not intended to limit the present disclosure. Spatial-related terms, such as "up", "down", "left", "right", "below", "under", "beneath", "above", "over", etc., can be used herein to facilitate the description of the relationship between one element or feature and another element or feature shown in the figures.

In some embodiments, although the terms "first", "second", and the like are used herein to describe various elements or parameters, these elements or parameters should not be limited by these terms. These terms are only used to distinguish one element or parameter from another. For example, "a first side" may be referred to as "a second side", and similarly, "a second side" may be referred to as "a first side" without departing from the scope of various described embodiments. "A first side" and "a second side" are both used to describe a location area, but they are not the same location area unless the context clearly indicates otherwise.

Furthermore, as used herein, the singular forms "one", "a/an" and "the" are intended to include the plural form, unless the context indicates otherwise. It should be further understood that the terms "include" and "comprise" indicate the existence of the described features, steps, operations, elements, components, items, categories, and/or groups, but do not exclude the existence, presence, or addition of one or more other features, steps, operations, elements, components, items, categories, and/or groups. The terms "or" and "and/or" as used herein are interpreted to be inclusive or to mean any one or any combination thereof. Therefore, "A, B or C" or "A, B and/or C" means any of the following: "A; B; C; A and B; A and C; B and C; A, B and C". Exceptions to this definition occur only when combinations of components, functions, steps, or operations are inherently mutually exclusive in some ways.

There are certain limitations in traditional methods for selective separation or treatment of specific components of a mixed liquid system. Taking technology of membrane separation as an example, the membrane separation is a process of separation, purification and concentration of different components in a mixture by using a selective separation property of membranes, which is an efficient, energy-saving and environment-friendly separation method. Operations of membrane separation include Normal Flow Filtration (NFF, also known as dead end filtering) and Tangential/Cross Flow Filtration (TFF). During the operation of NFF, a liquid passes through a membrane vertically and molecules are directly filtered out, but the intercepted molecules are easy to form a layer of high-concentration gel and a layer of particle on the membrane surface, which will lead to a sharp drop of the flow rate and flux. During the operation of TFF, the movement direction of the liquid is parallel to (tangential to) the membrane surface. The transmembrane pressure generated by the liquid drives some solutions and small molecules to cross the membrane, and some solutions and molecules with large molecular weights are intercepted. During the whole process, the liquid continuously flows through the surface of the membrane at a certain speed, thereby washing the surface of the membrane and bringing particles deposited on the surface out of the TFF module.

For the technology of membrane separation, it is difficult to avoid producing waste liquid when filtering and separating specific components or molecules for removal. And the waste liquid in medical applications may contain such as glucose, amino acids, albumin, vitamins, hormones, electrolytes, etc. Therefore, the technology of membrane separation in many applications has the defect of consumption of beneficial components in filtration process.

For example, membrane separation based on steric effect is essentially a process of intercepting components with larger molecular weight or particle size in a mixture and allowing components with smaller molecular weight or particle size to pass through, which reflects the directivity of the separation process. To facilitate the description of the method, device and system provided in the present disclosure, membrane separation is divided into the following two modes from the purpose:

Mode A: large molecules are beneficial and small molecules are harmful, that is, small molecules are components that need to be removed.

Mode B: large molecules are harmful and small molecules are beneficial, that is, large molecules are components that need to be removed.

In practical application, mode B is relatively common, and it is also developed for use, such as filtration and sterilization process, water treatment and purification process, etc. Mode B is generally realized by the dead end filtering, however, when there is a high content of molecules with large molecular weight, it is difficult for the membrane to avoid being blocked, therefore, the membrane cannot be used continuously or there is an upper limit on the amount of a to-be-treated liquid. In this case, it is to pretreatment is generally necessary, such as precipitation, distillation or other physical methods. If pretreatment is not possible, such as when the mixture is blood, plasma, etc., the dead end filtering cannot be used.

Mode A is more common in biological applications, such as the concentration and purification of recombinant proteins, hemodialysis and plasma exchange, which are processes to remove harmful or worthless small molecules from the system. Traditional plasma exchange technology, as a typical application of mode A, has the same problem as mode A. Since large molecules are beneficial, tangential flow is generally used to facilitate the intercepted molecules to return to the original system, and to avoid the deposition of these molecules on the membrane surface, which affects the continuity of the treatment process. However, in practical applications, due to poor selectivity, the small molecules cleared in mode A often include beneficial components, such as sugars, amino acids, vitamins, etc., which will cause the loss of a large number of beneficial components when using a physical method of membrane separation for blood treatment, making the treatment process unsustainable.

Here, in the following examples, the present disclosure provides a technical solution for how to selectively and efficiently remove target small molecules from a fluid by using mode A without affecting other molecules or components.

Further, the present disclosure provides embodiments of a catalytic unit with catalytic function selectively treating specific target molecules in s fluid. In these embodiments, mode B can be used to prevent the catalytic unit from leaving a cycle and entering a system, for example, by intercepting the catalytic unit, not only the impact of catalyst entering the system can be avoided, but also the treatment process can be sustainable.

For the application in medical field, for example, when plasma exchange equipment is applied in clinical scenarios such as kidney diseases, cryoglobulinemia, hyperacute or acute antibody-mediated rejection after renal transplantation, plasma exchange can be achieved based on membrane separation to filter out macromolecular pathogenic substances and immune complexes in the blood. In addition to pathogenic factors, there are often beneficial components in the waste liquid to be discarded. Therefore, the treatment process will be accompanied by the loss of beneficial components in the blood, which makes the sustainability of the plasma exchange process low and the clearance efficiency of pathogenic factors limited. In other scenarios, especially for a traditional plasma exchange technology, blood renewal is achieved by separating plasma and delivering plasma substitutes to patients. However, the replacement solution of plasma substitutes may cause allergies to the human body, which limits the feasible use scenarios, and it is usually only used for acute indications such as familial hypercholesterolemia, hyperlipoproteinemia, systemic lupus erythematosus (SLE), myasthenia gravis, rapidly progressive glomerulonephritis, and autoimmune diseases. Besides, when plasma is separated and extracted for replacement, there is also a problem that beneficial components other than plasma, such as platelets, are extracted. This method still has the defect of loss of beneficial components, thus making the sustainability of the method low.

For traditional technology of double filtration plasmapheresis (DFPP for short), the plasma is usually filtered twice in a corresponding filtering system, where a technology for separating plasma (i.e., separating plasma, red blood cells, platelets and hemameba from the blood) and a technology for separating plasma component (i.e., separating specific components from the plasma) are adopted to form a two-stage filtration to remove macromolecular pathogenic factors such as autoantibodies, immunoglobulins, immune complexes, inflammatory molecules or low-density lipoproteins in the separation of plasma components. Therefore, DFPP is usually used for severe diseases (such as myasthenia gravis, Guillain Barre syndrome, systemic lupus erythematosus (SLE), rheumatoid arthritis, hyperlipidemia severe acute pancreatitis, sepsis) with macromolecules as pathogenic factors, but DFPP is not suitable for the removal of small and medium molecular pathogenic substances combined with albumin, and not suitable for the removal of free small and medium molecular solutes.

DFPP is a combination of mode A+mode B. Usually, the molecules intercepted between the two filters corresponding to two pore sizes of membrane or molecular weight cutoffs are the target molecules to be removed. In DFPP, the tangential/cross flow filtration can be used to solve the problems in mode B, and can effectively avoid the problem of blocking caused by dead end filtering. However, in practical applications of DFPP, when removing harmful macromolecules, beneficial small molecules will also be removed together. In the process of separation, a plasma abandonment rate is generally 10%-30%, and the plasma abandonment rate refers to the ratio of the transport rate of the plasma abandonment pump to the plasma separation pump; more specifically, in the process of double filtration plasmapheresis, the flow rate of discarded plasma is usually 2.5-6 ml/min, which means that patients will lose more than 300-720 mL of plasma after receiving treatment for 2 hours even if the double filtration plasmapheresis is used. That is, if DFPP is used to exchange the plasma of patients, a certain volume of plasma to be discarded, i.e. waste liquid, will inevitably be produced after a period of time. In fact, the waste liquid contains beneficial components from human body. If a replacement liquid, such as exogenous plasma, is used for delivering to patients, it may cause allergic reactions in human body. Due to the continuous loss of beneficial components in the traditional DFPP technology, this treatment method has significant defects and risks, and can only be used in some emergencies and ICUs. Therefore, in clinical treatment, it is necessary to limit the treatment time (generally limited to 2-5 h) and application scenarios of DFPP. Due to the limitation of treatment time, DFPP also has a limited removal effect.

For another example, CN103263704A has disclosed a adsorption filtration purification system, where a certain amount of plasma is separated from the human blood, and then the plasma is introduced into a purification unit to perform several times of adsorption processes to regenerate part of the discarded plasma and reduce the demand of fresh plasma in plasma exchange. However, during the absorption process of plasma, the filtrate produced by the high-throughput filter used in the purification unit is a waste liquid. Therefore, although a certain proportion of regenerated plasma is obtained in the plasma regeneration process, waste liquid can still be generated. The problem of waste liquid and the continuous loss of beneficial components that may be caused by the waste liquid still exist in CN103263704A, and the filtrate is supplemented by replacement liquid, resulting in the risk of allergies caused by foreign substances in the aforementioned DFPP. Further, the high-throughput filter in the adsorption filtration purification system is only applicable to the treatment of small molecule plasma toxins, and a multiple filtering is carried out to improve the filtering effect on small molecule toxins to regenerate a certain proportion of plasma in waste plasma. However, the adsorption filtration purification system cannot remove the pathogenic factors with large molecular weight in blood, so that the use scenarios are limited, and it is difficult to collect or remove different components in blood. The present disclosure provides a fluid treatment method and a cycle treatment device, system and a medical device, which can be used in various scenarios, including medical scenes, and to treat various fluids, thereby directionally removing specific molecules or components or changing the structure or concentration of specific molecules or components in the fluid based on preset targets. Meanwhile, the present disclosure separates harmful components through membrane separation under mode A, and processes target molecules through catalytic units; besides, through membrane separation, the catalytic unit is intercepted in a cycle under mode B, thus forming a cyclic treatment. The fluid treatment method and fluid treatment device of the present disclosure can be used to achieve effective and sustainable control of fluid composition.

The first aspect of the present disclosure provides a fluid treatment method, which includes: introducing a to-be-treated fluid into a pipeline for flow to form a cycle; and discharging a treated fluid from the cycle, and retaining a fluid margin in the cycle; where the fluid treatment method is carried out by at least one cycle, the at least one cycle further includes a treatment unit, which is used to perform treatment of a fluid in the cycle to selectively change the structure or concentration of molecules or combinations thereof in the fluid in the cycle, where the treatment includes one or more of a catalytic treatment, a filtration treatment, an adsorption treatment, a heating treatment, an enrichment treatment, a chemical treatment, an optical treatment, and an electrical treatment.

The fluid contains a target substance. In some embodiments provided by the present disclosure, the fluid includes, but is not limited to, one or more of blood, plasma, serum, body fluid, tissue fluid, cleaning fluid, dialysate, recombinant protein solution, cell culture medium, microbial culture medium, pharmaceutical and medical water, liquid medicine, fluid food, animal and plant extract, natural water, industrial wastewater, and recycled water. In some embodiments, the fluid can also be a component obtained after a fluid, such as blood and plasma, has been treated such as filtration. In other embodiments, the fluid may also be a mixture of gas, such as a gas mixture containing methane.

The fluid treatment method of the present disclosure can be applied to different types of fluid treatment, as long as a treatment unit with corresponding selectivity can be set based on the fluid composition. It should be understood that the fluid includes at least two components, so that a selective change of the structure or concentration of molecules or combinations thereof in the fluid, performed by the treatment unit, can be achieved. In each embodiment provided in the present disclosure, the selective change of the structure or concentration of molecules or combinations thereof in the fluid means, the treatment unit only changes the structure or concentration of some components in the fluid of the mixture system, without affecting other components.

In particular, in some embodiments, the components in the fluid change dynamically over time, where the change of the fluid includes: change in the number of substance categories in the fluid, such as an increase or decrease, or/and change in the concentration or total amount of at least one substance in the fluid.

In some embodiments, based on the specific composition of the fluid, the material of the pipeline can be a special material corresponding to the fluid, for example, part of the pipeline in the cycle can be set as a dedicated pipeline for blood, a dedicated pipeline for peristaltic pump, a dedicated pipeline for corrosive liquid, a pipeline with high biocompatibility, etc.; When the fluid treatment method is applied in the medical scene, taking the pipeline such as a blood delivery pipeline or a liquid medicine delivery pipeline as an example, the pipeline materials include, but are not limited to, soft polyvinyl chloride, high-performance thermoplastic polyolefin elastomer (TPE), nano biomedical materials, and resin materials.

The treatment method may be realized by one cycle, or by two or more cycles jointly. The fluid treatment method of the present disclosure can introduces the to-be-treated fluid into one cycle, and the treated fluid will be introduced into another cycle after leaving the cycle, the different cycles can be regarded as forming a series connection. Alternatively, the fluid can be introduced into different cycles after being divided for treatment and then collected after treatment, the different cycles in this case can be regarded as forming a parallel connection.

It should be noted that in the embodiment provided by this disclosure, the to-be-treated fluid refers to the fluid introduced from an inlet of a specific cycle, that is, the term of "to-be-treated fluid" is a relative concept, and is not limited to be an original fluid without any treatment. For example, when the fluid treatment method is realized through a plurality of cycles, the fluid drawn from one cycle is introduced into a subsequent cycle for treatment, where the fluid drawn from one cycle can be used as the to-be-treated fluid of the subsequent cycle.

In the embodiment provided in the present disclosure, all the fluids existing in the pipeline of the cycle can be regarded as the fluid margin, that is, the fluid margin is defined based on the spatial location of the fluid, when the fluid in the pipeline leaves the cycle, it is no longer called the fluid margin. Correspondingly, the fluid margin may include a to-be-treated fluid and a treated fluid.

The operation performed by the treatment unit includes at least one of catalysis, filtration, adsorption, heating, enrichment, chemical treatment, optical treatment, and electrical treatment. The treatment unit has functions including changing the concentration of any component or molecular combination in the to-be-treated fluid, or changing the structure of any molecule, changing the charged state, and changing the physical structure. In a mixture system, for example, the reaction rate of specific molecules therein can be changed by catalysis to change the structure and concentration of molecules or combinations thereof in the mixture system; for another example, a specific component in the mixture system can be directionally adsorbed through adsorption, thereby realizing the change of concentration of the specific component in the system; for another example, a specific component in the mixture system can be decomposed by heating under specific conditions, such as a certain temperature range; for another example, the technology of membrane separation is used to intercept specific components in the cycle to form an effect of enrichment, thereby achieving selective changes in the concentration of specific molecules or combinations thereof in the mixed system.

Here, the treatment unit is a control unit of a hardware module, a piece of equipment and a device arranged in the pipeline or other devices electrically connected to the pipeline. The treatment unit can be used to form an element or a device in the cycle, or control the elements or devices in the cycle to achieve the fluid treatment function. In some embodiments, the treatment unit may be controlled by a computer device (which may be a personal computer, a server, or a network device, etc.), or the treatment unit may be manually controlled.

For example, the treatment unit may be a filtering device, an adsorption device, a heating device connected to the pipeline, or a sampling device that can be used to add a catalyst to the pipeline, a control device for controlling the contact of the catalyst and fluid, a temperature control device for controlling the activity of catalyst, a reaction substrate adding device that adding substrate corresponds to the catalyst, etc.

In a specific embodiment, the to-be-treated fluid is introduced into the pipeline for flow to form a cycle, where the treated fluid in the cycle is discharged from the cycle, and the fluid margin is retained in the cycle. Generally, the to-be-treated fluid is introduced into the cycle through the inlet of the cycle, and the treated fluid is discharged from the cycle through the outlet. The to-be-treated fluid can be continuously supplemented to the cycle. It should be understood that in this case, components of the fluid margin in the cycle are kept updated, and the treatment unit can selectively and continuously treat the fluid margin in the cycle correspondingly.

In the embodiments provided in the present disclosure, the term "cycle" can be used to indicate the state in which the fluid flows in the pipeline to form a cycle; meanwhile, the term "cycle" can also be used to include pipelines; units formed by hardware or structure which is formed by equipment connected or associated in the pipelines, such as treatment units, driving devices, etc.; fluid in the aforementioned hardware or structure, such as the fluid in the pipelines; as well as reactants added to the pipelines, etc.

It should be noted that the to-be-treated fluid is a mixture system, and the treated fluid in this disclosure is a mixture system after being treated by the treatment unit, and is not limited to specific molecules or combination of molecules directionally treated by the treatment unit. In different scenarios, the specific composition of the mixture system and the treatment process performed by the treatment unit may be different from each other, accordingly, the treated fluid may be a specific molecule or combination of molecules in the to-be-treated fluid, or a product generated by the reaction of the specific molecule or combination of molecules, or a mixture of at least one or more of other untreated components in the to-be-treated fluid.

The fluid treatment method of the present disclosure can selectively change the structure or concentration of molecules or molecular combinations in the fluid through the treatment unit. Meanwhile, a controllable environment for the contact of the treatment unit and the to-be-treated fluid is constructed by forming the cycle. Thus, the present disclosure cannot only achieve highly selective treatment of the mixture system, but also adjust the efficiency, effect, and the duration of the treatment method.

When treating a fluid flowing in a section of the pipeline, the traditional treatment process is often inefficient and cannot realize a treatment completely, or the treatment process is affected or limited by the interaction of flow rate and the duration of treatment.

In a pipeline where the fluid flows one-way traditionally, for example, to keep the pipeline full of fluid, the velocity of introducing fluid into the pipeline is equal to the velocity of discharging fluid from the pipeline. In this way, the flow velocity inside the pipeline would be affected by the velocity of introducing fluid or the velocity of discharging fluid that is, the flow velocity inside the pipeline is determined by the velocity of introducing fluid and the internal cavity structure of the pipeline, indicating that in the actual scene, the flow velocity inside the pipeline is a dependent variable of the velocity of introducing fluid. And the contact time or action time of the fluid in the pipeline and other equipment or components associated with the pipeline is also affected by the velocity of introducing fluid, due to a one-time contact or one-time action between the pipeline and other equipment or components associated with the pipeline.

According to the fluid treatment method of the present disclosure, by making the to-be-treated fluid form a cycle in the pipeline, and allowing the continuous introduction of the to-be-treated fluid and the continuous discharge of the treated fluid of the cycle, the treatment process is sustainable. In this way, the duration of the treatment can be determined based on the preset treatment target.

Besides, based on a dynamic environment formed by the cycle, components of the fluid in the cycle change dynamically, the supplemented to-be-treated fluid can be treated continuously by the treatment unit during the treatment process, thereby the efficiency of the treatment unit is being improved, and the to-be-treated fluid is better mixed and dispersed through the flowing cycle environment.

When the pipeline forming in the cycle is used as a container for the to-be-treated fluid or a holding space for the to-be-treated fluid, the cycle can reach a sustainable equilibrium state simply by keeping introducing the to-be-treated fluid and discharging the treated fluid in the cycle. The flow velocity inside the pipeline can be relatively independent of the velocity of introducing to-be-treated fluid in the cycle. Therefore, the flow rate in the holding space inside the pipeline can be controlled based on a target effect of the treatment. For example, by setting a suitable flow rate inside the pipeline, the to-be-treated fluid can cycle in the pipeline for a plurality of times to fully contact the treatment unit and then be discharged from the cycle. For another example, in the case that the efficiency of the treatment unit is related to the flow rate, on the one hand, the flow rate inside the pipeline can be determined based on the efficiency of the treatment unit; on the other hand, by controlling the velocity of introducing to-be-treated fluid in the cycle (or the velocity of discharging treated fluid from the cycle), the average contact time or action time between the to-be-treated fluid and the treatment unit can be controlled. Thereby, the contact time or action time between the to-be-treated fluid and the treatment unit, and the flow rate inside the pipeline can be controlled independently.

In some embodiments, the fluid in the cycle is driven by at least one driving device connected to the pipeline.

Here, the driving device includes, but is not limited to, a peristaltic pump, a pressure pump, an electric field, a heater, a hydraulic pump, or a vacuum pump, which is used to provide power to the fluid in the pipeline to make the fluid cycle in accordance with the preset flow direction. Here, in the application for medical scenarios, the driving device does not directly contact the liquid, but only applies pressure to the pipeline and drives the liquid flow. The driving device is a peristaltic pump in a preferred embodiment.

In an actual scene, the flow rate of the fluid in the pipeline can be controlled by the driving device based on actual demand, such as based on factors including safety, economy, interception and separation effect, sustainability and the like. In one embodiment when the fluid treatment method is used for disease treatment, the to-be-treated fluid is the blood drawn from the human body, it is necessary to control the velocity of introducing to-be-treated fluid in the cycle within a preset range to ensure patient's safety.

It should be understood that in the embodiment provided by this disclosure, the effect of separation means a concentration difference of at least one component between in the fluid margin that has flowed through the treatment unit and is retained in the cycle, and in the fluid that has left the cycle through an outlet, rather than an absolute effect of separation or removal. For example, a component in the fluid that has left the cycle through the outlet may also exist in the fluid margin, but at least one component has a concentration difference between in the cycle and in the fluid that has left the cycle.

It should be understood that in the embodiment provided by the present disclosure, the interception (separation) means that a specific component or molecule in the treated fluid is blocked in the cycle to keep flowing after the treated fluid leaves the cycle, and the effect of interception is, for example, the proportion of the specific component or molecule blocked in the cycle.

In some embodiments, the total amount or total velocity of fluid introduced into the pipeline is equal to that of fluid discharged from the cycle, so that the total amount of fluid in the pipeline has a state of dynamical equilibrium.

It should be understood that the volume space in the pipeline keeps relatively constant by maintaining introducing the to-be-treated fluid in the cycle and discharging the treated fluid from the cycle, thereby the total amount of fluid in the pipeline is being a dynamically equilibrium, which is conducive to ensuring the stability of the internal pressure of the pipeline.

The flow rate of the fluid is controlled by the driving device to ensure the dynamic equilibrium of the total amount of fluid in the pipeline. The pressure in the pipeline maintains a constant value or fluctuates in a range determined by the constant value during the cycle, thereby avoiding problems such as pipeline rupture, negative pressure suction, destroy of fluid components, such as the rupture of red blood cells, etc. caused by the pressure change in the pipeline. Therefore, the cycle can maintain sustainable.

The pressure in the pipeline is related to the total amount of fluid in the pipeline. For example, the continuous decrease of fluid in the pipeline can easily lead to a negative pressure in a relatively closed pipeline. On the contrary, the continuous increase of fluid in the pipeline can easily lead to an increase of pressure in the pipeline. Negative pressure or excessive pressure has a negative impact on the effect of interception and separation of the fluid treatment and has a negative impact on the safety of the pipeline. For medical applications, when blood is used as the fluid, the excessive pressure in the pipeline will lead to a pipeline rupture or a damaged separation module, thereby leading to a failing treatment and even endangering the patient's health. Here, the driving device not only can provide power for the fluid of the cycle, but also can be used to ensure that the pressure in the pipeline is in a preset state, or adjust the pressure in the pipeline to the preset state.

In some embodiments, the cycle is carried out in a relatively closed space, for example, the cycle is a closed space after closing the inlet for introducing the to-be-treated fluid and the outlet for discharging the fluid. The internal pressure of the pipeline can be adjusted by the cycle due to its balance stability, for example, when a negative pressure state begins to appear inside the cycle, the negative pressure state then drives the velocity of introducing the to-be-treated fluid in the cycle to be greater than that of discharging the fluid, thereby the cycle can reach a pressure balance state again. Furthermore, the fluid can avoid contacting the external space after being introduced into the cycle. In some specific situations, such as blood delivery or protein extraction in medical scenes, the relatively closed space can provide a sterile environment or reduce bacterial, microbial, viral and other infections. In this embodiment, the fluid treatment method of the present disclosure reduces the interference of the external environment when the fluid flows and is treated in the pipeline by forming a relatively closed cycle environment, thus increasing the reliability of the treatment process.

In some embodiments of the present disclosure, the treatment efficiency of the cycle is adjusted by at least one of the following ways:

controlling the ratio of a total amount of the to-be-treated fluid introduced into the pipeline to a total amount of the fluid in the cycle per unit time;

controlling the ratio of a total amount of the treated fluid discharged from the pipeline to the total amount of the fluid in the cycle per unit time.

In order to better explain the advantages of the cycle in the fluid treatment method of the present disclosure compared with the traditional one-time flow treatment, it is assumed that the amount of the fluid introduced into the cycle per unit time is represented by $Q_{in}$, and the amount of the fluid introduced into the cycle per unit time represents the flow rate of the to-be-treated fluid at the inlet of the cycle; the amount of the fluid discharged from the cycle per unit time is represented by $Q_{filter}$, which may represent the flow rate of the treated fluid discharged from the cycle per unit time. $Q_{cycle}$ represents the amount of the fluid flowing in the cycle within the unit time, $Q_{cycle}$ can also represent the mass or volume of the fluid flowing through a specific area per unit time, where the specific area may be the inner surface of the pipeline. In the case where the connection mode of the hardware device or module in the cycle is determined, the $Q_{cycle}$ can be adjusted by controlling the flow rate in the cycle. $V_{total}$ represents the total volume of the fluid in the cycle. Generally, $V_{total}$ is determined by the specification of equipment implementing the fluid treatment method of the present disclosure, such as the volume determined by the total length of channels in the pipeline, the inner diameter of the pipeline, etc.

$$K1=Q_{in}/V_{total}$$

$$K2=Q_{filter}/Q_{cycle}$$

K1 represents the ratio of the amount of fluid introduced into the pipeline per unit time to the total amount of fluid in the cycle, and K2 represents the ratio of the amount of fluid discharged from the cycle to the amount of the fluid flowing in the cycle per unit time.

The smaller K1 and K2, the longer the to-be-treated fluid or a target substance remains in the cycle, and the easier or more efficient for the to-be-treated fluid or the target substance to be treated. Assuming that a certain volume of to-be-treated fluid is introduced into a linear pipeline at a constant amount $Q_{in}$ per unit time or at a constant flow rate, and then treated by the one-time flow treatment and the fluid treatment method of the present disclosure, respectively. In the case where both of the two methods are provided with a treatment unit in the pipeline and the efficiency of the treatment units are the same, the fluid treatment method provided in the present disclosure can improve the treatment efficiency by increasing at least one of $V_{total}$ and $Q_{cycle}$. In particular, when the one-time flow treatment cannot effectively achieve the effect, the same treatment unit or module can more effectively to achieve the above effect according to the fluid treatment method of the present disclosure. In addition, under the same other conditions, the treatment result of the target substance can be improved by increasing $Q_{in}$, and the fluid treatment method has a more obvious improvement effect than the traditional one-time flow treatment.

In an embodiment, the $Q_{in}$ is equal to the $Q_{filter}$ in an equilibrium state, the pipeline in the cycle remains filled with liquid, and correspondingly the total volume of the fluid margin in the cycle remains relatively constant. The average time of the to-be-treated fluid staying in the cycle can be determined by controlling the flow rate of the to-be-treated fluid introduced into the cycle, i.e. by controlling the $Q_{in}$, and the average contact time or action time of the to-be-treated fluid with the treatment unit can be determined accordingly. For example, for the cycle used in the fluid treatment method of the present disclosure, the holding space of the pipeline in the cycle is a relatively constant value. When the introduce velocity of the to-be-treated fluid is smaller, the contact time or action time of the to-be-treated fluid with the treatment unit in the cycle is longer, thereby the treatment effect or efficiency can be adjusted.

In another embodiment, the $Q_{filter}$ in the cycle is a constant value. The $Q_{cycle}$ is controlled by adjusting the flow rate in the cycle. Due to the flow rate in the cycle, the velocity of introducing, the velocity of discharging can be adjusted independently, the flow rate of the fluid in the cycle can be adjusted to a preset value without changing the flow rate of the treated fluid discharging from the cycle. The preset value can be determined based on the relationship between the treatment efficiency and the flow rate, thus, the treatment efficiency in the cycle can be adjusted according to the preset target.

The treatment effect described in the present disclosure, for example, refers to a removal rate or generation rate of the molecules or molecular combinations that need to be removed or generated in the to-be-treated fluid, where the removal rate or generation rate can be determined by comparing the to-be-treated fluid with the treated fluid that has been discharged from the cycle. The treatment efficiency described in the present disclosure, for example, refers to the rate at which the treatment unit selectively clears or generates molecules or molecular combinations.

In some embodiments of the present disclosure, the treatment unit realizes a catalytic treatment by controlling a catalytic unit in the cycle, where the treatment unit controls the catalytic unit in at least one of the following ways:

the treatment unit controls a type and total amount of the catalytic unit in the cycle by adding, supplementing, replacing, or updating the catalytic unit;

the treatment unit is configured to adjust activity of the catalytic unit in the cycle.

In the embodiments where a catalytic treatment is realized by the treatment unit, the cycle of the present disclosure is also called a metabolic cycle.

The treatment unit can be, for example, a component or device used to add the catalytic unit into or lead the catalytic unit out of the cycle for adding, supplementing, replacing, or updating the catalytic unit; or the treatment unit can be a structure or component used to fix the catalytic unit in the pipeline to realize the contact between the catalytic unit and the to-be-treated fluid in the pipeline; alternatively, the treatment unit can also be used to adjust the activity of the catalytic unit to achieve the catalytic treatment, for example, the treatment unit can be used to adjust the environment surrounding the catalytic unit in the cycle, such as temperature, pH, reaction substrate and other factors affecting the activity of the catalytic unit.

In some embodiments, the catalytic unit is used to change the chemical structure of a target substance in the fluid to generate a target product, or to change the concentration of the target substance in the fluid. The target substance described herein refers to a component in the to-be-treated fluid, and the target product refers to a component generated by the target substance under the action of the catalytic unit. In some scenarios, the target substance is the molecule to be removed or decomposed, and a goal of treating the to-be-treated fluid is to decompose or degrade the target substance to reduce the concentration thereof. In other scenarios, a goal of treating the to-be-treated fluid is to generate the target product by changing the chemical structure of the target substance based on the catalytic unit.

It should be noted that in the embodiments provided in this disclosure, the target substance is determined based on the preset target for fluid treatment. The target substances in the pipeline in different cycles can belong to the same or different categories, or the same or different components or molecules. For example, for the use in medical application, the target substance includes, but is not limited to, protein, lipoprotein, enzyme, antibody, DNA, amino acid, purine, sugar and polysaccharide, fat, cholesterol, vitamin, hormone, nutrition or energy molecule, biological factor, coagulation factor, metabolic waste, etc.; meanwhile, the target substance may be a substance that need to be separated and filtered out or need to be decomposed catalytically, including but not limited to immunoglobulin, immune complex, antibody, rheumatoid factor, endotoxin and inflammatory mediator, bilirubin, LDL, and virus, etc. (which are discarded as filtrate or waste liquid in some traditional application scenarios), the target substance may also be a synthetic or produced component in the treated fluid. The specific composition of the target substance can be changed based on the fluid composition and the preset target for treatment.

In some embodiments, the catalytic unit includes a biological catalytic unit and a non-biological catalytic unit. The biological catalytic unit includes at least one of a cell, a protein, an enzyme, a polypeptide and a nucleic acid; and a derivative, a conjugate, a complex, and an assembly in the form of a microsphere, microcapsule, etc. formed by at least one of the cell, protein, enzyme, polypeptide and nucleic acid. The non-biological catalytic unit includes a solid catalyst, a metal catalyst, or a derivative, a conjugate, a complex and an assembly in the form of a microsphere, microcapsule, etc. formed by the metal catalyst.

In some embodiments, the catalytic unit is formed by combining a material with catalytic function, such as an enzyme, with a carrier, which may be, for example, an inorganic carrier, a synthetic polymer carrier, a natural polymer carrier, and a composite carrier.

The catalytic unit is arranged in the pipeline or added when being used. The catalytic unit is arranged in the pipeline to contact the fluid, so as to change the structure or concentration of the target substance in the fluid. The catalytic unit may be, for example, a catalyst or a cell having a capacity of degrading, decomposing, generating, catalyzing the target substance or changing the structure of the target substance. It should be understood that the specific type of the catalytic unit, the derivative, the assembly and other forms are not limited to the foregoing examples. Generally, based on the type of the determined target substance, the catalyst or other substances that can achieve the preset treatment effect can be designed as a catalytic unit. Meanwhile, in specific application scenarios, safety, catalytic performance, and stability of a catalyst can be considered together to determine the specific type and form of the catalytic unit.

It should be understood that in each embodiment of the present disclosure, an interaction between the catalytic unit and the target substance not only includes a catalytic reaction, such as accelerating the decomposition, degradation and generation of the target substance, but also an adsorption, a local enrichment, and an influence of the catalytic reaction or the target substance or a product on the stability and catalytic activity of the catalyst, which may be beneficial or unfavorable to the treatment process.

The target product and the target substance may be the same substance or different substances, which means, the effect of the catalytic unit on the target substance may be to cause changes in the chemical structure or biomolecular structure of the target substance, or may be to change the physical structure of the target substance, such as causing the evacuated target substance to be condensed or causing the condensed target substance to be evacuated.

The catalytic unit is located in or connected to the pipeline, the catalytic unit can maintain a state of contacting with the fluid cycled in the pipeline, thus reacting with the target substance in the pipeline. The composition of the fluid in the pipeline changes dynamically.

In some embodiments, the catalytic unit is a cyclic catalytic unit participating in the cycle with the fluid margin; alternatively, the catalytic unit is a fixed catalytic unit confined to or fixed in a preset area of the pipeline.

The catalytic unit may be in a free state of motion, participating in the cycle along with the fluid margin; or the catalytic unit may be limited to a preset local area in the pipeline, the preset area may be a local area in the pipeline, or may be a device or equipment connected to the pipeline, such as a collecting device for pipeline expansion, as long as the device or equipment can contact the fluid margin in the cycle; or the catalytic unit can be fixed in the preset area, for example, the catalytic unit can be fixed on the inner wall of the pipeline, the inner wall of a cavity connecting the pipeline, the fiber or membrane in the pipeline or in the cavity connecting the pipeline. In conclusion, the catalytic unit can be free or fixed in the pipeline or any device or structure connecting with the pipeline, as long as the catalytic unit can contact the fluid to react with the target substance.

In some embodiments, the cycle also includes an interception module, which is arranged in the pipeline. The interception module has interception components to intercept the cyclic catalytic unit or/and the detached fixed catalytic unit to prevent the catalytic unit from leaving the cycle.

The opposite ends of the interception module are provided with interfaces corresponding to the pipeline to make the interception module connect with the pipeline and form a cycle.

The interception module can be separated into two opposite sides by the interception component, wherein the opposite ends of one side are connected with the pipeline, and the other side is connected with the outlet of the cycle, so that when the fluid passes through the interception module, the component intercepted in accordance with the flow direction flows to the pipeline through the interception module, and the treated fluid flows through the interception component to the outlet to leave the cycle.

In some embodiments, the interception component separates the interception module into a first side and a second side. The cycle includes at least one of the following: a first-type metabolic cycle in which the entrance and the exit of the pipeline are connected to the first side, with at least one inlet connecting the pipeline and at least one outlet connecting the second side; a second-type metabolic cycle in which the entrance and the exit of the pipeline are connected to the second side, with at least one inlet connecting the first side and at least one outlet connecting the first side.

In one embodiment, the inlet and the outlet of the cycle are connected to the same side of the interception module, and the entrance and the exit of the pipeline in the cycle are connected to the other side of the interception module, forming the second-type metabolic cycle. In another embodiment, the inlet of the cycle, the entrance and the exit of the pipeline in the cycle are all connected to the same side of the interception module, and the outlet of the cycle is connected to the other side of the interception module, the inlet of the cycle can be connected to the pipeline to form the first-type metabolic cycle.

In the embodiment provided in this application, the catalytic unit is located in the pipeline, causing that the catalytic unit remains on a side where the cycle is located at all times without leaving the cycle through the interception component. Different forms of interception components can be used, according to the structure, physical and chemical properties, and the carrier form or derivative form of the catalytic unit, and the state of motion (i.e. the aforementioned free state or fixed state) of the catalytic unit in the pipeline, to intercept the catalytic unit.

The interception component is used to intercept the catalytic unit in the first-type metabolic cycle and the second-type metabolic cycle; meanwhile, in the second-type metabolic cycle, the fluid passes through the interception component to enter the pipeline thereby being introduced into the cycle. In some scenarios, the interception component can pre-separate the fluid, for example, the macromolecular component in the fluid is intercepted at a first side of the interception module, and the fluid passing through the interception component enters the pipeline in the cycle to react under the action of the catalytic unit.

In the embodiment provided in this application, the catalytic unit is located in the pipeline, causing that the catalytic unit remains on a side of the cycle at all times without leaving the cycle through the interception component. Different forms of interception components can be used, according to the structure, physical and chemical properties, the carrier form or derivative form, and the state of motion (i.e. the aforementioned free state or fixed state) of the catalytic unit in the pipeline, to intercept the catalytic unit.

When using the cyclic catalytic unit in the cycle, in general, the interception effect of the interception module on the catalytic unit is expected to reach more than 99% to ensure that the catalytic unit will not leave the cycle and affect the system, and to ensure that the catalytic unit in the cycle will not be reduced to affect the treatment effect. The interception effect refers to the fact that when the fluid in the cycle passes through the interception module, there is no obvious concentration difference of components between the intercepted fluid remaining in the cycle and the discharged fluid leaving the cycle through the interception module, except for the components of the cyclic catalytic unit, indicating that the discharged fluid and intercepted fluid both contains the target substance or target product, as well as other components in the to-be-treated fluid.

For this reason, the interception component can be a component with selective permeability, so that the catalytic unit in the fluid can be intercepted in the cycle, and both the to-be-treated fluid and the treated fluid can leave the cycle through the interception module; thus, the to-be-treated fluid can be continuously replenished in the cycle, and the treated fluid can continuously leave the cycle through the interception module.

The specific form of the interception module can be determined according to the catalytic unit. For example, the catalytic unit is a free enzyme, correspondingly, the interception module may have a structure that has no permeability to the free enzyme, for example, the average diameter of pores of the interception module is smaller than the particle size of the free enzyme, so that the free enzyme is intercepted in the cycle.

For example, the catalytic is an enzyme, the enzyme that can participate in the cycle along with the fluid margin can also be enzyme-loading microspheres, enzyme-loading microcapsules, water-soluble macromolecules that bind to the enzyme, etc. In this example, problems such as enzyme deformation and inactivation caused by chemical reaction occurs when combining the enzyme with the carrier can be avoided. Based on the different forms of the enzyme carrier, the corresponding interception modules in the cycle can be set in different forms to achieve the interception of the enzyme. For example, the average diameter of pores of the interception component is used to achieve the interception of the enzyme-loading microspheres, while filtering out the treated fluid. In one embodiment, the size of a microsphere is much larger than that of an enzyme, which greatly improves the average diameter of pores and the amount of intercepted molecules of the interception component, breaking through the restriction of the diameter of pores on the flow rate of filtering and introducing, thereby can better control the flow rate of the fluid introduced into the cycle (also be expressed as $Q_{in}$ mentioned above), increasing the amount of fluid introduced in and discharged from the cycle, which is conducive to improving the absolute value of the treatment capacity of the cycle treatment.

In one embodiment, the design or selection of the interception module can be determined by the type of corresponding catalytic unit and the target product, so that the interception module intercepts the catalytic unit in the pipeline, while the target product can pass through the interception module to leave the cycle. For example, in medical application, when the catalytic unit is an enzyme-loading microsphere and the to-be-treated fluid is plasma, the enzyme-loading microsphere enables biological molecules such as toxic metabolites in the blood to be decomposed into metabolites, correspondingly, the interception module can be determined based on the particle size of the enzyme-loading microsphere and the metabolites, so that the metabolites are driven out of the cycle when passing through the interception module, and the enzyme-loading microspheres as a catalytic unit are intercepted in the pipeline.

In the fluid treatment method of the application, the utilization rate of the catalytic unit can be improved by retaining the catalytic unit at the side where the cycle exists; besides, the catalytic unit can be in contact with the fluid margin by keeping the catalytic unit in the pipeline all the time, thus forming a continuous reaction, such as continuous catalysis and continuous decomposition.

In some scenarios, by forming free catalytic units as described, the continuous impact and scouring of the catalytic units by the fluid can be avoided and slowed down, reducing the resulting fragmentation as well as the formation of protein deposits and gel layers. The fluid treatment method of the present disclosure can be used to form a dynamic reaction environment between the catalytic unit and the target substance within the pipeline. The catalytic unit is distributed in the pipeline in a free form, which is conducive to full contact with the target substance. Meanwhile, the catalytic unit can flow along the cycle direction in line with the dynamic environment in the pipeline, and the catalytic unit flows tangentially along the inner wall of the pipeline, thereby the collision problem of the catalytic unit reaction environment can be reduced. Through the fluid treatment method of the present disclosure, not only the target substance can be fully contacted to improve the catalytic effect, but also the probability of the catalytic unit being damaged can be reduced.

In some embodiments, the catalytic unit is intercepted inside the pipeline by the interception component for cyclic flow, and the reaction product, target substance and other components in the to-be-treated fluid leave the cycle through the interception module.

The catalytic unit in the free state can participate in the cycle along with the fluid margin, and participate in the catalytic reaction during the cycle. The corresponding reaction product, together with other untreated components, leaves the cycle through the interception component. In this embodiment, the components of the fluid margin are kept updated by introducing a fluid in the cycle, by this way, the target substances that can be used to react with the catalytic unit are continuously replenished in the pipeline, and the target products can leave the pipeline in time, which can be used to control the concentration of target substances in the pipeline, and can be used to improve the catalytic efficiency of the catalytic unit. It should be understood that in general, the catalytic efficiency of the catalyst is related to the concentration of a substrate. The target substance may refer to the substrate that can react with the catalyst. The volume of the pipeline is relatively constant, thereby the concentration of the target substance in the pipeline can be determined by making the target product leave the cycle and the pipeline.

In some embodiments, the interception component comprises a porous membrane or a reverse osmosis membrane, wherein the porous membrane includes a microfiltration membrane, an ultrafiltration membrane, and a nanofiltration membrane.

The specific type of the interception component can be determined based on the difference in physical and chemical properties between the component of the fluid and the catalytic unit such as the cyclic and the detached fixed catalytic unit. The interception component is used to retain the catalytic unit and allow other components in the fluid to filter through. For example, the type of the interception component includes: reverse osmosis membrane (average pore size 0.0001-0.001 μm), nanofiltration membrane (average pore size 0.001-0.01 μm), ultrafiltration membrane (average pore size 0.01-0.1 μm), microfiltration membrane (average pore size 0.1-10 μm), electrodialysis membrane, pervaporation membrane, liquid membrane, electrode membrane, etc.

In some embodiments, the interception component includes one or more of a planar membrane, a tubular membrane, a roll membrane, a spiral membrane, and a hollow fiber membrane. In terms of microstructure, the interception component can include symmetrical membrane, asymmetrical membrane, composite membrane, multilayer composite membrane, etc.

In some embodiments, the average pore diameter or molecular weight cutoff (MWCO in short) of the interception component is related to at least one of the catalytic unit, target substance, and target product.

In one embodiment, the average pore diameter or molecular weight cutoff of the interception component can be smaller than the particle diameter or molecular weight of the catalytic unit in order to intercept the catalytic unit inside the pipeline. In some embodiments, the average pore diameter or molecular weight cutoff of the interception component can be much smaller than the particle diameter or molecular weight of the catalytic unit to achieve a better effect of interception.

For example, when the catalytic unit is in a free state cycling with the fluid margin, the average pore diameter or molecular weight cutoff of the interception component is related to the catalytic unit. Here, the membrane for separation can be determined based on the specific structure of the catalytic unit in order to achieve the interception effect. In some scenarios, the pore diameter and type of the membrane for separation can be determined based on a goal expecting more than 95% of the catalytic unit can be intercepted, or a higher goal expecting more than 99% or even more than 99.9% of the catalytic unit can be intercepted. Using an enzyme as the catalytic unit, the problem of enzyme shedding in a conventional enzyme therapy can be greatly reduced or even avoided in the present disclosure.

In another embodiment, in the case that the target substance also needs to be retained by the interception component, the average pore size or molecular weight cutoff of the interception component is related to the target substance. In actual scenarios, the membrane suitable for intercepting the target substance is selected based on the composition of the fluid and the target substance. For example, when the size of the target substance to be intercepted in the fluid is 10 nm (i.e. 0.01 μm), the corresponding membrane used as the interception component can be a nanofiltration membrane or reverse osmosis membrane to achieve the interception for the target substance.

In some embodiments, the reaction product can pass through the interception component to leave the cycle module. Correspondingly, the average pore diameter or molecular weight cutoff of the interception component can be set to be larger than the particle size or molecular weight of the target reaction product.

The type of interception component is determined by comprehensively considering the factors such as the interception target and the filtration target of the catalytic unit in the fluid. For example, in the case where the catalytic unit is fixed in the pipeline, the catalytic unit may be washed away by the fluid and cause it to fall off and be free in the cycle. In this case, the interception module can be used as a means to prevent the free catalytic unit from leaving the cycle. Based on the composition of the fluid and the type of catalytic unit, it can be determined whether the catalytic unit is fixed or free, and the average pore diameter or molecular weight cutoff of the interception module can also be determined, so that the fluid and the reaction product can be removed from the cycle through the interception module and the catalytic unit is retained in the cycle. Generally speaking, when the interception component realizes the function of separation based on the pore size, its pore diameter needs to be larger than the component having the maximum particle size or molecular weight in the fluid and smaller than the catalytic unit.

In some embodiments, the average pore diameter or molecular weight cutoff of the interception component suitable for intercepting or filtering the target component can be determined based on the fluid components, target substances, and the catalytic unit. In some embodiments, the interception component is a separation membrane. When determining the specific type of the separation membrane, the Donnan effect, adsorption, and dissolution effect of the separation membrane can also be comprehensively considered, thereby setting a suitable separation membrane in the interception module that can achieve a preset interception and separation effect. In some embodiments, the type and size of the catalytic unit can be determined based on the fluid components and target substances, and then the pore diameter and molecular weight cutoff of the separation membrane can be further determined. In other embodiments, the fluid can be pretreated or circularly separated to obtain the fluid containing the target substance with a small average molecular weight, then the type and size of the catalytic unit can be determined, and the pore diameter and molecular weight cutoff of the separation membrane can be further determined. In terms of microstructure, the separation membrane can include symmetrical membrane, asymmetrical membrane, composite membrane, multilayer composite membrane, etc.

In some embodiments, the interception module is a Tangential/Cross Flow Filtration Module (TFFM).

It should be understood that since the separation is driven by the transmembrane pressure difference on a boundary surface in the Tangential/Cross Flow Filtration Module, the adjustment of the pressure difference used to drive the transmembrane can be achieved by controlling the flow rate of the fluid at the interception module, thereby adjusting the separation efficiency or interception efficiency.

In some embodiments, the tangential/cross flow filtration module can use one of the following: a traditional membrane cassette of tangential flow filtration, such as the Pellicon box cassette with ultrafiltration membrane of Merck & Co Inc; the leucocyte filter, the virus filter, the LEOCEED dialyzer, or the membrane plasma separator of Asahi Kasei Corporation; and the plasma separator of Braun GmbH. It should be noted that, on the one hand, the tangential/cross flow filtration module can be used in different fields to achieve different separation effects, for example, it can be used to achieve material collection, such as retaining materials in the pipeline, or treating industrial wastewater, etc., which will not be limited to the application scenarios of the aforementioned products; on the other hand, in actual application scenarios, the pore size or molecular weight cutoff, as well as the geometry of the membrane in tangential/cross flow filtration module is determined based on the purpose for filtering or retaining each component in the fluid, without being limited by the aforementioned examples.

In this embodiment, by means of driving a separation through the pressure difference in the TFFM, the present disclosure cannot only retain cyclic catalytic unit in the fluid, but also enable the intercepted treatment unit to continue to participate in the cycle in accordance with the flow direction to achieve a cyclic treatment. In actual applications, for example, the pressure difference can be adjusted by controlling the flow rate of the fluid passing through the TFFM in the cycle, thereby changing the transmembrane-exchange efficiency of the fluid, or, the exchange efficiency can be changed by changing the type of the TFFM such as changing the flow channel or the pore diameter of the porous membrane, or changing the viscosity of the fluid, such as by diluting the fluid.

It should be understood that in the TFFM, the fluid flows tangentially relative to the surface of the membrane, which means that the angle between the flow direction of the fluid and the surface of the membrane is 0°, in actual applications, the angle between the flow direction of the fluid and the surface of the membrane may also be other angles such as 5°, 10°, etc., which also enable the intercepted substances to leave the surface of the membrane to continue to participate in the cycle.

In some embodiments, the to-be-treated fluid is introduced to the cycle from the inlet and driven by the driving device to flow to the interception module.

The driving device is correspondingly arranged between the inlet and the interception module, and drives the fluid in the pipeline from the inlet through the driving device and then flows into the interception module. By this way, the control device can control the flow rate of the fluid passing through the interception module.

In some embodiments, following the flow direction of the fluid in the cycle, the driving device can also be arranged on the pipeline connected behind the outflow of the interception module, which means that the fluid can be driven by the driving device after passing through the interception module to form a cycle.

It should be understood that the driving devices at different positions in the pipeline can drive the fluid in the pipeline. In the direction of fluid flow, the flow rate of the fluid may be influenced by factors such as pipeline resistance, temperature, and pressure. In the embodiment provided in this application, the driving device is arranged between the inlet and the interception module, thereby driving the to-be-treated fluid introduced from the inlet to flow to the interception module, and controlling the flow rate of the fluid at the interception module. For example, the interception module is provided with a separation membrane, the angle between the flow direction of the fluid and the separation membrane can be set to different angles, such as 0°-90°. The flow rate of the fluid relative to the separation membrane is related to the interception and separation effects. The interception and separation effects of the fluid treatment method of the present disclosure can be controlled by changing the position of the driving device. Factors that can be used to represent the interception and separation effects include but are not limited to membrane flux, separation rate, interception ratio of cyclic catalytic unit and transmissivity of other components of the fluid.

In actual applications, the driving device can also be arranged at any position in the pipeline. Herein, the number and position of the driving device can be determined based on the shape of the pipeline, the total amount of the fluid, the power of the driving device, the preset flow rate for the cycle, etc.

The fluid treatment method of the present disclosure controls the cyclic flow of fluid in the pipeline through the driving device and maintains the dynamic equilibrium of the total amount of fluid, and determines the specific form of the interception module according to the fluid component and the cyclic catalytic unit, so that the fluid treatment method can achieve a selective treatment for target molecules in the fluid. Moreover, the pipeline cannot only be used for flowing fluid, but also can be used as a container in the treatment process, which means it can be regarded as a cyclic processor or a cyclic reactor. In actual scenarios, such as in medical applications, the pipeline can be used to effectively simplify structure or reduce space of the device for executing the fluid treatment method of the present disclosure, and correspondingly, simple devices that are easy to use or carry or wear can be formed. Further, when a catalytic unit is used, the results of the treatment of the to-be-treated liquid can be controlled or reflected by the following methods, including but not limited to: determining the time of cycling based on the interception and separation effect of the interception module, the ratio of filtered fluid volume to the cyclic liquid, and the treatment effect of specific components, etc., which means that the number of cycles in the pipeline or the duration of the cycle can be controlled based on a preset target for treatment.

In some embodiments, the driving device controls the fluid in the pipeline to flow at a preset flow rate so that the catalytic unit flows to the pipeline through the interception module.

For example, when the interception module is the TFFM, the flow direction of the fluid is parallel to the separation membrane in the TFFM. When the fluid passes through the separation membrane in the TFFM, a transmembrane pressure difference perpendicular to the surface of the membrane is generated on both sides of the membrane to drive the components with small molecular weight in the fluid to pass through the separation membrane and reach the other side. The components with small molecular weight passing through the separation membrane can thereby leave the cycle, while the intercepted catalytic unit or other macromolecular components that need to be intercepted are washed away from the membrane surface and driven by flowing fluid and continue to cycle in the pipeline. The pressure difference on both sides of the membrane in the TFFM is related to the preset flow rate. Besides, the intercepted substances require a certain amount of momentum to overcome the polymerization inhibition between the catalytic units or between macromolecular components, or between the catalytic units or macromolecular components and the membrane, so as to continue the cycle. The driving device controls the flow rate of the fluid in the pipeline, thereby can be used to control the pressure difference on both sides of the separation membrane to achieve the interception and separation effects, and can be used to prevent polymerization inhibition to ensure the sustainability of cycle in the pipeline.

In some embodiments, the preset flow rate is related to at least one of the catalytic unit, composition of the fluid, temperature of the fluid, structure of the interception component, material of the interception component, cavity structure of the interception module, diameter of the pipeline, efficiency for exchanging the target substance or reaction substrate with the catalytic unit, and efficiency for exchanging the fluid. Wherein the composition of the fluid includes the type of the fluid component and the corresponding concentration of each component.

The flow rate of the fluid at the interception module is related to several different parameters, for example, the flow rate of the fluid at the interception module may be changed according to the parameters including: characteristics of the fluids such as the density and viscosity of the fluid; a shape of the boundary layer of the fluid at the interception module, such as the surface shape of the separation membrane (i.e. structure of the membrane) and the cavity structure of the interception module; an interaction force between the fluid and the separation membrane, such as the surface roughness of the membrane determined by the membrane material; an attraction between the fluid and the separation membrane; and a relationship between flow rates at the interception module and at the entrance of the pipeline determined by the cavity structure of the interception module and the diameter of the pipeline. The preset flow rate can be used to determine the flow rate of the fluid at the entrance of the pipeline flowing to the interception module, a threshold value of the preset flow rate can be used as the initial flow rate at the interception module. According to the initial flow rate and the parameters mentioned above related to the flow rate of the fluid at the interception module, the fluid flow rate at the interception module can be determined by controlling the preset flow rate, resulting in a pressure difference to achieve separation, preventing intercepted macromolecular substances such as catalytic units from gathering on the surface of the membrane, thereby, macromolecular substances can flow from the entrance of the pipeline through the interception module to the exit of the pipeline.

In some embodiments, the preset flow rate is related to the efficiency for exchanging the fluid. For example, in the TFFM, the target product is driven by the pressure difference on both sides of the separation membrane to flow to the other side of the interception module after a certain flow rate is reached, thus leaving the cycle. The pressure difference is related to the flow rate, the efficiency for exchanging the target product and other components in the to-be-treated fluid may decrease when the flow rate is too low. Therefore, the preset flow rate can also be determined by the efficiency of exchange. For example, the $Q_{cycle}$ or K2 in the cycle can be determined by controlling the preset flow rate to control the efficiency and time of exchanging the target substance or reaction substrate with the catalytic unit, so as to realize the adjustment to the treatment efficiency.

The preset flow rate can also be used to control the treatment efficiency in the cycle. For example, the preset flow rate is related to the efficiency of exchanging the target substance or reaction substrate with the catalytic unit. It should be understood that when the treatment unit achieves the function of treatment by contacting the target substance or reaction substrate, the state of contacting or mixing of the target substance or reaction substrate with the catalytic unit can be controlled or adjusted by correspondingly controlling the flow rate in the cycle.

In some embodiments, the cycle is also provided with a sampling device for adding, supplementing or replacing reaction substrates, catalytic units, drugs, and other cofactors or activators to the pipeline.

In this embodiment, the sampling device can be used as a treatment unit. Through the sampling device, the catalytic units, reaction substrates, activators, etc. can be added, supplemented or replaced to the cycle under manual control or under the control of a computing device, thus the catalysis of the fluid can be realized. In actual applications, the sampling device can also be used to control the concentration of the catalytic unit in the cycle. For example, when the concentrations of the target substance in the to-be-treated fluid becomes different, the amount of the catalytic unit added to the pipeline can be correspondingly controlled to achieve a preset reaction effect.

The sampling device can be set as a component integrated with the pipeline, or it can have two opposite access ports to connect the pipeline and to ensure a cycle of the fluid. The catalytic unit or reaction substrate can be added into the pipeline immediately through the sampling device; the reaction substrate may be any component in the to-be-treated fluid or a substance that can interact with any component in the to-be-treated fluid, wherein the interaction includes but is not limited to biological reaction, chemical reaction and physical reaction. The cofactor or activator can be used to assist the reaction between the catalytic unit and the target substance, for example, in the case where the catalytic unit is a metal enzyme that requires metal ions as a cofactor.

For example, in the traditional enzyme therapy, the enzyme that can be used as a catalytic unit is usually fixed in a container, such as in the inner wall of a container, a fiber, a membrane, and the inner wall of a cavity, which means that when enzymes are an inherent component of the treatment device, it is difficult to adjust the activity of the enzymes in the device after they have been immobilized and after the catalytic reaction has begun; meanwhile, the inner wall of the container or the membrane is usually used as a storage environment for the enzyme, for an enzyme with short half-life, there are many restrictions on the requirements for preserving the whole device and the requirements for reaction time, for example, it is necessary to place the whole device in an environment with low temperature to preserve the enzyme immobilized therein.

In the equipment or device implementing the fluid treatment method of the present disclosure, the sampling device can be used to realize the immediate updating, replacement and supplement of the catalytic unit, which is beneficial to control the catalytic efficiency in fluid treatment in practical applications, and can effectively relax the restrictions on the environment for preserving the catalytic unit, so that the catalytic unit and pipeline can adopt different storage conditions, reducing the restrictions on storage condition of the whole equipment for performing the fluid treatment method. For some specific catalytic units, such as enzymes, the catalytic units can be separately preserved in a low-temperature environment distinguished from the device. For specific enzymes with short half-life, they can be preserved in a form of freeze-dried powder, and are dispersed into an aqueous phase and injected into the sampling device when being used, thereby ensuring the activity of the enzymes that react with the target substances.

In some embodiments, the sampling device includes at least one sampling inlet connected to the pipeline, or the sampling device is a component suitable for the injection form.

The sampling inlet is connected to the pipeline, by this way, the catalyst unit, reaction substrate and other substances injected through the sampling inlet can enter the cycle through the sampling device.

In an embodiment, the sampling inlet of the sampling device can also be equipped with a corresponding plug cock or sealing cap, which opens during sampling and closes after sampling, to ensure that the inside of the pipeline remains relatively closed.

In another embodiment, the sampling device can be equipped with a permeable component such as a rubber plug, which can form a sampling inlet by injection or puncture during sampling. For example, the catalytic unit or reaction substrate to be added to the pipeline can be stored in a syringe, and the rubber plug can be punctured by the syringe for adding the catalytic unit or reaction substrate to the sampling device.

In some embodiments, the cycle device is equipped with a collecting device, the collecting device has a collecting chamber for mixing the cyclic catalytic unit, the fluid margin and the to-be-treated liquid to make the catalytic unit contact with the target substance.

The collecting device can be used to expand a volume of the cycle. In each example where the fluid is liquid, the collecting device can help the cycling liquid to better mix with the cyclic catalytic unit, so that the target substance can fully contact the cycle catalytic unit.

In some embodiments, the collecting device is further provided with a sampling inlet, air inlet-outlet or a liquid outlet. In this embodiment, the collecting device can also be used as a platform for integrating various liquid inlets and outlets or air inlets and outlets, and a place for the intersection and mixing of various liquids.

In one embodiment, the collecting device is arranged in a location in the pipeline where the fluid in the collecting device can have a tendency to flow in the direction of cycling based on gravity when the collecting device is naturally placed. Such design can avoid or reduce the generation of bubbles in the pipeline. In this embodiment, the collecting device can also be equipped with an air inlet-outlet to adjust the internal air pressure of the cycle.

In some embodiments, the cycle is also provided with a channel-adjusting device, which is used to adjust the flow direction of the fluid in the pipeline; in some embodiments, the channel-adjusting device can adjust the flow direction of the fluid in the pipeline by at least one of the following ways:

Adjusting the flow direction of the fluid by adjusting the switching state of the inlet or/and outlet of the cycle;

Adjusting the flow direction of the fluid by adjusting the switching state of at least one adjusting channel connected to the pipeline.

In some embodiments, the channel-adjusting device can be used to realize the cleaning and replacement of the cyclic catalytic unit. For example, by closing the inlet to stop supplementing the to-be-treated fluid to the cycle, the cycle is changed to a concentrated cycle mode, which means that the treated liquid leaves the cycle and the catalytic unit is still retained in the cycle; the cyclic catalytic unit can be cleaned by supplementing a cleaning solution into the cycle and discharging the cleaning solution based on at least one adjusting channel connected to the pipeline; after cleaning, a new catalytic unit can be added to the cycle to meet the needs of treating different target substances.

By controlling the switch state of a channel in the channel-adjusting device, the flowing direction and the channel for cycling the fluid in the pipeline can be changed. For example, in a normal cycling state, the cycle keeps introducing the to-be-treated fluid and discharging the treated fluid, and the cyclic catalytic unit thereby completing the cyclic treatment normally; when the efficiency of the cyclic catalytic unit is obviously reduced or lost, the adjusting channel is opened and the pipeline is closed through corresponding switches, and the inlet of the cycle is closed, one end of the two adjusting channels is connected to the pipeline, and the other end is used as an entrance and an exit of the pipeline respectively. The two adjusting channels cooperate with the pipeline to form a new flow channel, and the cyclic catalytic unit in the pipeline can be drawn out of the pipeline through the entrance and the exit. In addition, a cleaning solution can be introduced into the pipeline to clean the pipeline under a cleaning mode, the cleaning solution can enter the pipeline through the entrance and pass through the interception module to clean the inner wall of the pipeline and clean the interception module. When the cleaning is completed, a new cyclic catalytic unit can be added to continue a selective treatment for the target substance in the fluid, which can be a same treatment for the same target substance or a different target substance, depending on the specific requirements.

Figure 3:
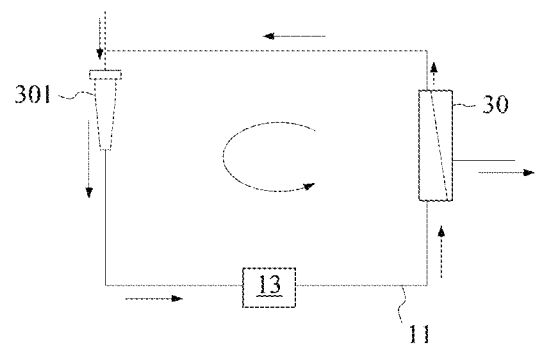
FIG. 3 shows a simplified schematic diagram of a metabolic cycle module in an embodiment of the present disclosure.
Figure 4:
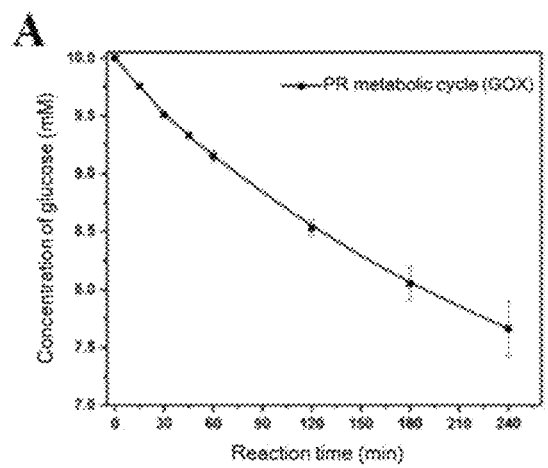
FIG. 4 shows the result of Experiment 1 of the present disclosure.

In order to explain the beneficial effects achieved by the first-type metabolic cycle provided by the present disclosure, the following experimental data is provided herein:

Experiment 1:

Please refer to FIG. 3 and FIG. 4, where FIG. 3 shows a simplified schematic diagram of a metabolic cycle module used in Experiment 1 in an embodiment, and FIG. 4 is a diagram showing the data of Experiment 1 obtained based on the metabolic cycle module of FIG. 3.

As shown in FIG. 3, the metabolic cycle module includes a pipeline 11 and an interception module 30. The interception module 30 is a tangential/cross flow filtration module. The interception module 30 used in Experiment 1 is a commercial M-TFFM with a molecular weight cutoff of 10 kD. The pipeline 11 includes a driving device 13 and a sampling device 301. The fluid from the interception module 30 is connected to an inlet of the metabolic cycle module, which is arranged at the sampling device 301 in the embodiment illustrated in FIG. 3. Herein, the sampling device 301 can also be used as a collecting device.

Experimental process: add 100 mL glucose solution (10 mM, phosphate buffer saline, PBS buffer) into the collecting device connected to the inlet. Drive the glucose solution to pre-fill the pipeline through the driving device, the total amount of the liquid in the pipeline is about 50 mL. Adjust the flow rate of the liquid at the inlet so that it is equal to the flow rate of the liquid discharged from the outlet, thereby forming a balanced cycle.

After forming the balanced cycle, add 1 mL of GOX (glucose oxidase) solution (containing 0.1 mg of GOX, about 14.5 U in total) through a sampling inlet, start timing, take samples in the collecting device to determine the concentration of hydrogen peroxide, and convert the total amount of degraded glucose from hydrogen peroxide.

Repeat the above experimental process, conduct three independent experiments respectively, and take the average value of the concentration of glucose measured and calculated in the three experiments. FIG. 4 shows the curve of the concentration of glucose obtained by the average of the three experiments as a function of time.

It can be seen from the results shown in the figure that with the increase of treatment time, the concentration of glucose continues to decline, and there is no significant decline in the degradation rate. That is, continuous metabolism can be carried out in the metabolic cycle module, and the catalytic function is stable within 4 h of the time of experiment, with little activity attenuation.

Figure 9:
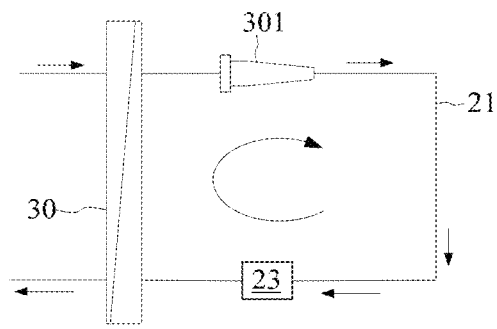
FIG. 9 shows a simplified schematic diagram of a metabolic cycle module in an embodiment of the present disclosure.
Figure 10:
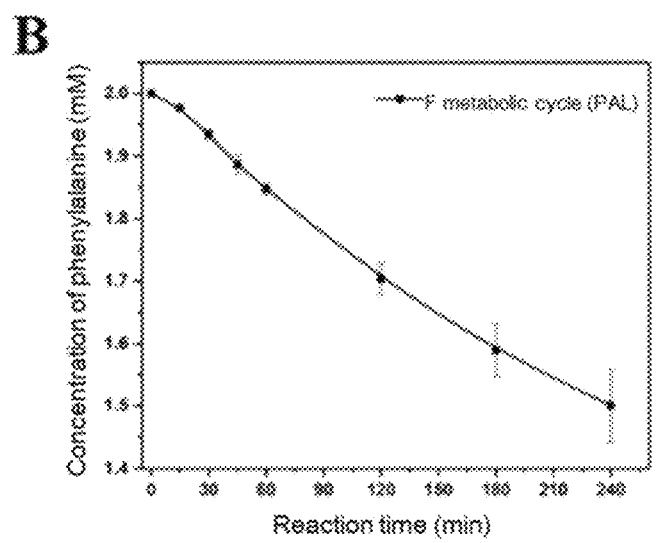
FIG. 10 shows the result of Experiment 2 of the present disclosure.

In order to explain the beneficial effects achieved by the second type of metabolic cycle provided by the present disclosure, the following experimental data is provided herein:

Experiment 2:

Please refer to FIG. 9 and FIG. 10, where FIG. 9 shows a simplified schematic diagram of a metabolic cycle module used in Experiment 2 in an embodiment, and FIG. 10 is a diagram showing the data of Experiment 2 obtained based on the metabolic cycle module of FIG. 9.

FIG. 9 shows a metabolic cycle module of the second type of metabolic cycle, the metabolic cycle module includes a pipeline 21 and an interception module 30. The interception module 30 is a tangential flow filtration module. The interception module 30 used in Experiment 2 is a commercial D-TFFM with a molecular interception cutoff of 10 kD. The pipeline 21 includes a driving device 23 and a sampling device 301.

Experimental process: add 100 mL phenylalanine solution (2 mM, PBS) into a container connected to the inlet, the liquid in the container can be connected to a first side of the separation module through the inlet, and the fluid that passes through the separation component can flow into the pipeline. Drive the phenylalanine solution to pre-fill the pipeline by a peristaltic pump, the total amount of liquid in the metabolic cycle module is about 10 mL. Adjust the flow rate of the liquid at the inlet so that it is equal to the flow rate of the liquid discharged from the outlet, thereby forming a balanced cycle.

After forming the balanced cycle, add 3 mL of phenylalanine ammonia lyase (about 2.84 U) through the sample inlet, start timing and take samples in the collecting device to determine the concentration of the product of trans cinnamic acid, where the concentration of trans cinnamic acid is determined by its UV absorption peak at 280 nm, and the concentration of phenylalanine is calculated from the concentration of trans cinnamic acid.

Repeat the above experimental process, carry out four independent experiments respectively, and take average value of the concentration of phenylalanine measured and calculated in the four experiments. FIG. 10 shows the curve of the concentration of phenylalanine obtained by the average of the four experiments as a function of time.

It can be seen from the results shown in the figure that with the increase of reaction time, the concentration of phenylalanine continues to decline, and continuous metabolism can be carried out in the metabolic cycle module, and the catalytic function is stable within 4 h of the time of experiment, with little activity attenuation.

In order to explain the interception effect of the metabolic cycle of the present disclosure on the catalytic unit, the present disclosure further provides an Experiment 3.

Experiment 3:

The metabolic cycle module corresponding to the first type of metabolic cycle (molecular weight cutoff of 10 kD) was tested. Continuously replenish water at the inlet to pre-fill the pipeline. After forming a balance, add 1 mg of GOX (molecular weight of 160 kD) from the sample inlet to the pipeline of the metabolic cycle module, and separately collect the liquid discharged from the outlet of the metabolic cycle module, i.e. a filtered out liquid, and sample the filtered out liquid to determine the concentration of GOX. The results shows that for every 100 mL of liquid filtered, 3.46 μg (i.e. 0.346%, 1 mL of liquid was sampled for three times, and the result is obtained by activity determination) of GOX was discharged from the outlet.

The metabolic cycle module corresponding to the second type of metabolic cycle (molecular weight cutoff of 10 kD) was tested. Continuously replenish water at the inlet to pre-fill the pipeline. After forming a balance, add 1 mg of GOX from the sample inlet to the pipeline of the metabolic cycle module, and separately collect the liquid discharged from the outlet of the metabolic cycle module, and sample the liquid discharged from the outlet to determine the concentration of GOX. The results show that 0.18-0.54% of 1 mg GOX was discharged from the outlet during a cycle of hours.

The metabolic cycle modules corresponding to the first type of metabolic cycle and the second type of metabolic cycle respectively have a good interception effect, thereby can prevent the catalytic unit from entering the downstream cycle, such as the blood cycle in medical applications, and prevent the decline in the catalytic function of the cycle caused by the loss of the catalytic unit, in specific scenarios, especially in medical applications, an immune reaction caused by the catalytic unit or carrier entering the blood cycle or other body fluid cycle can be avoided.

Based on the results of Experiment 1, Experiment 2 and Experiment 3, in an embodiment where an enzyme is taken as the catalytic unit, the metabolic cycle module of the present disclosure further provides a method that the catalytic unit can be replaced, the treatment process can be verified and tracked, on the basis of solving the problems such as the enzyme shedding and entering the downstream of and even the whole blood cycle, the low efficiency of the contact and exchange between the enzyme and the liquid to be treated, and the sustainability of the treatment process, to monitor and evaluate the whole process of selective treatment.

In order to explain the beneficial effects that can be achieved by the fluid treatment method of the present disclosure, the following description is provided herein:

For example, the catalytic unit is an enzyme, which is a protein or RNA produced by a living cell that has a high specificity and catalytic efficiency for its substrate, indicating that the enzyme undertakes the catalytic function in the process of biomolecule synthesis and metabolism. Based on the specificity of the enzyme, it can be used to selectively degrade or change the concentration of a molecule in the body, and has great medical value for the treatment of metabolic diseases, cancer and some infectious diseases.

However, the enzyme will not only be eliminated by the immune system and lose the therapeutic function, but also trigger an immune response when directly injected into the blood circulation as an medicine. Being modified by Polyethylene glycol (PEG) can effectively reduce the immunogenicity of the enzyme and become the only technology solution used in clinical enzyme therapy. For example, the pegloticase of Savient Pharmaceuticals, Inc. was approved by the FDA to be listed in 2011 for the treatment of refractory gout that failed to be treated with common drugs, and the pegvaliase pqpz of Biomarin Pharmaceutical Inc. was approved by the FDA in 2018 for the treatment of adult phenylketonuria. However, due to the modification of PEG cannot completely cover up the antigenic properties of the enzyme, infusion reactions and allergic reactions in some patients are very serious. More importantly, after repeated injections, PEG itself has produced an antigen response, significantly reducing the blood half-life of the drug and producing serious drug resistance. The clinical value of the enzyme modified by PEG is seriously restricted by toxic side effects and drug resistance, the enzyme modified by PEG can only play a short-term role in patients with chronic diseases before drug resistance.

A traditional method is to draw out the blood, use enzyme/catalytic unit in vitro to continuously change the concentration of specific molecules in the body, and avoid the enzyme/catalytic unit from entering the blood cycle. For example, in the U.S. Pat. No. 4,955,857, a common medical blood dialyzer is used to encapsulate a therapeutic enzyme solution in a cavity or connect the two ends of the dialyzer to drive the flow of the enzyme solution. The blood passes through the hollow fibrous membrane, and the substrate enters the cavity through osmosis and reacts with the enzyme solution. However, the diameter of pores in the medical blood dialyzer is too large, which causes a problem that the therapeutic enzyme diffuses and flows into the blood cycle, and causes a poor mass transfer effect of dialyzer.

Clara Ambrus et. al immobilize the enzyme outside a hollow fibrous membrane with 10 kD (KiloDalton), make a multi-channel enzyme reactor by covalent fixation, and the substrate enters the outer cavity through diffusion to contact with the enzyme. However, the mass transfer efficiency of the reactor based on dialysis and diffusion is still too low. The reactor made by Ambrus et. al can only reduce the concentration of phenylalanine in blood by 30% after three times of treatment in human experiments. Meanwhile, the chemical fixation of enzyme involved in such design is easy to reduce the activity of enzyme. More importantly, the reactor loaded with enzyme is very inconvenient to store and use, lacks a sterilization method suitable therefor, and has no clinical application value.

Similarly to Clara Ambrus, Allan Hoffman et al. immobilize the enzyme outside a hollow fibrous membrane with 10 kD, and the plasma is filtered through the hollow fibrous membrane and passes through the immobilized enzyme. However, the substrate quickly flows through the immobilized enzyme at one time, with a short time of reaction, low probability of contacting, and insufficient utilization rate of the enzyme. The shed enzyme directly enters the blood cycle, generating an immune reaction. Two animal experiments were forced to terminate due to the negative reaction (pupillary constriction and twitching) of the animals.

Microspheres loaded with therapeutic enzymes are stacked in a packed column in U.S. Pat. No. 3,865,726 and by Y Miura et al., and the blood is treated when passing through the packed column. However, the direct perfusion of blood to fill the microspheres would cause blockage. Microspheres loaded with enzymes are suspended by water pumps and a mechanical rotation by Robert Langer et al. (U.S. Pat. No. 5,232,696), reducing the problem of blockage. However, such a method of direct contacting and collision between blood and microspheres is easy to activate a complement effect, resulting in a serious decline in the number of white blood cells and platelets.

In the U.S. Pat. No. 4,013,564, a shunt method is adopted. Specifically, by increasing the resistance of blood flow, the plasma is promoted to enter a branch through a porous membrane, and microspheres loaded with enzymes are filtered to achieve a metabolic effect. A method combined of Taylor vortex and membrane separation is used by Robert Langer et al. First, the plasma is filtered and then the plasma mixed with microspheres loaded with enzymes, finally the treated plasma is mixed with the blood. However, unidirectional filtration of both blood and plasma will still lead to an unidirectional aggregation of microspheres loaded with enzymes, which will gradually reduce the external mass transfer and metabolic effect, and the shed enzyme will directly enter the blood cycle and generate an immune response.

Enzymes can be used to treat a variety of metabolic diseases. However, in traditional schemes of enzyme therapy, regardless of in vitro therapy or in vivo therapy, there is an immune response caused by antigen response or enzyme shedding, which is a major limitation of clinical use. Meanwhile, the stability of blood contact with enzymes is difficult to control, making the catalytic effect of enzymes difficult to control.

Herein, the fluid treatment method of the present disclosure can solve problems of enzyme shedding and antigen reaction in the body caused by the shed enzyme when it is used in the treatment of metabolic diseases. It should be understood that the fluid treatment method of the present disclosure is used through an in vitro device, so as to avoid problems of antigen reaction and drug resistance in the in vivo enzyme therapy; furthermore, compared with in vitro therapy, the fluid treatment method of the present disclosure provides a sustainable method for contacting enzymes with the to-be-treated fluid, which can be used to achieve stable contacting and control the time of reaction. Meanwhile, in the present disclosure, the enzyme as the catalytic unit can act on the target substance in a balanced cycle, the conditions of the reaction environment can be controlled to adapt to the catalytic activity of the enzyme, thereby obtaining a predictable clearance effect or catalytic effect; during the treatment process, the enzyme is intercepted in the cycle, which not only realizes the reuse of the enzyme, but also avoids the safety problems caused by the enzyme entering the downstream or blood cycle.

In in vitro therapies in the literature that have not been clinically used, the enzyme is usually in one-time contact with the liquid to be treated such as blood, with a short time of reaction, making it difficult to control the catalytic effect. In the fluid treatment method of this application, the enzyme as the catalytic unit can be kept in the cycling pipeline during the whole process and maintain contact with the target substance in the fluid, thereby increasing the probability of contact between the enzyme and the target substance and the exchange efficiency, continuous catalytic effect can be obtained. In some embodiments, the catalytic unit cycles with the fluid margin and can be evenly distributed in the pipeline, according to this method, the probability and time of contact between the catalytic unit and the substrate can be increased by extending the pipeline or increasing the volume of the pipeline.

Meanwhile, by retaining the enzyme in the pipeline, in the process of in vitro treatment, the decrease of catalytic effect caused by enzyme loss can be avoided, and the subsequent human immune response caused by enzyme shedding is also avoided. The total amount of fluid in the pipeline of the cycle module is dynamically balanced, and the cycle is therefore sustainable. The time of treatment can be determined based on the preset treatment target, thereby obtaining a controllable selective effect of clearance of the target substance in the blood.

In some embodiments provided in the first aspect of the present disclosure, the fluid treatment method is realized by at least one cycle module.

In some embodiments, the at least one cycle module further includes a first-type cycle module.

The first-type cycle module includes a pipeline, at least one separation module and at least one driving device. The pipeline includes a first section and a second section, the entrance of the first section is connected to at least one first inlet, and the exit of the second section is connected with the first section. The separation module includes a separation component that divides the separation module into a first side and a second side, where two opposite ends of the first side are respectively connected to the first section and the second section, the second side is connected to at least one outlet. The driving device is arranged at the first section, and is used to drive the fluid in the pipeline to flow cyclically to control the dynamic equilibrium of the total amount of fluid in the pipeline.

In some embodiments, the at least one cycle module includes: a pipeline, a separation module and at least one driving device, where the pipeline has an entrance and an exit; the separation module includes a separation component that divides the separation module into a first side and a second side, where two opposite ends of the first side of the separation module are respectively connected to at least one inlet and at least one outlet, and two opposite ends of the second side of the separation module are respectively connected to the entrance and exit of the pipeline; the driving device is arranged in the pipeline to drive the fluid in the pipeline to flow from the entrance to the exit at a preset flow rate, so as to achieve a dynamical balance of the total amount of fluid in the pipeline under a clinic separation mode. In the embodiment of this application, the cycle module wherein the entrance and exit of the pipeline are connected to the second side of the separation module is also called a second-type cycle module.

In the cycle module, the entrance and exit of the pipeline are connected to the corresponding two sides of the separation module, so that the pipeline and the separation module can form a cycle path together; the driving device is used to control the flow rate of fluid in the pipeline, for example, by controlling that the velocity of introducing the fluid into the cycle module is equal to the velocity of discharging the fluid from the cycle through the separation module, the total amount of fluid in the pipeline can be dynamically balanced.

The separation module contacts the fluid in the pipeline, so that the components in the fluid can selectively penetrate the separation component, the components from one side to the other side through penetrating the separation component, thereby being separated from the components that cannot penetrate the separation component, and achieving the separation effect. The separation module can be regarded as a treatment unit with a function of selective treatment for the to-be-treated fluid. In some embodiments, a catalytic unit can be further contained in the fluid. Correspondingly, the separation module can be set as a structure or material that has no permeability to the catalytic unit, so as to achieve the interception effect.

Herein, the first side and the second side of the separation module distinguish the position of the fluid that can pass through the separation component from the position of the intercepted fluid. The relationship of the position of the first side and the second side is determined by the cavity structure of the separation module and the structure of the separation component. For example, when the separation component has a planar structure and is horizontally arranged in the separation module, the first side and the second side refer to the upper side and lower side respectively; for another example, when the separation component has a planar structure and is vertically arranged in the separation module, the first side and the second side refer to the left side and right side respectively.

It should be understood that in the embodiment provided in this application, the cavity connected to the pipeline in the separation module is the first side, and other cavities in the separation module are the second side. In one embodiment, the separation module includes a plurality of cavities, for example, the separation module is separated into a plurality of cavities by a plurality of separation components in the form of a plate membrane, the cavity that connected to the pipeline is the first side, and the other cavities are the second side.

The structure or material of the separation component has a selective permeability to some specific compositions of the fluid, such as a filter, a filter membrane, and a porous metal material.

In some embodiments, the separation component is a separation membrane, some specific molecules or molecular combinations in the to-be-treated fluid can be selectively removed through the selective permeability of the separation membrane, such that the molecules or molecular combinations that cannot penetrate the separation membrane are retained in the cycle.

In some embodiments, the separation component includes a porous membrane. The porous membrane includes a microfiltration membrane, an ultrafiltration membrane, and a nanofiltration membrane. Herein, the average pore diameter or molecular weight cutoff (MWCO in short) of the porous membrane or reverse osmosis membrane is related to the target substance. In actual scenarios, the membrane suitable for intercepting the target substance is selected based on the composition of the fluid and the target substance. For example, when the size of the target substance to be intercepted in the fluid is 10 nm (i.e. 0.01 μm), the corresponding separation membrane can be a nanofiltration membrane or reverse osmosis membrane to achieve the interception for the target substance. The specific type of the separation membrane can be determined based on the difference in physical and chemical properties between each composition of the fluid and the target substance. For example, the type of the separation membrane includes: reverse osmosis membrane (average pore size 0.0001-0.001 μm), nanofiltration membrane (average pore size of 0.001-0.01 μm), ultrafiltration membrane (average pore size of 0.01-0.1 μm), microfiltration membrane (average pore size of 0.1-10 μm), electrodialysis membrane, pervaporation membrane, liquid membrane, gas separation membrane, electrode membrane, etc.

The specific type of the separation membrane can be determined based on the difference in physical and chemical properties between each composition of the fluid and the target substance. For example, the separation membrane includes: a reverse osmosis membrane (average pore size of 0.0001-0.001 μm), a nanofiltration membrane (average pore size of 0.001-0.01 μm), an ultrafiltration membrane (average pore size of 0.01-0.1 μm), a microfiltration membrane (average pore size of 0.1-10 μm), an electrodialysis membrane, a pervaporation membrane, a liquid membrane, a gas separation membrane, and an electrode membrane, etc.

In some embodiments, the separation membrane can intercept, filter or exchange the catalytic unit and the components in and fluid through steric hindrance effect, Donnan effect or electrostatic effect, adsorption, diffusion, charge repulsion effect, pore effect, or dissolution effect.

In some embodiments, especially in medical applications, the separation membrane is a high-purity polymer with inactive chemical properties and good blood compatibility and tissue compatibility.

In an embodiment, the separation component can be a porous membrane or a reverse osmosis membrane, wherein the porous membrane includes a microfiltration membrane, an ultrafiltration membrane, and a nanofiltration membrane.

In some embodiments, the average pore diameter or molecular weight cutoff (MWCO) of the separation component is related to the target substance.

In the case that the target substance needs to be retained by the separation module, the average pore size or molecular weight cutoff of the porous membrane or reverse osmosis membrane is related to the target substance. In actual scenarios, the membrane suitable for intercepting or filtering the target substance is selected based on the composition of the fluid and the target substance. For example, when the size of the target substance to be intercepted in the fluid is 10 nm (i.e. 0.01 μm), the corresponding separation membrane can be a nanofiltration membrane or reverse osmosis membrane to achieve the interception for the target substance.

In some practical applications, the pore diameter and type of the separation membrane can be determined based on a goal that expecting more than 90% of the target substance can be intercepted, or a higher goal that expecting more than 95% or even more than 99% of the target substance can be intercepted.

In some embodiments, the average pore diameter or molecular weight cutoff of the separation component is related to at least one of the catalytic unit, target substance, and target product.

In an embodiment, the cycle module may further include a catalytic unit, the average pore diameter or molecular weight cutoff of the separation component can be smaller than the particle diameter or molecular weight of the catalytic unit to intercept the catalytic unit inside the pipeline. In this embodiment, the separation component can be set according to the above-mentioned embodiment in which the treatment unit used for catalytic action in the cycle, which will not be repeated. It should be noted that in the cycle module, the separation component can further selectively permeate some specific components in the to-be-treated fluid, and the interception component can realize the interception of only the catalytic unit; meanwhile, it should be understood that the target substance retained by the separation component and the target substance that can react under the action of the catalytic unit can be the same substance or different substances.

The separation component may be a separation membrane with different geometric shapes to adapt to different fluids or achieve different filtering effects.

In some embodiments, the separation component includes one or more of a planar membrane, a tubular membrane, a roll membrane, a spiral membrane, and a hollow fiber membrane. In terms of microstructure, the separation membrane can include symmetrical membrane, asymmetrical membrane, composite membrane, multilayer composite membrane, etc.

It should be noted that the relationship of position between the first side and the second side of the separation module may be different based on the corresponding separation membranes with different geometric shapes of the separation component. For example, when the separation component is a planar membrane, the first side and the second side refer to the two opposite sides of a planar structure barrier. As another example, when the separation component is a hollow fiber membrane, the first side refers to the inside of the wall of each fibrous membrane, and the second side refers to the outside of the wall of each fibrous membrane.

The angle between the flow direction of the fluid and the separation membrane may be different, for example, the angle may be 0°-90°, when the angle between the flow direction of the fluid and the separation membrane is 0°, indicating that the fluid flows parallel to the surface of the separation membrane, such as tangential flow filtration; when the angle between the flow direction of the fluid and the separation membrane is 90°, indicating that the fluid flows in a vertical direction toward the surface of the membrane, such as dead end filtration (also called vertical filtration).

In some embodiments, a flow channel in the separation module can be set as a folded round-trip form, a spiral form or a gradual change in the size of the flow channel, for example, by folding the planar membrane to increase the area of the contact surface between the fluid and the planar membrane, and correspondingly the flow channel is set as a folded round-trip form to match the structural shape of the separation membrane, so as to ensure that the separation membrane separates the separation module into the first side and the second side.

In some embodiments, the driving device controls the fluid in the pipeline to flow at a preset flow rate, so that the catalytic unit flows from one end of the pipeline to the other end of the pipeline through the separation module.

For example, when the separation module is the TFFM (Tangential Flow Filtration Module), the flow direction of the fluid is parallel to the separation membrane in the TFFM. When the fluid passes through the separation membrane in the TFFM, a transmembrane pressure difference perpendicular to the surface of the membrane is generated on both sides of the membrane to drive the components with small molecular weight in the fluid through the separation membrane and reach the other side. The components with small molecular weight passing through the separation membrane can thereby leave the cycle, while the intercepted catalytic unit or other macromolecular components that need to be intercepted are washed away from the membrane surface driven by flowing fluid and continue to cycle in the pipeline. The pressure difference on both sides of the membrane in the TFFM is related to the preset flow rate. Besides, the intercepted substances require a certain amount of momentum to overcome the polymerization inhibition between the molecules, or between the molecules and the membrane, so as to continue the cycle. The driving device controls the flow rate of the fluid in the pipeline, thereby can be used to control the pressure difference on both sides of the separation membrane to achieve the interception and separation effects, and can be used to prevent polymerization inhibition to ensure the sustainability of cycle in the pipeline.

In some embodiments, the preset flow rate is related to at least one of the catalytic unit, composition of the fluid, temperature of the fluid, structure of the separation component, material of the separation component, cavity structure of the separation module, diameter of the pipeline, and efficiency for exchanging the fluid. The composition of the fluid includes the type of the fluid component and the corresponding concentration of each component.

The flow rate of the fluid at the separation module is related to several different parameters, for example, the flow rate of the fluid at the separation module may be changed according to the parameters including: characteristics of the fluids such as the density and viscosity of the fluid; a shape of the boundary layer of the fluid at the separation module, such as the surface shape of the separation membrane (i.e. structure of the membrane) and the cavity structure of the separation module; an interaction force between the fluid and the separation membrane, such as the surface roughness of the membrane determined by the membrane material; an attraction between the fluid and the separation membrane; and a relationship between flow rate at the separation module and at the entrance of the pipeline determined by the cavity structure of the separation module and the diameter of the pipeline. The preset flow rate can be used to determine the flow rate of the fluid at the entrance of the pipeline flowing to the separation module, a threshold value of the preset flow rate can be used as the initial flow rate at the separation module. According to the initial flow rate and the parameters mentioned above related to the flow rate of the fluid at the interception module, the fluid flow rate at the separation module can be determined by controlling the preset flow rate, resulting in a pressure difference to achieve separation, preventing intercepted macromolecular substances such as catalytic units from gathering on the surface of the membrane, thereby, macromolecular substances can flow from the entrance of the pipeline through the separation module to the exit.

In some embodiments, the preset flow rate is related to the efficiency for exchanging the target product. For example, in the TFFM, the target product needs to be driven by the pressure difference on both sides of the separation membrane after reaching a certain flow rate to flow to the other side of the separation module, thus leaving the cycle. The pressure difference is related to the flow rate, the efficiency for exchanging the target product passing through the membrane may decrease when the flow rate is too low. Therefore, the preset flow rate can also be determined by the efficiency of exchange.

The driving device is used to control the flow rate of fluid in the pipeline, so as to dynamically balance the total amount of fluid in the pipeline. Here, the first-type cycle module and the second-type cycle module can perform sustainable treatment for the fluid.

Figure 2:
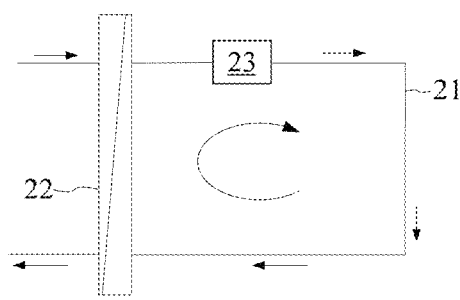
FIG. 2 shows a simplified schematic diagram of a second-type cycle module in an embodiment of the present disclosure.

Please refer to FIG. 1 and FIG. 2, where FIG. 1 shows a simplified schematic diagram of the first-type cycle module in an embodiment of the present disclosure, and FIG. 2 shows a simplified schematic diagram of the second-type cycle module in an embodiment of the present disclosure.

For the first-type cycle module, the inlet is connected to the first side of the separation module 12, and as shown in FIG. 1, the inlet is connected to the pipeline 11, the entrance and exit of the pipeline 11 are connected to the first side of the separation module 12. The intercepted treatment unit in the to-be-treated fluid is remained inside the pipeline 11, and other components can leave the cycle passing through the separation component, the specific components intercepted in the pipeline can be treated cyclically by continuing the cycle. In some embodiments, the pipeline 11 is further provided with a collecting device to accommodate the total amount of liquid for expanded cycle, which is conducive to better mixing of cycling liquid and the free treatment unit, and the collecting device can serve as an integrated platform for various liquid inlets and outlets or air inlets and outlets, and an intersection and mixing place for various liquids.

In this embodiment, a balanced state of the liquid can be maintained based on the driving device 13 to form a sustainable cycle. Meanwhile, by controlling the flow rate of fluid in the pipeline 11, the problem of a polymerization inhibition of the intercepted treatment unit on the surface of the separation component, such as the separation membrane, can be avoided.

In some embodiments, the first-type cycle module includes a catalytic unit, and the first-type cycle module forms a metabolic cycle module. In the metabolic cycle module, the catalytic unit can be immobilized or confined in a preset area of the pipeline; or the catalytic unit follows the fluid to participate the cycle, the free catalytic unit is intercepted in the cycle by the separation module traps, so that the catalytic unit can keep in contact with the to-be-treated fluid in the pipeline and avoid the loss of the catalytic unit.

In some embodiments, the cycle further includes a channel-adjusting device for adjusting the flow direction of the fluid in the pipeline. The channel-adjusting device can regulate the flow direction of fluid in the pipeline by at least one of the following ways:
  Adjusting the flow direction of the fluid by adjusting the switching state of the inlet or/and outlet of the cycle;
  Adjusting the flow direction of the fluid by adjusting the switching state of at least one adjusting channel connected to the pipeline.

In one embodiment, the inlet is provided with a pipeline switch, which switches the cycle to a mode of concentrated cycle in the closed state. The pipeline switch, for example, can be a form of a pipeline clamp, an on-off valve, a water flow switch with a sensor, etc., which is not limited in this application.

The pipeline switch is used to control the opening or closing of the inlet. When the inlet is opened, the to-be-treated fluid is continuously supplemented to the pipeline and the fluid separated by the separation module is discharged from the pipeline, so that the target substance can be enriched in the pipeline; when the inlet is closed by the pipeline switch, the fluid in the pipeline is driven by the driving device to flow to continue the cycle, and the treated fluid is discharged passing through the separation module, in this closed state, the total amount of fluid which means the concentrated cycle mode of the pipeline. In the actual applications, in the case where the target substance needs to be collected, the fluid can be treated to obtain a high concentration of the target substance under the concentrated circulation mode. For example, when platelets are the target substance, the platelet enrichment can be completed through an enrichment cycle, and the platelets can be concentrated by a concentration cycle without going through the separation process in vitro, which can avoid repeated treatment in vitro and waste of blood. The platelets obtained through the concentration cycle can be used in heart surgery, wound treatment and other applications.

In some embodiments, the concentrated cycle mode and a dilution mode can be the alternated by the first-type cycle module based on the channel-adjusting device to adjust the separation efficiency of the separation module.

Figure 5:
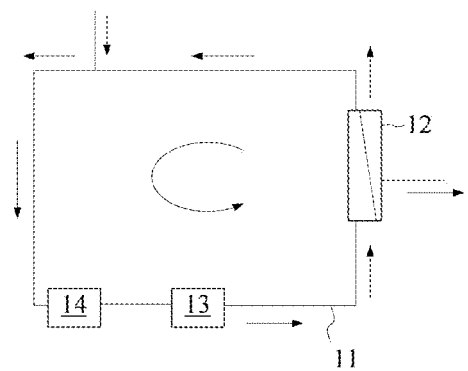
FIG. 5 shows a simplified schematic diagram of a cycle module in an embodiment of the present disclosure.

As shown in FIG. 1, in the actual applications, when the first-type cycle module is continuously in the enrichment mode to intercept the target substance, the concentration of the target substance in the pipeline 11 will increase continuously, which may lead to the reduction of the separation efficiency of the separation module 12. For example, when the separation module is a TFFM, in some optional embodiments, the pipeline 11 can be a replaceable consumable component, the fluid treatment method of the application can be implemented by replacing the pipeline 11 when the filtration efficiency drops to a certain extent. In other embodiments, refer to FIG. 5, which shows a simplified schematic diagram of the cycle module in one embodiment of the present disclosure. In the embodiment shown in FIG. 5, the flow direction of the fluid in the pipeline is adjusted by the channel-adjusting device 14 to achieve the sustainability of the pipeline, wherein the flow direction of the fluid includes the flow direction and flow channel of the fluid in the pipeline.

Figure 6A:
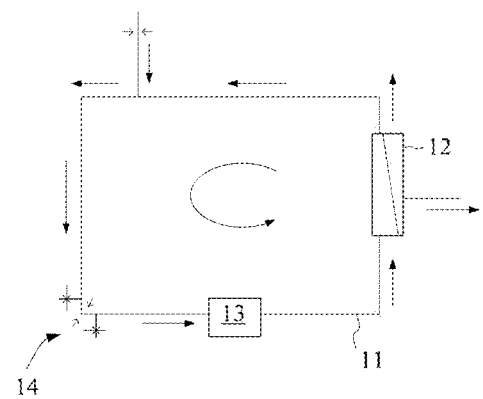
FIG. 6a to FIG. 6c show simplified schematic diagrams of a cycle module with different working states in one embodiment of the present disclosure.
Figure 6B:
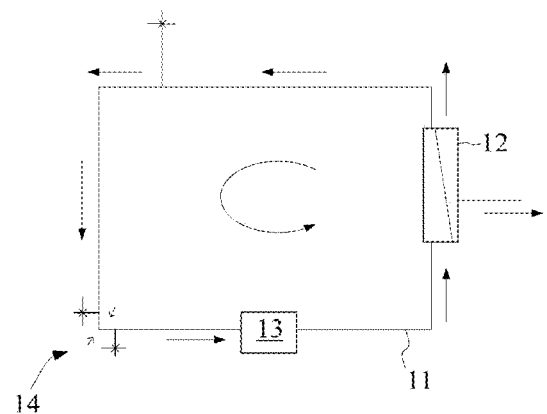
Figure 6C:
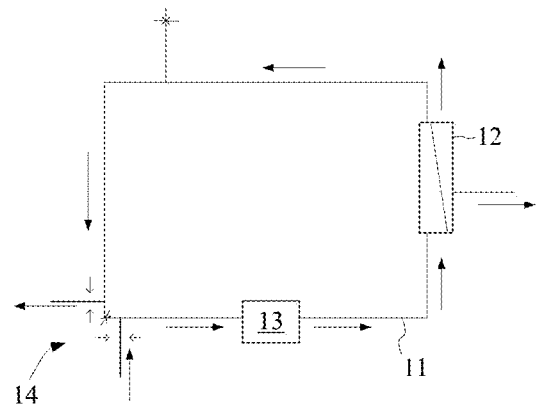

Refer to FIG. 5 and FIGS. 6a to 6c, in which FIGS. 6a to 6c are shown as simplified schematic diagrams of the pipeline 11 and the channel-adjusting device 14 under different cycle modes in one embodiment. As shown in the figures, the channel-adjusting device 14 can be a regulating pipeline and a pipeline switch that are matched with the pipeline 11, where the regulating pipeline is respectively arranged on the pipeline 11, and the pipeline switch is arranged on each regulating pipeline and the pipeline 11 between the regulating pipelines.

The cycling direction and flow channel of the fluid in the pipeline 11 can be changed by controlling the pipeline switch in the channel-adjusting device 14. For example, as shown in FIG. 6a, turn off the pipeline switch on the regulating pipeline and turn on the pipeline switch on the pipeline 11, the fluid in the pipeline 11 flows in line with the flow channel of the pipeline 11, which can be used for cyclic enrichment to collect the target substances. As shown in FIG. 6b, when the mass of the target substance intercepted in the pipeline 11 has reached a preset target, the pipeline switch of the first inlet can be turned off to make the fluid in the pipeline 11 be in the concentrated cycle mode. It should be noted that in the actual scene, the operation of concentrating and cycling the target substance obtained by enrichment is optional. In the case that a molecular concentration in the fluid has reached a preset value or the separation effect on small molecular substances in the pipeline 11 has reached the preset target after the enrichment, the operation of concentrating and cycling can be omitted. As shown in FIG. 6c, when the molecular concentration in the pipeline 11 reaches the preset value or affects the filtration effect, turn on the pipeline switch on the regulating pipeline and turn off the pipeline switch on the pipeline 11, and turn off the pipeline switch on the first inlet, with one end of the two regulating pipelines connected to the pipeline 11 and the other end serving as the entrance and exit of the pipeline 11 respectively, the two regulating pipelines cooperate with the pipeline 11 to form a new flow channel. The fluid obtained by cyclic enrichment or concentrated cycle in the pipeline 11 can be led out of the pipeline 11 through the entrance and exit, and the cleaning solution can also be introduced into the pipeline 11 to adjust the pipeline 11 into a cleaning mode. The cleaning solution can enter the pipeline 11 and the separation module 12 based on the entrance, and flow to the exit to clean the wall of pipeline 11 and the separation module 12, thereby the target substances intercepted in the pipeline 11 and the separation module 12 being removed after cleaning, the pipeline 11 and the separation module 12 can continue to be used for cyclic enrichment for the target substance in the fluid, correspondingly, the channel-adjusting device 14 can be set to a state shown in FIG. 6a to repeat the fluid treatment.

The cleaning solution is a solution without target substances, and used to remove the target substance in the pipeline 11 and the separation module 12. In some application fields, such as industrial wastewater treatment, the cleaning solution can contain a surfactant or disinfectant; in medical applications, the cleaning solution includes, for example, a physiological buffer that can participate in human blood cycle, such as a physiological saline, a phosphate buffered saline (PBS), etc.

In some embodiments, the channel-adjusting device 14 is a four-way valve. In the specific embodiments, the four-way valve can also be set as a four-way rotary valve.

Figure 7A:
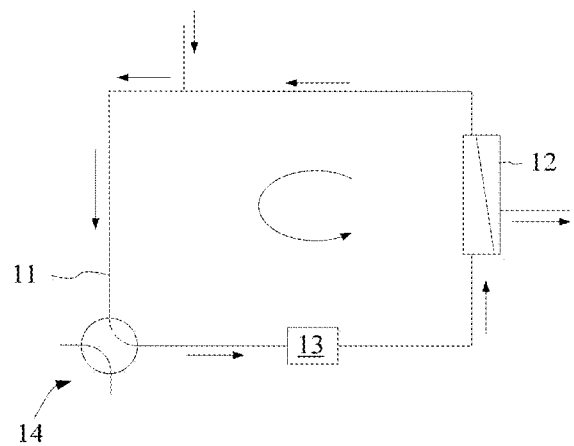
FIG. 7a to FIG. 7b show simplified schematic diagrams of a cycle module with different working states in one embodiment of the present disclosure.
Figure 7B:
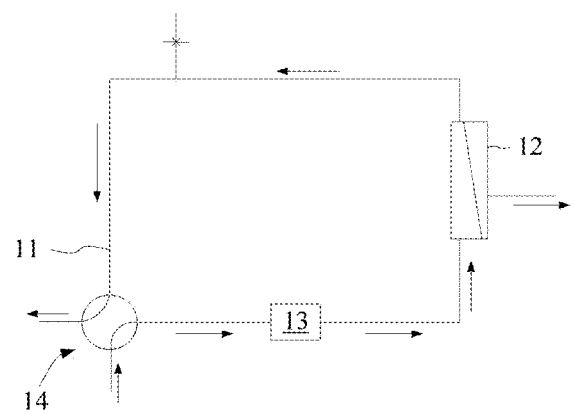

FIGS. 7a to 7b show the simplified schematic diagrams of the pipeline 11 and the channel-adjusting device 14 under different cycle modes in another embodiment. As shown in the figures, the pipeline 11 is provided with a four-way valve, which can be used to control the flow direction of fluid in the pipeline 11 by determining the connection state of different pipelines in the four-way valve. The adjustment process performed by the four-way valve is similar to the embodiments in FIGS. 6a to 6c, and will not be described again. In some embodiments, the four-way valve can also be rotated to adjust or switch different working modes in pipeline 11.

In medical applications, in order to minimize the amount of small molecular components doped in the concentrated target substance, an entrance for the cleaning solution in the channel-adjusting device 14 is turned on after concentration, inhale the physiological saline or PBS to enter the cycle, dilute the concentrated solution, then turn off the entrance for the cleaning solution, and concentrate again. After repeating the above operations for several times, most of the small molecular components remaining in the concentrated solution of the target substance can be removed. For example, red blood cells in the blood of a blood donor are directly enriched in a cycle through cyclic enrichment, and most of the proteins and small molecular components are removed through the above multiple operations of concentrating and diluting to reduce the impact of losing the proteins and small molecular components on the blood donor, and further effectively reduce the impact of allergy and pathogenic factors in the blood donor on a patient, the cleaned red blood cells can be directly introduced into the patient's body through the channel-adjusting device 14 to avoid contact with the outside.

Figure 8:
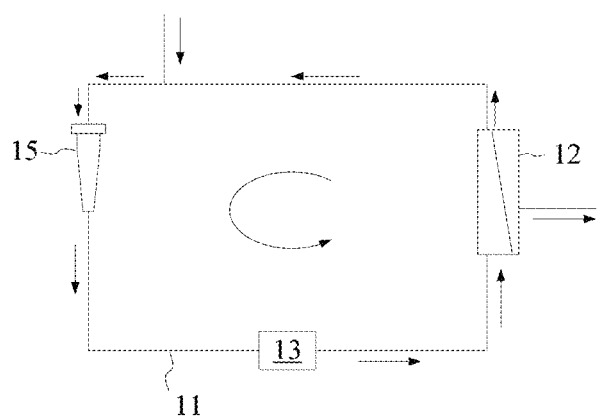
FIG. 8 shows a simplified schematic diagram of a first-type cycle module in an embodiment of the present disclosure.

FIG. 8 shows a simplified schematic diagram of the first-type cycle module in the fluid treatment method implemented as an embodiment of the present disclosure.

It should be understood that in the fluid treatment method of the present disclosure, the pipeline 11 provides space for processing or reactions in the cyclic treatment in addition to allowing the fluid to flow; in some examples, the pipeline 11 is provided with the collecting device 15 to increase the internal volume of the pipeline 11, and the collecting device 15 can be a container or storage space, such as a collecting cylinder shown in FIG. 8. Of course, the number, location, and structure of the collecting device 15 can be determined based on actual needs.

In one embodiment, the location of the collecting device 15 in the pipeline 11 is related to the location of the separation module 12; for example, in the embodiment shown in FIG. 8, the collecting device 15 is located upstream of the separation module 12, and fluid in the collecting device 15 tends to flow in the direction of the cycle due to gravity, which is designed to avoid or reduce air bubbles in the cycle. In another embodiment, the location of the collecting device 15 can be determined based on the location of an outlet of the regulating pipeline of a channel-adjusting device; for example, by setting the collecting device 15 above the outlet of the regulating pipeline, the fluid in the collecting device 15 will tend to flow to the outlet when the pipeline 11 is placed naturally. The air inlet-outlet is located in the pipeline or the air inlet is a device external to and connected to the pipeline for adjusting air pressure inside the cycle.

In some examples, the collecting device 15 can also be provided with the air inlet-outlet and the sampling port (e.g., a sample inlet). For example, the air inlet-outlet is provided in an upper part of the collecting device 15, and connects the space in the collecting device 15 not filled with fluid to the atmosphere or an external gas storage device. In some examples, the collecting device 15 can also be provide with an inlet and outlet of the regulating pipeline of the channel-adjusting device; therefore, the channel-adjusting device can be integrated into the collecting device to form a module.

In some embodiments, when the fluid treatment method is used for medical applications, a sterile filter membrane may be provided at the air inlet-outlet, for example, to ensure a sterile environment inside the cycle; similarly, when the cycle includes a sampling device, a sterile filter membrane may be provided at the corresponding sampling port.

Referring to FIG. 2, in the second-type cycle module, the inlet is connected to the first side of the separation module 22, and the entrance and exit of the pipeline 21 are connected to opposite ends of the second side of the separation module, so that the pipeline 21 and the separation module 22 can form a cycling path.

In the second-type cycle module, by using the driving device 23 to control the total amount of fluid in the pipeline 21 to be in a dynamic equilibrium, the fluid can be processed in a cyclic separation mode, to achieve sustainable cyclic separation and processing. In a specific implementation, the balance of the total amount of fluid in the pipeline 21 is achieved by controlling the fluid flow rates at the inlet and outlet to be equal.

The cyclic separation mode means that the inlet keeps introducing fluid to the separation module 22, certain components of the fluid will flow through the separation component, and then flow into the pipeline 21 connected to the second side of the separation module 22, and afterwards the certain components flow from the inlet of the pipeline 21 to the second side of the separation module 22 connected to the outlet of the pipeline 21, forming a cycle, while the outlet on the first side of the separation module 22 draws fluid out of the cycle.

Due to selective permeability of the separation component in the separation module 22 regarding the fluid components, fluid in the pipeline 21 consists of only components of the to-be-treated fluid that can permeate through the separation component, and therefore the fluid in the pipeline 21 in the second-type cycle module may also be referred to as the separated fluid in the various examples of the present disclosure.

When the outlet is connected to the first side of the separation module 22, reversible cyclic separation can be formed.

The reversible cyclic separation means that the separated fluid in the pipeline 21 can be returned to the first side of the separation module 22 following the direction of the cycle. It is easy to understand that the separation module 22 achieves separation through driving molecules across the separation component by a directional pressure difference or fluid flow, and when the pressure difference between the two sides of the separation module 22 changes, or when the flow changes its direction, the molecules that have passed through the separation component from the first side to the second side can also pass through the separation component again in order to return to the first side. That is, at the inlet of the separation module, the pressure on the first side is greater than that of the second side, forming a trans-membrane pressure, and fluid components enter the cycle through the separation module; at the outlet of the separation module, the pressure on the second side is greater than that of the first side, forming a reverse trans-membrane pressure, and the fluid components that have entered the cycle through the separation module can then leave the cycle through the separation module and enter the outlet.

Here, the separation component of the second-type cycle module may intercept some components of the to-be-treated fluid, so that only some components of the to-be-treated fluid enter the pipeline; correspondingly, the pore size or molecular weight cutoff of the separation component in the second-type cycle module may be designed based on the composition of the to-be-treated fluid, target substances, target products; in some examples, when a catalytic unit is provided in the second-type cycle module, the pore size or molecular weight cutoff of the separation component is so designed as to achieve interception of the catalytic unit. For example, in medical applications for blood purification, the first side of the separation module may be designed to intercept cellular components, such as red and white blood cells, and filter the plasma, and the second side of the separation module can be designed to intercept the cyclic catalytic unit and filter the plasma, so as to avoid direct contact of the cells with the cyclic catalytic unit.

In some embodiments, the second-type cycle module includes the catalytic unit, and the second-type cycle module forms a metabolic cycle module. In the metabolic cycle module, the catalytic unit can be immobilized or confined in a preset area of the pipeline; or the catalytic unit follows the separated fluid to participate in the cycle, in which case the free catalytic unit will be intercepted in the cycle by the second side of the separation module, so that the catalytic unit can keep in contact with the separated fluid in the pipeline and loss of the catalytic unit can be avoided. In this example, the target products generated by the separated fluid under the action of the catalytic unit can also be sent back to the first side of the separation module due to the reversible cyclic separation, in which the separated fluid is continuously introduced into the cycle and the target products are continuously discharged, thus ensuring a continuously high catalytic efficiency and a good activity stability of the catalytic unit.

In some embodiments, the fluid treatment method is realized by N cycles, and different molecules or molecular combinations in the fluid are treated by N groups of treatment units corresponding to the N cycles, so that different components in the fluid are treated respectively in the N cycles; wherein the N is a positive integer equal to or greater than 2.

Treatments performed by the N groups of treatment units can be in different categories, such as filtration of the to-be-treated fluid is realized in the first cycle, heating of the to-be-treated fluid is realized in the second cycle, and catalysis of the to-be-treated fluid is realized in the third cycle, with the cycles connected in sequence, the treatments are performed in a corresponding order.

Alternatively, the N groups of treatment units may perform the same type of treatment, but for different target substances; for example, the N groups of treatment units are all used for catalytic treatment of the to-be-treated fluid, but for different target substances; that is, in each of the N cycles, a different target substance is in contact with a different catalytic unit.

In some embodiments, fluid is introduced into N cycle modules for treatment, and the N cycle modules are connected in series or/and parallel with each other, where the N is a positive integer equal to or greater than 2 (N≥2).

Herein, the present disclosure provides Embodiment A, in which the fluid treatment method includes N cycles connected in series, where at least one of the N cycles is realized by the first-type cycle module.

Figure 11:
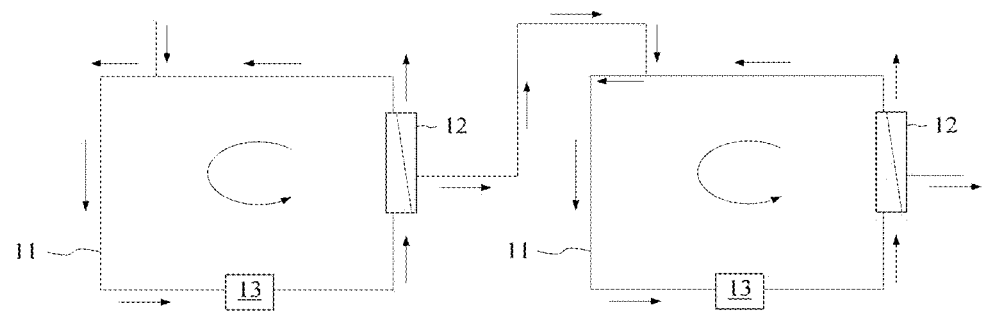
FIG. 11 shows a simplified schematic diagram of two first-type cycle modules connected in series in an embodiment.

FIG. 11 shows a simplified schematic diagram of any two adjacent first-type cycle modules in an embodiment. Herein, fluid is made to flow from an outlet of a previous cycle module to an inlet of a subsequent cycle module.

The terms "previous cycle module" and "subsequent cycle module" are used to describe any two adjacent cycle modules of the N cycle modules connected in series; "previous" and "subsequent" denote the connection order based on the flow direction of the fluid, where the fluid always flows from the previous cycle module after treatment into the subsequent cycle module for reprocessing, so that the fluid always flows from the outlet of the previous cycle module into the inlet of the subsequent cycle module.

Based on Embodiment A, the present disclosure further provides Embodiment A1, in which each of the N cycle modules connected in series is a cyclic enrichment module.

The cyclic enrichment module is a cycle module in which the target substance in the fluid is intercepted in the pipeline to enrich the target substance. In each cyclic enrichment module, the corresponding pipeline may also be referred to as an enrichment pipeline. The cycle in each cyclic enrichment module does not contain a catalytic unit.

By cascading N cyclic enrichment modules, i.e., N cyclic enrichment modules are connected in series, the fluid is processed in N cycles in the order in which the cyclic enrichment modules are connected; for each cycle treatment of each cyclic enrichment module, flow velocities or flow rates of the fluid at its inlet and outlet are equal in a cyclic enrichment mode, so that continuous enrichment of the target substance can take place in each of the cyclic enrichment modules, and the N cascaded cyclic enrichment modules are in a dynamic equilibrium in the cyclic enrichment mode, so that the enrichment process is sustainable. It should be noted that the target substances are sequentially intercepted in the cascaded enrichment pipelines in accordance with the connection order, so that fluid with different components is introduced at the inlet of each enrichment pipeline, and correspondingly target substances enriched in different enrichment pipelines can be different.

Based on Embodiment A, the present disclosure also provides Embodiment A2, in which the pipeline of at least one of the N cycles includes a catalytic unit.

In one example of Embodiment A2, the N (N≥2) cycle modules connected in series include a cyclic enrichment module and a metabolic cycle module. In the cyclic enrichment module, the enrichment of a specific component of the to-be-treated fluid is achieved, and the fluid with the specific component removed is then introduced into the metabolic cycle module.

In the N cycle modules connected in series, the separation component of the cyclic enrichment module can be used to achieve interception of the target substances to be enriched; by providing different cyclic enrichment modules with different separation components, different target substances can be enriched in different cyclic enrichment modules. In some implementations, certain components of the fluid are first enriched in the corresponding enrichment pipeline by the cyclic enrichment module, and as a result, the composition of the to-be-treated fluid introduced to the metabolic cycle module is simplified; for example, the fluid introduced to the metabolic cycle module may only include components with a molecular weight of 1500 Dalton or less. In some other implementations, the first module of the N cycle modules connected in series is a metabolic cycle module, where the target substances are catalyzed to produce the target product, and then the target product is led to the next cycle module through the separation module, so that enrichment of different components of the target product can be performed in different cyclic enrichment modules. The different target substances enriched in the cyclic enrichment module can also be adsorbed, concentrated, chemically treated, etc. by the treatment unit, so that the different components of the fluid can be collected, removed, or reacted separately according to a predefined treatment target. Due to the dynamic equilibrium of the total amount of fluid in each cycle module, the fluid treatment method is sustainable; that is, different components can be treated while no waste fluid is generated during the treatment process.

In practical applications, for example in medical applications, when the N cycle modules are connected in series for disease treatment, the to-be-treated fluid introduced to the first cycle module is, for example, blood drawn from a human body, or plasma, blood components, or other body fluid components obtained by pretreatment of the blood through the treatment unit, and when the to-be-treated fluid includes components to be enriched and target product to be generated by the action of the catalytic unit, different components of the fluid can be enriched, catalyzed or otherwise treated in different cycle modules to achieve a predetermined therapeutic effect. The concentrations of the target substances acted upon by the catalytic units in the cycle modules can be controlled by adjusting the composition of the fluid introduced to each of the different cycle modules, which can correspondingly improve or control the catalytic efficiency.

In the above mentioned medical applications, the fluid treatment method allows the in-vitro treatment (such as enrichment cycles or metabolic cycles) of human body fluids, to remove specific pathogenic factors or other components, or produce specific target components; during the in-vitro treatment, the catalytic units are trapped in the cycle modules to avoid problems such as antigenic reactions and drug resistance caused by the catalytic units remaining in the human body; due to the sustainability of the cycle modules, the duration of the treatment can also be extended according to the patient's therapeutic needs. At the same time, the fluid treatment method can be used for the treatment of patients with multiple pathogenic factors in the body, with the help of the combination of the cyclic enrichment module and the metabolic cycle module.

Furthermore, the catalytic units can be evenly distributed in the pipelines, which can solve the problem of the existing filtration method where the catalytic units such as enzymes accumulate so that the metabolic effect gradually decreases; the contact manner between the to-be-treated fluid and the catalytic units can be changed from the existing one-time contact to continuous contact, which can improve the catalytic efficiency or utilization rate of the catalytic units. At the same time, the catalytic units can be fixed in the pipelines or circulate with the fluid in the pipeline. When the catalytic units circulate with the fluid in the pipeline, they are in a cyclic motion mode, which not only avoids the aggregation of the catalytic units, but also reduces collisions between the catalytic units and other fluid molecules and/or inner walls of the pipeline, so that the catalytic units can be in a stable catalytic state.

Figure 13:
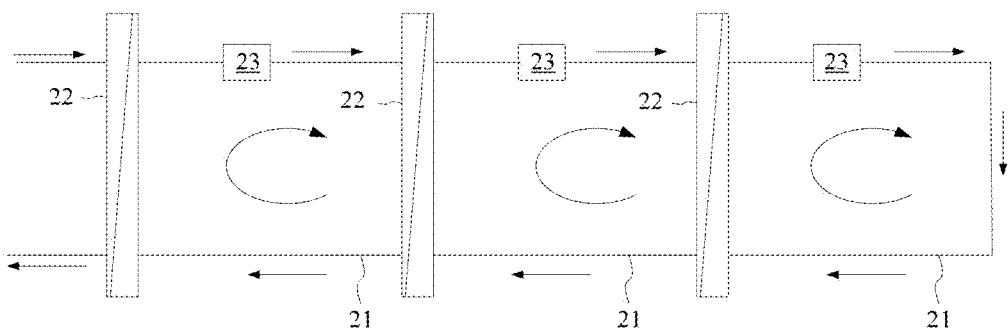
FIG. 13 shows a simplified schematic diagram of a plurality of second-type cycle modules connected in series in an embodiment.

The present disclosure also provides Embodiment B, in which the fluid treatment method includes N (N≥2) cycles connected in series, where at least one of the N cycles is realized by the second-type cycle module. Referring to FIG. 13, a simplified schematic diagram of N second-type cycle modules connected in series is shown according to Embodiment B. Each of the second-type cycle modules includes a pipeline 21, a separation module 22, and a driving device 23.

Hereinafter, the pipeline 21 in each second-type cycle module may also be referred to as a separation pipeline and fluid in the separation pipeline may also be referred to as separated fluid.

In Embodiment B, the fluid in the separation pipeline in a previous cycle module is connected to the inlet of a subsequent cycle module so that the fluid flows through N cycle modules connected in series, where N is a positive integer equal to or greater than 2. The terms "previous cycle module" and "subsequent cycle module" are used to describe any two adjacent cycle modules of the N second-type cycle modules connected in series; "previous" and "subsequent" denote the connection order based on the flow direction of the fluid, where the fluid always flows from the previous cycle module into the subsequent cycle module for reprocessing, so that the fluid always flows from the entrance of the separation pipeline of the previous cycle module to the inlet of the subsequent cycle module, and the outlet of the subsequent cycle module is connected to the exit of the separation pipeline of the previous cycle module.

Based on Embodiment B, the present disclosure further provides Embodiment B1, where the second-type cycle modules may also be referred to as cyclic separation modules, i.e., the fluid treatment method described in Embodiment B1 is implemented by N cyclic separation modules connected in series.

By connecting the N cyclic separation modules in series, N cyclic separation are performed on the fluid in accordance with the connection order; for a cycle treatment corresponding to each separation pipeline, flow velocities and flow rates of the fluid at its inlet and outlet are equal in a cyclic separation mode, i.e., the N cyclic separation modules connected in series are in a dynamic equilibrium, so that a continuous cycle of separation can be carried out in each separation pipeline. It should be noted that the target substances are sequentially intercepted in the cascaded separation pipelines in accordance with the connection order, so that fluid with different components is introduced at the inlet of each cyclic separation module, and correspondingly components of fluids in different separation pipelines can be different.

Herein, in each of the examples provided by the present disclosure, compositions of fluids may differ from each other in that they include different categories of components, and/or that concentrations or amounts of one or more components thereof are different.

Herein, the present disclosure provides embodiments for treating fluids by using N cyclic separation modules connected in series, which can be used to intercept components with different particle sizes, molecular weights, or chemical properties, or molecules with different charge properties in fluids, respectively; by providing different cyclic separation modules with different separation components, fine-grained separation of different components is achieved based on the selective permeability of the different separation modules regarding components in fluids.

In a reversible cyclic separation carried out in a second-type cycle module, reversible circulation of components is one-way reversible, i.e., components in the pipeline can return to the upstream pipeline, while components intercepted at the first side of the separation module cannot enter the downstream pipeline. For any of the second-type separation modules, a pipeline connected to the first side of the separation module is the upstream pipeline, and the separation pipeline is the downstream pipeline.

In Embodiment B1, based on the one-way reversible nature of the cycles, the fluid has increasingly fewer types of components as it flows sequentially through the N cyclic separation modules connected in series, resulting in a step-wise separation of components in the fluid. In other words, the fluid in the separation pipeline connected to the second side of a separation module contains only specific components, while the fluid in the first side of the separation module contains both the specific components and intercepted components, so that the fluid has increasingly fewer types of components as it flows sequentially through the N cyclic separation modules connected in series.

Therefore, by using the cyclic separation modules connected in series, it is possible to only treat some of all the components of the to-be-treated fluid, such as the separated fluid, while components that do not need treatment can be sent back upstream based on reversible cyclic separation of the separation pipeline. For example, as in the embodiment shown in FIG. 13, the to-be-treated fluid includes components a, b, c, d; components b, c, d are present in the first separation pipeline, and component a is intercepted at the first side of the separation module (i.e., the first separation module) corresponding to the first separation pipeline; components c, d are present in the second separation pipeline, where component b is intercepted at the first side of the separation module (i.e., the second separation module) corresponding to the second separation pipeline and can flow back to the first separation pipeline and the first side of the first separation module because of reversible cyclic separation; and the component d is present in the third separation pipeline, and the component c is intercepted at the first side of the third separation module and can flow back to the second separation pipeline and the first separation pipeline because of reversible cyclic separation; in a practical scenario, when the component d is the component to be reprocessed, the separated fluid in the third separation pipeline can be reprocessed, and the other components of the fluid, such as a, b, c, can be returned to the upstream pipeline, achieving the treatment of specific components of the to-be-treated fluid.

In some examples, in the N cyclic separation modules connected in series, the separated fluid in a separation pipeline can also be reprocessed by a treatment unit thereof, i.e., for targeted extraction, removal or other treatment of specific components of the fluid under a fine-grained separation, thereby achieving a change in concentrations of specific components of the fluid under the fine-grained separation. For example, when the molecular weight of each component in the fluid is in the range of 200 to 2000 Dalton, and N is 2, in accordance with the connection order, the previous cyclic separation module intercepts components in the fluid with a molecular weight of above 1100 Dalton, and the separated fluid in the pipeline of the previous cyclic separation module therefore includes components with a molecular weight of 200 to 1100 Dalton, and then the separation module in the subsequent cyclic separation module intercepts components with a molecular weight of above Dalton, the separated fluid in the pipeline of the subsequent cyclic separation module therefore includes components with a molecular weight ranging from 200 to 800 Dalton.

Of course, in a practical scenario, the number of the N cyclic separation modules connected in series may be any positive integer greater than 1; correspondingly, independent collecting, extracting, or processing may be performed on each of multiple components of the fluid or each of multiple classification segments of the components. The classification segments may be obtained by classifying components of the fluid based on at least one of chemical properties, molecular weights or molecular particle sizes, and charge properties of the components. It should be understood that the classification segments may be obtained by various classification criteria, and each classification segment can be obtained by using a corresponding separation module so that materials falling within the classification segment are intercepted at the first side of the separation module. For example, the separation modules are separation membranes; since different types of separation membranes have different selective permeability, by having N groups of separation membranes, the components of the fluid can be classified or intercepted for N times.

For example, in the case of fluid treatment based on N cyclic separation modules connected in series, based on molecular weights, large molecule components may be first intercepted at the first side of the separation module of the first cyclic separation module; then based on chemical properties, components with specific chemical properties are intercepted by the separation module of the second cyclic separation module; then based on charge properties, charged ions are intercepted by the separation module of the third cyclic separation module.

In a practical scenario, for example in a medical application, the N cyclic separation modules connected in series can be used, for example, to separate antibiotics, amino acids, enzymes, other proteins, etc. from the fluid.

In some embodiments, from the first cyclic separation module to the last cyclic separation module of the N cyclic separation modules connected in series, the average pore size or molecular weight cutoff of the separation component of each cyclic separation module decreases in sequence.

In this case, the components of the fluid are classified according to molecular size or molecular weight, and the separation modules of the N cyclic separation modules can be designed based on the particle sizes or molecular weights of the components of the fluid; for example, average pore sizes of the separation membranes in the N separation modules corresponding to the N cyclic separation modules decrease in sequence, or molecular weights of intercepted molecules in the N cyclic separation modules decrease in sequence, and correspondingly, molecular sizes or molecular weights of the target substances in the separation pipelines after being intercepted at the corresponding first sides of the separation modules decrease in sequence.

Based on Embodiment B, the present disclosure also provides Embodiment B2, in which at least one of the N cycles connected in series includes a metabolic cycle. A cycle comprising a catalytic unit may also be referred to as a metabolic cycle module. In this embodiment, when the catalytic unit is in the free state, the catalytic unit should be intercepted by both the separation component of the previous cycle module and that of the subsequent cycle module.

In one embodiment, each of pipelines of the N cycles connected in series is provided with a catalytic unit. Here, the fluid treatment method can be used for multiple types of treatment of different substances.

For example, a catalytic unit is intercepted in the pipeline of each cycle module; in one embodiment, each separation component is used to intercept a catalytic unit, while components of the fluid and the target product generated by the components under the action of the catalytic unit can flow through the separation component, where the target substances in the fluid can be multiple molecules or combinations of molecules, where different target substances can be separately catalyzed in different cycle modules of the N cycle modules connected in series, or the same target substances can be catalyzed several times in different cycle modules. At the same time, based on the reversible circulation of the second-type cycle module, the target substances can be returned to the upstream pipeline, and in some practical scenarios, the inlet and outlet of the first cycle module can be connected to the same container or a human circulatory system, which can realize the treatment of fluid in the container or the treatment of body fluid or body fluid components in the human circulatory system.

Further, in each cycle module, a catalytic unit is intercepted in the corresponding pipeline; in two adjacent cycle modules, the catalytic unit in the pipeline is intercepted by the separation components in the previous cycle module and in the subsequent cycle module, so that the target substances, target products and other unreacted components of the to-be-treated fluid can pass through the separation component in the subsequent cycle module to reach the pipeline in the subsequent cycle module, and then come into contact with the catalytic unit in the subsequent cycle module. In this case, the N cycle modules connected in series can be used to catalyze different components of the fluid in separate cycle modules, also to allow the obtained target products to be returned to the upstream pipeline based on the reversible nature of cycling in the second-type cycle modules.

In another scenario, the N cycle modules connected in series include a separation cycle module and a metabolic cycle module. Based on the reversible cycle formed in the separation cycle module, the fluid treatment method can be used to separate a mixture that is a complex component system in different cycle modules and to catalyze the fluid after component simplification; or, the fluid treatment method can be used to catalyze the fluid and then gradually separate the components in different cycle modules; herein, each cycle module can be selectively provided with a treatment unit, thereby achieving adsorption, removal, enrichment, electrical treatment, etc. of different components.

Thus, this application provides a solution for the selective removal of small molecules of similar molecular weight in the mode A. By means of multiple cycles, the components in the fluid are distributed in a stepwise manner in different cycle modules, and the fluid in the pipelines of different cycle modules is repeatedly reprocessed to achieve highly selective removal of specific components, catalytic reactions, or other treatments with fine-grained separation of the components.

Figure 14:
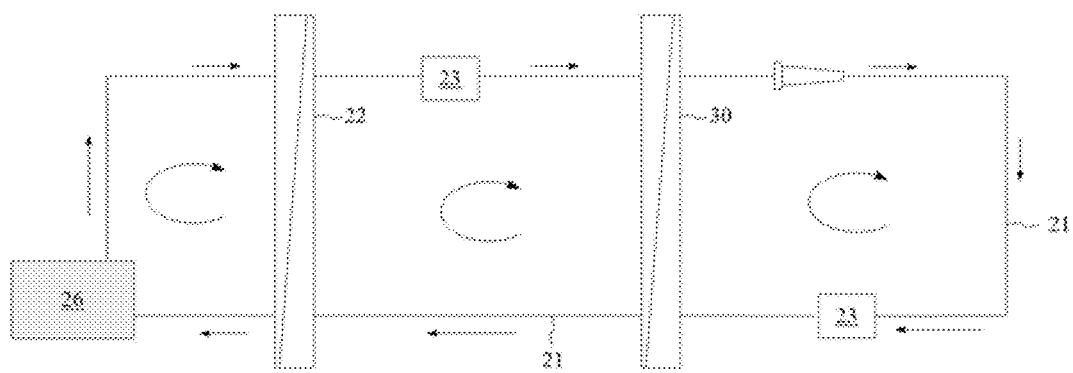
FIG. 14 shows a simplified schematic diagram of a second-type cycle module connected in series to a metabolic cycle module in another embodiment.

Refer to FIG. 14, a simplified schematic diagram is shown of an implementation of Embodiment B2 in which the N cycle modules connected in series include a metabolic cycle module and a cyclic separation module.

In the embodiment as shown in the FIG. 14, in the connection order, the two cycle modules connected in series are a cyclic separation module and a metabolic cycle module, respectively. In this case, the inlet and outlet of the cyclic separation module are connected to the container 26.

In a practical scenario, the metabolic cycle module can also be connected after a plurality of cyclic separation modules connected in series, and due to the separation of the fluid by the separation component in each cycle module, from the first to the last cyclic separation module, there are fewer and fewer types of components in the fluid; that is, components of different categories in the to-be-treated fluid can be separated gradually or in a stepwise manner to simplify the composition of the fluid, and then in the metabolic cycle module, the catalytic unit can process the mixture system obtained after the composition of the fluid is simplified.

In a practical scenario, when the to-be-treat fluid corresponding to the first cycle module is a complex mixture, such as plasma, a stepwise separation of the mixture is achieved by means of cycle modules connected in series, thereby increasing the catalytic efficiency of the catalytic unit in the metabolic cycle module.

To illustrate the technical effect that can be achieved by the N cycle modules connected in series, the following data are also provided:

Experiment 4:

The first group: based on the metabolic cycle module shown in FIG. 9, where the molecular weight cutoff of the separation module is 10 kD, 100 mL phenylalanine solution (2 mM, PBS) is added into a container connected to the inlet, the liquid in the container can be connected to the first side of the separation module through the inlet, and the fluid that can pass through the separation component can flow into the pipeline; the phenylalanine solution is driven to pre-fill the pipeline by a peristaltic pump, and the total amount of liquid in the metabolic cycle module is about 10 mL; the flow rate of the liquid at the inlet is adjusted to be equal to the flow rate of the liquid discharged from the outlet, thereby forming a balanced cycle.

After forming the balanced cycle, timing is start when 3 mL of phenylalanine ammonia lyase (about 2.84 U) is added through the sampling port, samples in the collecting device are to be tested to determine the concentration of the product of trans cinnamic acid, where the concentration of trans cinnamic acid is determined by its UV absorption peak at 280 nm, and the concentration of phenylalanine is calculated from the concentration of trans cinnamic acid.

The second group: compared to the first group, the PBS solution is replaced with 40% serum and other conditions are kept the same as in the first group.

The third group: experiments are carried out by using a plurality of cycle modules connected in series; referring to FIG. 14, which is a simplified schematic diagram of the cycling modules used in the third group, in an example, a cyclic separation module is connected in series with a metabolic cycle module, where their separation modules have molecular weight cutoffs of 50 kD and 10 kD, respectively. The cycle modules connected in series are pre-filled with 60 mL of PBS, and the flow rate is adjusted by the driving device so that the cycle modules are in equilibrium, where the amount of liquid in the cyclic separation module is about 50 mL and the amount of liquid in the metabolic cycle module is about 10 ml. In this case, the inlet and the outlet of the previous cyclic separation module are connected to the same container, into which 100 mL of serum is added to the container, into which 52 mg of phenylalanine (about 2 mM) is dissolved and equilibrated for 30 min; after that, 3 mL of PAL (about 2.84 U) is added to the metabolic cycle module through the sampling port and a sample is taken from the container; the liquid sampled from the container is diluted 10 times; 40% trichloroacetic acid is added to the diluted sample at a ratio of 1:1; and after centrifugation the concentration of the metabolite trans-cinnamic acid in the supernatant is measured directly.

Group □: Compared with Group III, the amount of liquid in the cycle separation module is about 10 mL, and the amount of liquid in the metabolic cycle module is about 50 mL, and the other conditions are consistent with Group III.

Figure 15:
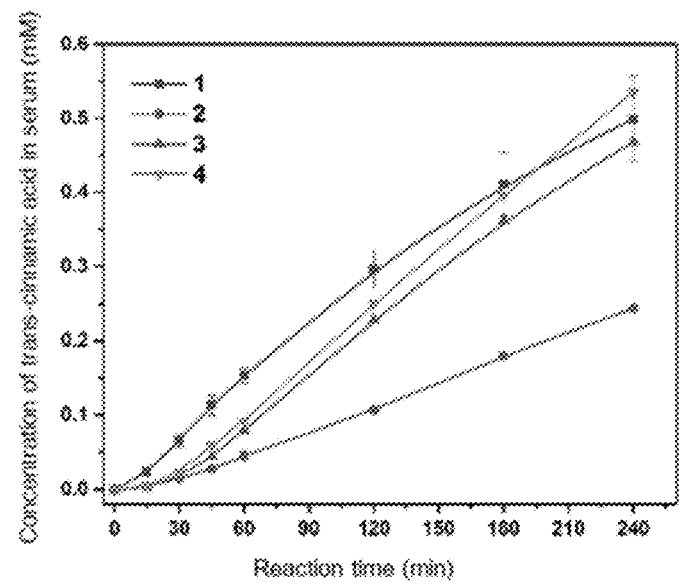
FIG. 15 shows the result of Experiment 4 of the present disclosure.

FIG. 15 shows the results of trans-cinnamic acid concentration tests corresponding to the four groups in Experiment 4, where Curves 1, 2, 3 and 4 correspond to the experimental results of Group I, Group II, Group III and Group □, respectively.

From the experimental results shown in the figure, it is clear that the metabolic cycle module alone can maintain a more stable catalytic function with sustainability when catalyzing target substances in liquids (see Curve 1). However, in complex systems, such as serum with complex components, whose protein component has a significant impact on the filtration and exchange of small molecules by 10 kD membranes, the catalytic efficiency in catalytic processes realized by the metabolic cycle module alone is reduced (see Curve 1 versus Curve 2). By combining a cycle separation module with a metabolic cycle module, i.e., by reversibly separating the components of the fluid through the cycle separation module before treatment, the present disclosure can effectively reduce the impact of components on the treatment process. For example, as shown in FIG. 14, the cycle separation module is connected in series with the metabolic cycle module to achieve a stepwise separation of the mixture during the treatment of complex systems, which reduces the impact of fluid components on the separation and exchange efficiency of small-pore membranes and thus improves the exchange efficiency and treatment results in the metabolic cycle module (see Curve 3 and Curve 4).

In some embodiments, two adjacent cycles of the plurality of cycles configured to perform the fluid treatment method of the present disclosure may also be a first-type cycle module and a second-type cycle module.

Figure 16:
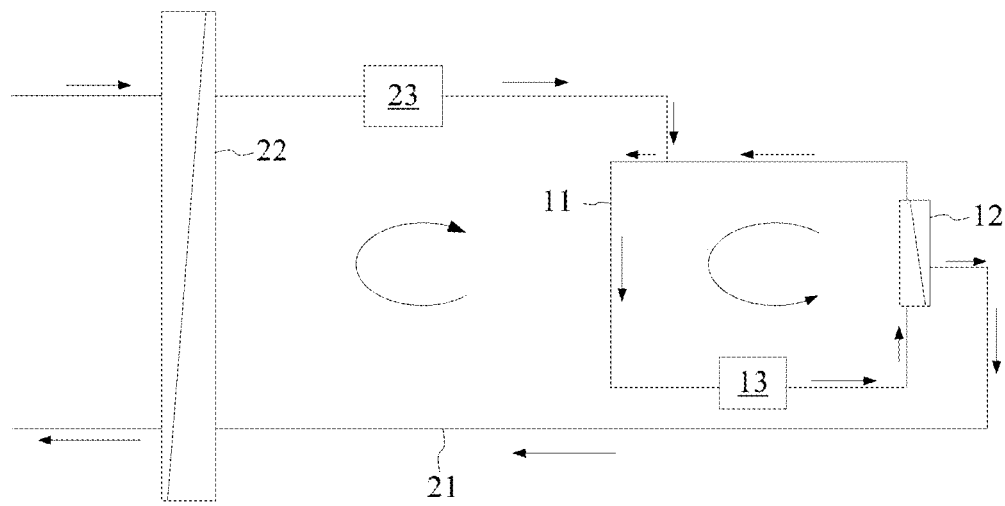
FIG. 16 shows a simplified schematic diagram of a second-type cycle module connected in series to a first-type cycle module in an embodiment.

FIG. 16 shows a simplified schematic diagram of a second-type cycle module and a first-type cycle module connected in series according to an embodiment. In this case, the pipeline 21 of the second-type cycle module is connected to the inlet and the outlet of the first-type cycle module. In this example, fluid flows from the entrance of the pipeline 21 of the second-type cycle module to the corresponding inlet of pipeline 11 of the first-type cycle module, then flows through the separation module 12 in the first-type cycle module to the outlet of the first-type cycle module; the fluid from the outlet of the first-type cycle module then flows to the exit of the pipeline 21 of the second-type cycle module to form a cycle. That is, in this example, the first-type cycle module may be considered as a sub-cycle in the second-type cycle module.

In one case, for example, in the removal of small molecule components, the components of the fluid can be separated in a stepwise manner based on one or more second-type cycle modules, with the second-type cycle module connected in a later order containing only small molecule components, and correspondingly, this second-type cycle module connected in the later order can be connected to a first-type cycle module for the enrichment of the small molecule components for removal or for the catalytic treatment of the small molecule components for their decomposition or degradation.

In one embodiment, the second-type cycle module also includes a catalytic unit, where the catalytic unit is intercepted in the corresponding cycle. In the second-type cycle module, the catalytic product of the target substance in the fluid may be connected to the inlet of the first-type cycle module. Correspondingly, the generated target products or other specific components can be enriched in the pipeline in the second-type cycle module, and the fluid from the outlet of the second-type cycle module can return to the first-type cycle module and can be reversibly circulated back to the upstream pipeline based on the first-type cycle module. This allows for the different treatment of multiple components in the fluid, such as catalytic treatment and enrichment treatment of different substances.

Alternatively, in another embodiment, the first-type cycle module also includes a catalytic unit, so that the catalytic treatment of the target product or other components of the fluid can be carried out in the first-type cycle module. This means that the same substance can be treated for several times, e.g. by catalytic treatment in the first cycle module and then catalytic treatment of the resulting product in the second cycle module, or that different components can be subjected to catalytic treatment in separate cycles. Based on the fact that the first-type cycle module includes a reversible cycle, the treated fluid can also be returned to the upstream pipeline.

In another case, following the order of connection, the two adjacent cycle modules are a first-type cycle module and a second-type cycle module. Similarly, enrichment of some components of the fluid or catalytic treatment of the target substance can be carried out in the first-type cycle module, and the fluid treated by the first-type cycle module will be introduced into the second-type cycle module for further separation treatment or catalytic treatment, which will not be repeated here.

The present disclosure further provides embodiment C, in which the fluid treatment method includes N metabolic cycles connected in series.

Figure 12:
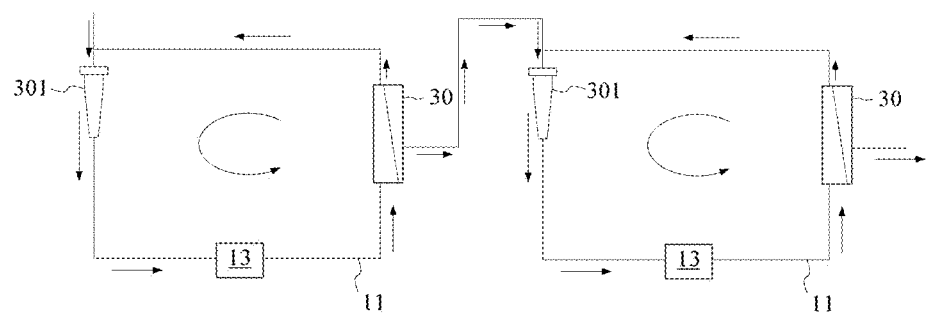
FIG. 12 shows a simplified schematic diagram of two metabolic cycle modules connected in series in another embodiment.

FIG. 12 shows a simplified schematic diagram of N metabolic cycle modules connected in series in an embodiment. Here, catalytic units may be provided in different cycles so that the structure or concentration of different target substances in different cycles can be changed, or different target products can be produced in different cycles. It is to be understood that in the case of multiple metabolic cycles connected in series, the connection of the pipeline to the interception module in the metabolic cycles is not limited to the embodiment shown in FIG. 12.

In the embodiments provided in the present disclosure, a cycle including a catalytic unit may also be referred to as a metabolic cycle. The catalytic unit may, for example, be added to the pipeline 11 of the cycle module by means of a sampling device 301.

In each cycle, the catalytic unit is fixed or limited in a preset area in the pipeline 11; or, the catalytic unit is intercepted in the pipeline 11 by the interception component to participate in the cycle. In each cycle, the corresponding to-be-treated fluid undergoes a change in concentration of the target substance or a target product is generated.

In one embodiment, the average pore diameter or molecular weight cutoff corresponding to the interception module 30 in the cycle module is designed to intercept the catalytic unit in the cycle and to divert other fluid components out of the cycle. In other words, the interception module is used to intercept the catalytic unit in the cycle and to divert the fluid treated by the catalytic unit out of the cycle. In particular, the interception of the catalytic unit by the interception component may be realized based on the chemical property, the charge characteristics, or the particle size of the fluid component, which will not be limited in this application. By retaining the catalytic unit in the cycle, the catalytic unit can achieve a continuous catalytic function and, at the same time, by causing the fluid treated by the catalytic unit to leave the cycle, the cycle can be continuously replenished with the to-be-treated fluid containing the target substance, thus ensuring the continuous catalytic effect and activity stability of the catalytic unit.

In some embodiments, different target products may be generated in different cycle modules, e.g., following the order of connection, the target product obtained by the catalytic unit in the previous cycle module can be used as the to-be-treated fluid in the next cycle module, thus being catalyzed to produce a new target product in this next cycle module.

In this case, by connecting multiple metabolic cycle modules in series, multiple target molecules in the fluid can be catalyzed or otherwise treated separately; or, multiple catalytic treatments or multiple other treatments can be applied to the same target molecule; or, multiple catalytic treatments or multiple other treatments can be applied to multiple target molecules separately. The target molecules may be molecules to be removed, degraded, decomposed, generated, or whose structure or concentration needs to be changed, including small molecules as well as biomacromolecules. In practical scenarios such as medical applications, the target molecule may be, for example, any molecule in the blood circulation, lymphatic circulation, body fluids, brain or intra-abdominal fluids, or a molecule such as alcohol that is absorbed or ingested from outside the body.

In some embodiments, the fluid treatment method is realized by N cycles, and the N cycles are connected in series with each other. Specific molecules or molecular combinations in the fluid react continuously under the action of N groups of treatment units corresponding to the N cycles; in line with the connection order of the N cycles, intermediate products generated by the action of the treatment units in the previous cycle are used as the substrates to be treated in the subsequent cycle; the N is a positive integer greater than 2.

In an example, each of the N cycles is used to realize a catalytic treatment of the to-be-treated fluid. Following the order of connection, the specific type of catalytic unit corresponding to each cycle can be preset based on the treatment target of the to-be-treated fluid. For example, the N cycles are used to achieve a cascade of catalytic reactions, i.e., the products of the previous cycle can undergo a secondary treatment or multiple treatments in the subsequent cycle. For example, in acute alcoholism applications, the catalytic unit in the first cycle is an ethanol oxidase to oxidize ethanol to produce acetaldehyde and hydrogen peroxide; the second cycle is provided with an acetaldehyde oxidase to oxidize the product of the first cycle, acetaldehyde, to acetic acid and hydrogen peroxide; and the third cycle is provided with a hydrogen peroxidase to decompose the products of the previous cycle from hydrogen peroxide to oxygen.

Herein, in embodiment C of the present disclosure, the N metabolic cycles connected in series include a first-type metabolic cycle or/and a second-type metabolic cycle.

In embodiment C, any two adjacent cycles include one of the following cases:

In one case, both adjacent cycles are first-type metabolic cycles.

In another case, both adjacent cycles are second-type metabolic cycles.

In yet another case, the adjacent two cycles are a first-type metabolic cycle and a second-type metabolic cycle.

In one example, following the order of connection, the adjacent two cycles are a second-type metabolic cycle and a first-type metabolic cycle connected to each other.

That is, in Embodiments A, B, and C, the fluid treatment method can be used to achieve separate catalytic or other treatment of one or more substance components in the fluid, multiple catalytic or multiple other treatments of the same substance component in the fluid, and separate catalytic and other treatments of different substance components in the fluid.

Herein, any of the multiple metabolic cycles connected in series can be a first-type metabolic cycle or a first-type metabolic cycle, to achieve selective treatment of the fluid in the pipeline of the cycle according to the previous embodiments. Multiple target molecules in the fluid can be catalyzed or otherwise treated separately; or, multiple catalytic or multiple other treatments can be applied to the same target molecule; or, multiple catalytic or multiple other treatments can be applied to multiple target molecules separately, which will not be repeated herein. In some scenarios, the interception component of the second-type metabolic cycle may also be used for the separation of the fluid, this means that the to-be-treated fluid in the second-type metabolic cycle may be separated and treated under the action of the interception component, and the separated and treated fluid which can pass through the interception component may enter the pipeline of the cycle for reaction under the action of the catalytic unit.

It should be noted that in the embodiments provided in the present disclosure, each cycle module may optionally include a catalytic unit; or, each cycle module may optionally include a treatment unit other than the separation module for the treatment of the fluid in the pipeline in the cycle module; or, the fluid introduced to the inlet of each cycle module or the fluid from the outlet of the cycle module may also be pretreated or reprocessed by a treatment unit. It should be understood that the above Embodiments A, B, and C show only a few types of the connection modes of different cycles and their catalytic unit settings to illustrate the fluid treatment method of the present disclosure and the beneficial effects thereof, but it is not intended to limit the cycle module performing the fluid treatment method of the present disclosure to the above Embodiments.

It should be understood that the cycle module may be used as a unit for performing the fluid treatment method of the present disclosure, and in some embodiments the fluid treatment method may be implemented by one unit alone. In embodiments including multiple units, the connection mode between the units and optional components in each unit such as the treatment unit, and optional catalytic unit, etc. may be varied. For example, the multiple cycle modules implementing the fluid treatment method of the present disclosure may also be connected in parallel, or in parallel and in series. In practice, based on the treatment target preset for the to-be-treated fluid, other connection modes and other ways of setting up catalytic units and treatment units can be used to create other compound treatment effects. In some scenarios, the cycle module performing the fluid treatment method of the present disclosure can also be coupled or integrated with other devices, apparatus, or modules to form a new device.

In some embodiments of the first aspect of the present disclosure, the fluid treatment method further includes: pre-treating or re-treating the fluid. The pre-treating or re-treating includes at least of a filtration treatment, an adsorption treatment, a heating treatment, a catalytic treatment, an enrichment treatment, a concentration treatment, a chemical treatment, an optical treatment, and an electrical treatment. Corresponding to practical applications, the pre-treating or re-treating may be realized by means of treatment modules such as adsorption devices, reactors, extraction devices, ion exchange treatment devices, filtration devices, heating devices, etc.

The treatment module pre-treats the fluid, i.e. treats the initially obtained fluid in order to introduce the treated fluid into the cycle through the inlet. The treatment module performs the pretreatment by allowing the fluid treated by the treatment module to be communicated to the inlet of the cycle. In a practical scenario, the pre-treatment may be, for example, removing impurities from the fluid by means of precipitation, centrifugal separation, or ion exchange; or, in medical applications, corresponding to plasma exchange scenarios, the pre-treatment performed by the treatment module may be, for example, the separation of the initially obtained whole blood to obtain plasma and cellular components, of which the plasma can be introduced into the cycle for further treatment.

In the present disclosure, the "communicated" means that the fluid can flow through the mechanical structures. In some occasions, the "communicated" is also often referred to as "interconnected" or "connected".

The re-treating of the fluid by the treatment module refers to treating the fluid margin in the cycle; or, the re-treating refers to treating, by the treatment module, treated fluid from the outlet of the cycle. In embodiments where the fluid treatment method is implemented by combinations of multiple cycles, the re-treating also refers to treating the fluid margin in any of the cycles, or treating treated fluid from the outlet of any of the cycles.

Here, the type of pre-treatment or re-treatment performed by the treatment module may be determined based on treatment needs. For example, when the fluid components to be filtered out are retained in the pipeline, the treatment module may concentrate the fluid leaving the cycle based on the need to purify the beneficial components of the fluid.

For example, in one embodiment, the treatment module is a separation device, through which the fluid is pretreated. The separated fluid that has passed through the separation device is introduced into the cycle for further treatment. The separation device may be used for pre-treating the fluid to remove impurities from the fluid by means of precipitation, centrifugal separation, or ion exchange; the cycle can treat the pre-treated fluid. In a practical scenario, such as a plasma exchange scenario, the initially obtained whole blood may be separated by the filter device to obtain plasma and cellular components, and target substances in the plasma may be enriched based on the cycle. When the target substance is a pathogenic factor, the filtered plasma from the second side of the separation module is pooled with the cellular components obtained from the separation of the treatment module to be returned to the human body, such that the concentration of the pathogenic factor in the plasma of the human blood circulation system is changed during this circular enrichment process.

In some embodiments of the first aspect of the present disclosure, the fluid is introduced from a storage section into the cycle for treatment, and the fluid treated by the cycle is connected to the storage section. The storage section includes a container, a storage device, a human body, or an animal body.

Figure 17:
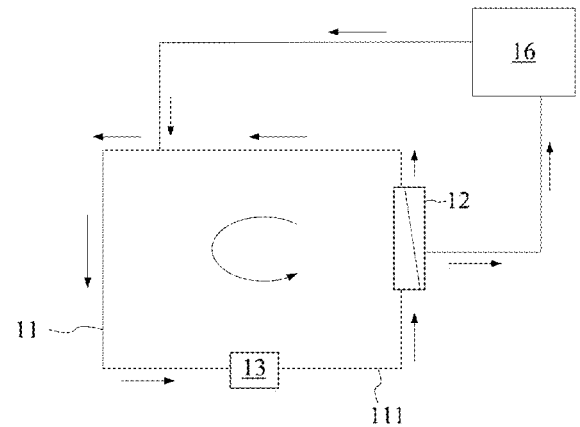
FIG. 17 shows a simplified schematic diagram of a cycle module in an embodiment of the present disclosure.

FIG. 17 shows a simplified schematic diagram of a cycle module in an embodiment. The storage section 16 may be a container or storage space, as long as it can achieve the storage or connection function of the fluid introduced to the inlet or the fluid from the outlet. In specific application scenarios, the storage section 16 may also be the blood circulation system of human or animal bodies, which will not be limited in this application.

For example, in one case, the inlet and outlet are connected to the same storage device or container. The driving device 13 controls the dynamic equilibrium of the total amount of fluid in the pipeline 11, and correspondingly, the total amount of fluid in the storage device or container is dynamically balanced. The fluid from the storage device or container is introduced into the pipeline 11 to circulate flow thereby circulating through the separation module 12 to achieve continuous separation. The separated fluid is led out of the cycle module via the separation module 12 and back to the storage device or container for continuous circulation. The target substance in the fluid in the storage device or container gradually decreases while the total amount of fluid remains unchanged. The cycle module is designed to collect the target substance in the pipeline 11 without generating waste fluid, and the circulation process can continue if the total amount of fluid in the storage device or container remains unchanged.

In another case, when the storage section 16 is a human body, the fluid can be blood, plasma, serum, tissue fluid or other body fluid of the human body. In this example, the inlet and the outlet may be directly or indirectly connected to the human body. The direct connection means that the fluid to the inlet and from the outlet may be connected to the circulatory system of the human body; the indirect connection means that a first inlet or/and a first outlet may be connected to a treatment module, and the treatment module is connected to the circulatory system of the human body. The treatment module may be used, for example, for separating the whole blood of the human body to obtain the plasma, and the inlet is connected to the separated obtained plasma. Thus, based on the fluid treatment method of the present disclosure, the plasma is introduced into and circulated in the pipeline 11 to enrich the pathogenic factor that needs to be filtered out, while the beneficial components in the plasma are continuously separated to the other side of the separation module 12 and leave the cycle following the circulation process, which avoids the generation of waste plasma in the process of enriching target substances. Thus, the problem of continuous loss of beneficial components is effectively solved by changing the concentration of target substances in human plasma based on continuous separation of the plasma from the human body.

In another case, when the pipeline 11 includes a catalytic unit, the fluid in the storage section may be continuously introduced into the cycle module, so that the target substance in the fluid can generate the target product under the action of the catalytic unit, and then the target product is led out through the separation module 12 and returned to the storage section. In this case, the permeability of the separation module 12 to the target substance may be set to retain the target substance or may be set to be permeable to the target substance. It should be understood that the target substance retained in the pipeline 11 can react with the catalytic unit upon contacting with the catalytic unit, and the target substance leaving the cycle from the separation module 12 can be reintroduced into the cycle from the inlet to contact the catalytic unit, so that a continuous catalytic effect can be achieved by fixing or retaining the catalytic unit in the pipeline 11. Correspondingly, the concentration of the target product in the storage section gradually increases and the concentration of the target substance in the storage section gradually decreases.

In the above case, when the storage section is the human body, the fluid treatment method can be used to achieve the treatment of various metabolic diseases and other diseases caused by the accumulation or deficiency of specific molecules in the human body. For example, body fluids from the human body, such as blood, can be pre-treated by means of the separation module, for instance, the whole blood may be separated into plasma components and cellular components, and then the plasma components is introduced into the cycle module. Based on the type of metabolic disease, the metabolites to be decomposed are determined. Catalytic units, such as enzymes, may be provided in the pipeline to react with the metabolites. In this case, through the cycle, the metabolites can be circularly removed from the plasma in the human body, or specific molecules lacking in the human body, such as the target products, can be generated. The sustainability based on the described cycle also allows a controlled effect on the removal of metabolites or on the generation of specific molecules, and avoids the problems of antigenic reactions, and enzyme shedding caused by enzymes in the human body.

In some embodiments of the present disclosure, the cycle further includes at least one of a control device, a storage device, a collecting device, a flow limiting device, a pressure detection device, a temperature detection device, a temperature control device, a bubble detection and elimination device, an alarm device, and a concentration detection device.

The control device may be used to control the driving device to determine the fluid flow rate in the pipeline of the cycle, or to control the pipeline switch of the inlet to determine the cycle mode of the fluid treatment in the pipeline, or to control the channel-adjusting device to determine the fluid flow direction; furthermore, the control device may also be used to receive information about the detection parameters of the fluid in the pipeline in different cycle modes for adjusting control parameters. In this way, the cycle module can form a negative feedback system. For example, the control device controls the temperature control device to perform heating or cooling based on the temperature information detected by the temperature detection device. In some examples, the temperature control device may also be a thermostat device.

The storage device may be used to store fluid from the outlet of the cycle or fluid in the pipeline of the cycle. In some examples, the storage device may also be connected to a treatment module.

The bubble detection device can be used as a control signal. For example, during a concentration cycle, bubble detection can reflect that the collecting device is close to emptying, which means that the concentrated target substance can be diluted or discharged at this time. The bubble detection device can be used as an early warning signal indicating that the equipment is not in proper working state, including, but not limited to, excessive emptying of liquid within the cycle, incorrect placement of the collection device, liquid to be treated containing bubbles or leakage of liquid, etc.

In an example, the control device determines the internal state of the pipeline based on the detection parameters and controls the control signal to the alarm device. In some embodiments, there are multiple control signals which correspond to different alarm types, for example, when the control device determines that the pressure inside the pipeline is abnormal based on the detection value of the pressure detection device, control signal a is triggered to cause the alarm device to issue an alarm corresponding to the abnormal pressure; when the control device determines that the concentration inside the pipeline reaches a preset value (which makes it impossible to continue the cycle) or the concentration is abnormal based on the detection value of the concentration detection device, a control signal b is triggered to cause the alarm device to issue an alarm corresponding to the abnormal concentration.

It should be noted that in the embodiments of the present disclosure, that the control device is provided at the pipeline means that the control device is electrically connected to the driving devices, detection devices or sensors in the pipeline, which does not restrict the location of the control device, so the control device may be located outside the pipeline. The control device can be used to obtain the working state information in the pipeline and realize the control of the working state in the pipeline.

In some embodiments, the cycle further includes a flow rate detection device for detecting the dynamic state inside the pipeline to form information for adjusting the internal working state of the pipeline.

In some embodiments, the flow rate detection device detects at least one of the flow rate at the inlet, the flow rate at the outlet, and the flow rate at the separation module, to determine the dynamic state inside the pipeline. In an example, whether the fluid inside the pipeline is in a weak dynamic state can be determined through the flow rate detection device. For example, the weak dynamic state may be a state that the flow rate of the fluid is lower than the default range or the flow rate of the filtered fluid at the outlet is significantly reduced, thus the working state of the separation module or the interception module can be determined, such as whether there is molecular obstruction, blockage, etc. in the separation module or the interception module. The flow rate detection device can thus form the adjustment information of the internal working state of the pipeline.

The adjustment information may be working mode switching information for adjusting the pipeline into a concentration cycle mode or a cleaning mode, or information for adjusting the flow rate in different areas of the pipeline.

In actual applications, the adjustment information can be formed by the control device after receiving the flow rate signal. The control device controls the channel-adjusting device and the driving device in the pipeline based on the adjustment information to adjust the internal working state of the pipeline.

In some embodiments, the adjustment information formed by the control device is formed based on at least one of the flow rate detection device, the pressure detection device, and the concentration detection device. For example, the control device comprehensively forms the adjustment information after receiving at least one of the flow rate information, the pressure information, and the fluid concentration information in the pipeline to control the channel-adjusting device, the driving device, etc. in the pipeline.

In some embodiments, the fluid treatment method is used for disease treatment by selectively removing or generating specific molecules or molecule combinations (also referred to as target molecules) that are often causative agents or consequences of disease progression or are essential for disease progression or maintenance of health. Control of the concentration of target molecules is beneficial to the treatment of diseases or the control of complications. The diseases include, but are not limited to, familial hypercholesterolemia, hyperlipoproteinemia, systemic lupus erythematosus, autoimmune diseases, myasthenia gravis, rapidly progressive glomerulonephritis, fatty liver, liver cirrhosis, acute liver failure, hyperlipidemia, severe acute pancreatitis, sepsis, Guillain-Barre syndrome, obesity, phenylketonuria, mucopolysaccharidosis, hypophosphatasia, hereditary hyperammonemia, hyperuricemia, gout, hyperglycemia, uroketosis, diabetes, and cancer.

It should be understood that the fluid treatment method achieves the therapeutic effect by changing the concentration of different molecules in the patient's body by selectively removing pathogenic agents from the patient's body fluid or by removing other molecules or molecule combinations associated with the survival of pathogenic agents, or by catalyzing specific molecules or molecule combinations to produce other target products. It should be understood that the concentration change includes the increase of a concentration from zero to a specific value, i.e., the generation of a new substance, and also includes the decrease of a concentration from a value to zero, i.e., the removal of the original substance in the body. Therefore, the fluid treatment method of the present disclosure may be used for the treatment of a variety of diseases without the limitation of the foregoing examples, and it is understood that all solutions that change the concentration of any molecule in the body through the method of the present disclosure to achieve a therapeutic effect are within the scope of the fluid treatment method.

In embodiments of the present disclosure, the treatment includes preventive, obstructive, curative or palliative treatments resulting in the desired physiological effect. In addition, the term "treatment" is used here for purposes that may partially or completely mitigate, delay the occurrence, inhibit the progression, reduce the severity, and/or reduce the incidence of one or more symptoms of a particular disease, abnormality, and/or medical condition.

In embodiments of the present disclosure, the removal is not limited to the complete removal of a component from the originally obtained fluid and is deemed to be done as long as the concentration or total amount of the component in the fluid is reduced.

In some embodiments, the fluid treatment method is used for in-vitro metabolism, and includes:
  In step S10, introducing the to-be-treated fluid from a body to selectively remove or generate specific molecules or molecular combinations;
  In step S11, returning the treated fluid to the body.

In this case, the to-be-treated fluid is any body fluid or body fluid component in human body or animal body such as blood, serum, plasma, etc. The to-be-treated fluid is treated through any of the above-mentioned embodiments provided in the first aspect of the present disclosure. At the same time, the treatment unit is intercepted in the cycle, and the treated fluid without the treatment unit is transported back to the body. A fluid treatment method for in vitro metabolism can be developed.

Compared with in vivo treatment, the fluid treatment method of the present disclosure uses in vitro metabolic treatment, which reduces the limitations of biological safety in the treatment of body fluids or body fluids components. For example, in the process of selective removal or generation of specific molecules or molecular combinations, physical methods such as high temperature or ionization can be used; agents which are toxic in vivo can be used without being introduced into the body, such as some abiotic catalysts, adsorbents, etc., as long as the related method can selectively treat the ingredients in the liquid.

The present disclosure further provides a method for acting on the human body or altering the concentration of specific molecules or molecule combinations in the human body using an enzyme or enzyme preparation.

In some embodiments, the to-be-treated fluid that is introduced from the body is treated by an enzyme or an enzyme preparation through the fluid treatment method to selectively remove or generate specific molecules or molecular combinations in the fluid and to prevent the enzyme or enzyme preparation from entering the human body or animal body, so as to control the molecular composition and concentration in the body fluid of the human body or animal body. That is, under this example, the present disclosure also provides a method for acting on the human body or altering the concentration of specific molecules or molecule combinations in the human body using an enzyme or enzyme preparation.

Figure 18A:
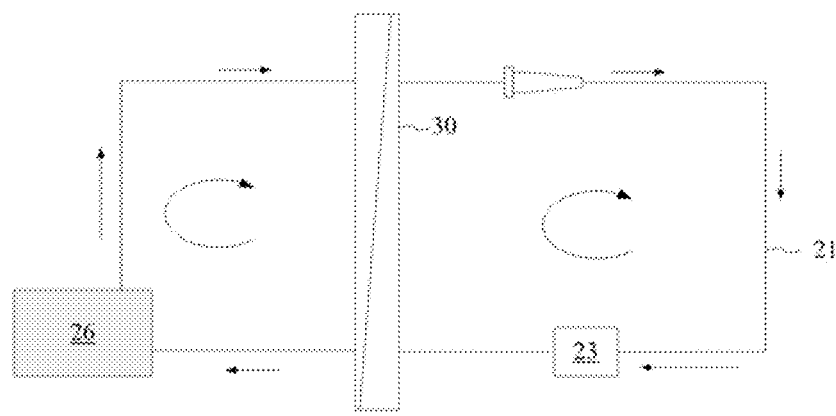
FIG. 18a shows a simplified schematic diagram of a cycle treatment system in one embodiment of the present disclosure.
Figure 18B:
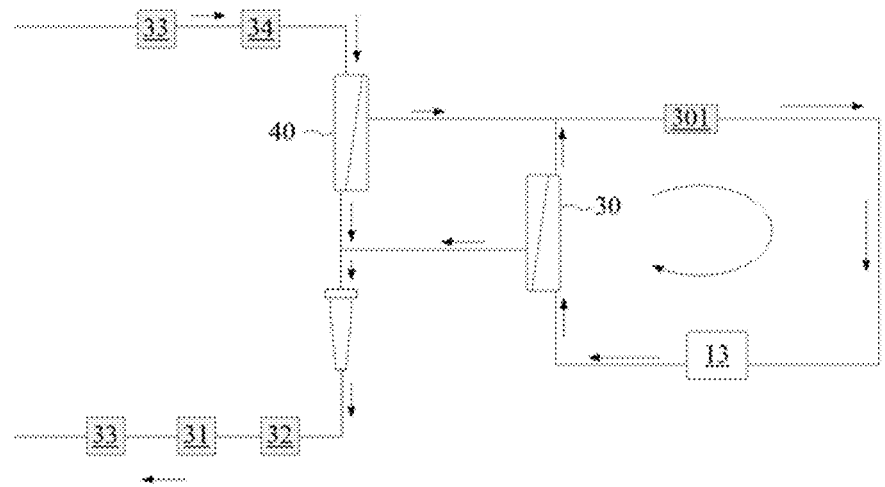
FIG. 18b shows a simplified schematic diagram of a cycle treatment system in one embodiment of the present disclosure.

FIGS. 18a and 18b show simplified schematic diagrams of an in-vitro cyclic metabolic system that can be used in various embodiments to perform the fluid treatment method for in-vitro metabolism. It should be understood that in the embodiments of the present disclosure, the cyclic metabolic system is a cycle treatment system. When a cycle treatment system acts on a human or animal body, it can be regarded as the in-vitro cyclic metabolic system.

Refer to FIGS. 18a and 18b, the in-vitro cyclic metabolic system includes a pipeline system and a cycle treatment device. The pipeline system includes a fluid-introducing pipeline and a fluid-returning pipeline.

As shown in FIG. 18a, the fluid-introducing pipeline and the fluid-returning pipeline are connected to the same storage section 26. When the fluid treatment method is used to form the in-vitro cyclic metabolic system, the storage section 26 may be a human or animal body, such as the embodiment shown in FIG. 18a. In this example, the blood or other body fluid introduced from the human body or animal body enters the cycle treatment device through the interception module 30. The cycle treatment device is used to form the second metabolic cycle module of the second-type metabolic cycle. As illustrated below in the case of blood as the to-be-treated fluid, the blood circulates in the pipeline of the second metabolic cycle module and contacts the catalytic unit to cause the target substance to be catalytically processed. At the same time, the treated blood may also be returned to the storage section 26 (i.e., the human body) through the interception module. In this example, the fluid volume in the second metabolic cycle module is controlled to be dynamically balanced so that the corresponding body fluid volume is not lost over time, thus the in-vitro metabolic process is sustainable and the metabolic time can be determined based on the processing target of the target molecules in the body. At the same time, the in-vitro cyclic metabolic system can control its efficiency of processing the target substance by adjusting the flow rate inside the metabolic cycle, as well as the flow rate of the fluid to be processed introduced from the human body, etc. The specific processing efficiency control can be referred to foregoing embodiments of the present disclosure, and will not be repeated here.

In some embodiments, the pipeline system further includes at least one of an anticoagulation system, a control device, a separated fluid storage device, a pressure detection device, a temperature detection device, a temperature control device, an oxygen detection device, a bubble detection and elimination device, an alarm device, and a concentration detection device.

The pipeline system optionally includes the above devices. It should be understood that the pipeline system is mainly used for the traction of fluid, and the above devices may be provided in the pipeline system in different application scenarios according to actual needs. For example, as shown in FIG. 18b, when the cycle treatment system is a human in-vitro cyclic device and the pipeline system is used for blood delivery, the pipeline system may usually include a bubble detection and elimination device 31, an air capture device 32, a pressure detection device 33, and an anticoagulation system 34.

In some embodiments, the anticoagulation system 34 is coupled to the pipeline system. For example, when the pipeline system is used for blood delivery, by adding coagulation-inhibiting components such as heparin, tissue plasminogen activator, antithrombin, etc. to the pipeline system, the coagulation-inhibiting components flow with the fluid in the pipeline system, which makes the pipeline system become an anticoagulation system.

The bubble detection and elimination device 31 can be used to ensure that the fluid removes air bubbles before entering the cycle treatment device, or to remove air bubbles when the treated fluid is introduced from the cycle treatment device. For example, in medical scenarios where the fluid, such as blood, needs to remove air bubbles before being returned to the human blood cycle after treatment.

The cycle treatment device is a device or module for selectively removing or generating specific molecules or molecule combinations from the to-be-treated fluid by using the fluid treatment method of the present disclosure. For example, the cycle treatment device may be a first-type cyclic module, a second-type cyclic module, a metabolic cyclic module, and a plurality of cyclic modules connected in series or in parallel, etc. In the embodiment shown in FIG. 18b, the cycle treatment device is a first metabolic cycle module formed by a first-type metabolic cycle. Optionally, the addition, replacement or renewal of the catalytic unit can be controlled through the sampling device 301.

In the scenario where the in-vitro cyclic metabolic system is used for blood processing, the raw blood or other body fluids introduced from the human body may be pretreated to suit the processing needs. For example, in the embodiment shown in FIG. 18b, the entrance where the fluid is introduced into the pipeline is connected to the whole blood introduced from the human body, and the whole blood is separated into cellular and plasma fractions under pretreatment by a treatment module 40; the plasma fractions may be connected to the inlet of the metabolic cycle module. Thereby, the target substance in the plasma fractions may contact with the catalytic unit in the metabolic cycle module and have its structure or concentration modified by the action of the catalytic unit. The catalytic unit is, for example, an enzyme, and based on the specificity of the enzyme catalysis, specific molecular components of the plasma are removed or a predetermined reaction product is generated, and the treated plasma fractions may be introduced out of the separation module and connected to the fluid-returning pipeline and pooled with the cellular fractions. In the illustrated embodiment, the plasma fractions treated by the metabolic cycle module and the cellular fractions leave the metabolic cycle through the interception module 30 and flow to the collecting device in the fluid-returning pipeline.

The total amount of fluid in the in-vitro cyclic metabolic system is kept in dynamic equilibrium and the in-vitro cyclic metabolic system is thus sustainable. In the continuous treatment process, the body fluid or body fluid components from the human or animal body can be continuously processed in the cycle treatment device, such as continuous decomposition of target substances or continuous generation of target products, or continuous enrichment of target molecules. After the body fluid or body fluid components return to the human or animal body, the concentration of the target substances or molecules in vivo can be continuously decreased, or the concentration of the target products in vivo can be gradually increased, so that the controlled removal or production of specific molecules or molecule combinations in vivo can be carried out.

Figure 19:
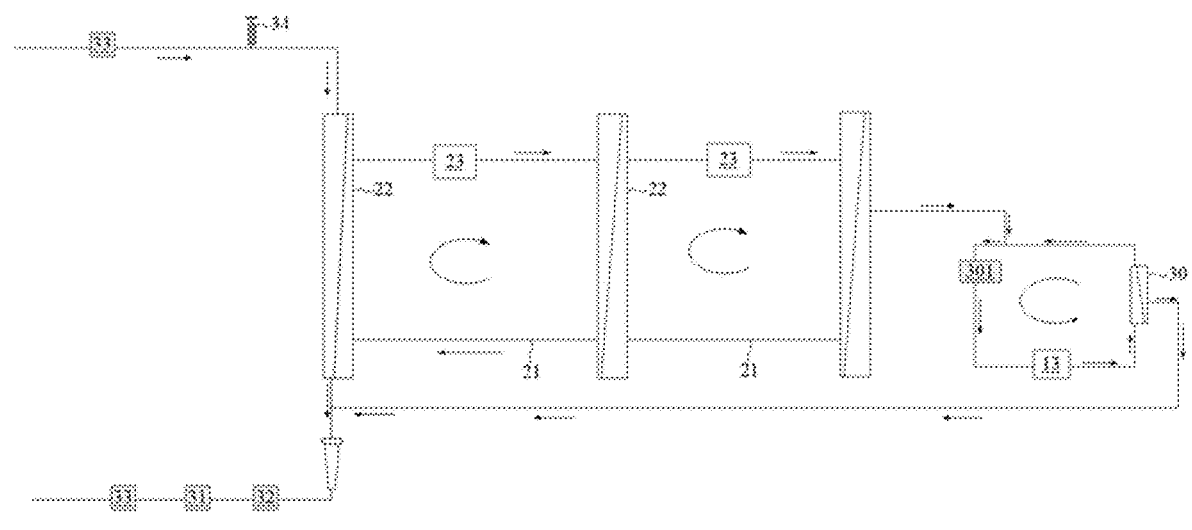
FIG. 19 shows a simplified schematic diagram of a cycle treatment system in another embodiment of the present disclosure.

FIG. 19 shows a simplified schematic diagram of an in-vitro cyclic metabolic system that can be used in another embodiment to perform the fluid treatment method for in-vitro metabolism.

Referring to FIG. 19, the in-vitro cyclic metabolic system includes a pipeline system and a cycle treatment device. The pipeline system includes a fluid-introducing pipeline and a fluid-returning pipeline.

The cycle treatment device includes multiple cycle modules connected in series. In order of connection, the multiple cycle modules are respectively a cyclic separation module, a cyclic separation module and a metabolic cycle module. In this example, the to-be-treated fluid in the fluid-introducing pipeline is connected to the inlet of the first cyclic separation module, the cyclic separation modules connected in series separate the components in the fluid in a stepwise manner, and the latter cyclic separation module is connected to a metabolic cycle module to catalyze the fluid containing only some components, including the target substance. The catalytic unit is retained in the metabolic cycle module, then the metabolic cycle module can carry out continuous catalytic treatment, and the treated fluid in the metabolic cycle module is introduced from the outlet and connected to the fluid-returning pipeline. The components not entering the metabolic cycle module can flow to the outlet of the first cyclic separation module based on the reversible nature of the cycle in the cyclic separation module, and the fluid introduced from the outlet of the first cyclic separation module and the fluid treated by the metabolic cycle module (including, for example, the target products) are connected to the fluid-returning pipeline, then can be returned to the human body by the fluid-returning pipeline. Optionally, the catalytic unit is added to the metabolic cycle module through the sampling device 301.

As shown in FIG. 19, when the cycle treatment system is a cyclic device in vitro and the pipeline system is used for blood delivery, the pipeline system may usually include an bubble detection and elimination device 31, an air capture device 32, a pressure detection device 33, and an anticoagulation system 34.

In a specific application scenario, the in-vitro cyclic metabolic system is used, for example, for blood treatment of human or animal bodies. At the separation module corresponding to the first cyclic separation module, the components in the blood such as cells and platelets are intercepted and connected through the outlet of the first cyclic separation module to a collecting device disposed at the fluid-returning pipeline. The components entering the pipeline of the first cyclic separation module, which are mainly non-cellular components, are circulated under the drive of the driving module. Molecules with medium molecular weight are exchanged at the second cyclic separation module, the molecules with medium molecular weight can flow into its pipeline through the separation module of the second cyclic separation module, and the molecules with medium molecular weight in the pipeline can be filtered at the separation module to obtain a solution including the target substance. The solution including the target substance is connected to the inlet of the metabolic cycle module, the target substance can flow into the pipeline of the metabolic cycle module and contact with the catalytic unit in the pipeline. The target substance may be decomposed or degraded by the action of the catalytic unit to reduce the concentration, or the target substance may generate a target product by the action of the catalytic unit, and the product or target product after the decomposition of the target substance may be connected to the collecting device via the interception module 30 to be pooled with components of the blood retention fluid such as the aforementioned cells and platelets.

Figure 20:
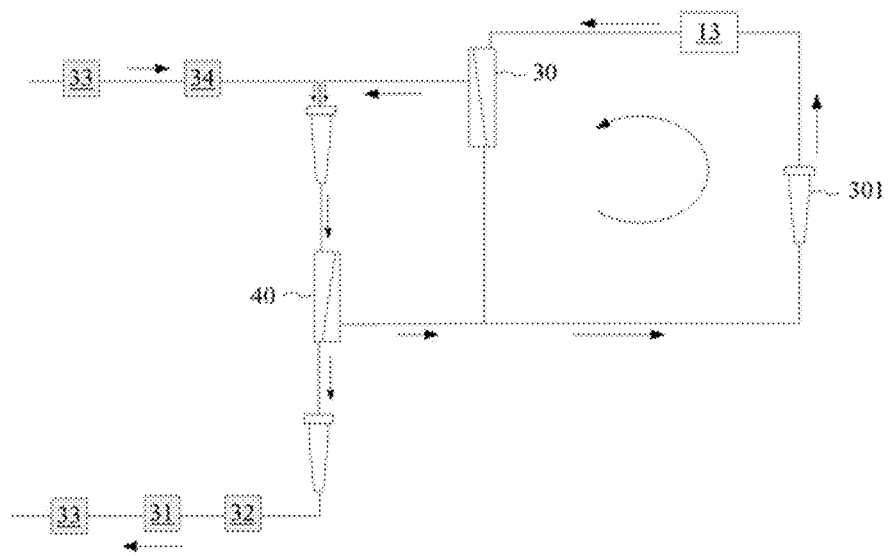
FIG. 20 shows a simplified schematic diagram of a cycle treatment system in yet another embodiment of the present disclosure.

FIG. 20 shows a simplified schematic diagram of an in-vitro cyclic metabolic system that can be used in another embodiment to perform the fluid treatment method for in-vitro metabolism.

The in-vitro cyclic metabolic system includes a pipeline system and a cycle treatment device. The pipeline system includes a fluid-introducing pipeline and a fluid-returning pipeline. In this example, the cycle treatment device is a metabolic cycle module formed by the metabolic cycle. The fluid-introducing pipeline is connected to a treatment module 40. The treatment module 40 is for example a filtering device or a separation device for separating the fluid processed by the treatment module 40 into a retained fluid and a filtered fluid. The filtered fluid being filtered or separated from the treatment module 40 is connected to the inlet of the metabolic cycle module, and the fluid processed by the metabolic cycle module is introduced from the outlet and connected to the upstream of the treatment module 40 (connected to a collecting device upstream of the treatment module 40 in FIG. 20), i.e., the fluid treated by the metabolic cycle module can be treated again by the treatment module 40, while the retained fluid at the treatment module 40 is connected to the fluid-returning pipeline.

When the in-vitro cyclic metabolic system is applied in a medical scenario, the fluid-introducing pipeline and the fluid-returning pipeline are used to introduce blood from the human body and to return the treated blood from the in-vitro cyclic metabolic system to the human body, respectively. The treatment module 40 is, for example, a filtration module for separating some components such as plasma fractions from the whole blood introduced from the human body. The plasma fractions are introduced through the pipeline to the inlet of the metabolic cycle module, and the filtered plasma treated by the metabolic cycle module is introduced from the outlet and connected to the upstream of the filtration module, thus following the flow direction, the filtered plasma is again treated by the filtration module, and the retained fluid obtained from the filtration module is renewed whole blood, and the renewed whole blood is connected to the fluid-returning pipeline for delivery to the human body. That is, in this embodiment, the plasma components can be circularly treated by the metabolic cycle module, and the treatment module 40 can also be used to achieve cyclic filtration of plasma by setting the connection mode between the metabolic cycle module and the treatment module 40.

FIGS. 18a, 18b, 19, and 20 are only several examples of the in-vitro cyclic metabolic system. In practical application, the type, number, and connection order of the cycle modules in the cycle treatment device can be changed to suit the treatment needs.

It should be understood that, in clinical application, the fluid treatment method of the present disclosure can be used to change the concentration of specific molecules or molecule combinations in the patient's body, but the medical intervention required by the patient may include other means for different disease types. For example, for patients with renal insufficiency, the fluid treatment method of the present disclosure can help achieve metabolism in vitro, to eliminate the accumulation of pathogenic factors in the patient's body. At the same time, the possible complications of renal insufficiency may include anemia, pyelonephritis, urinary tract diseases, etc. In this case, the fluid treatment method of the present disclosure can be combined with drugs and other therapeutic means, such as surgery, dietary care, etc., for disease treatment.

In some embodiments, the fluid treatment method is used for disease treatment through combination with drugs. For example, changing the concentration of specific molecules or molecule combinations in a patient's body through the fluid treatment method of the present disclosure includes: reducing the concentration of specific molecules or generating specific molecules, and at the same time, using drugs in combination with the fluid treatment method. The drugs include drugs for disease complications, anticoagulants for cardiopulmonary bypass metabolism, vasoactive drugs for the disease itself, anti-infective drugs, etc.

The first aspect of the present disclosure provides a fluid treatment method, by making the fluid flow in the pipeline to form a cycle and maintaining the dynamic equilibrium of the flow volume in the cycle to maintain the sustainability of the cycle, the fluid is treated through at least one of the cycles and the treatment unit is provided in at least one of the cycles to treat the fluid. The treatment unit is used to treat the fluid in the cycle to selectively change the structure or concentration of molecules or molecule combinations in the fluid. The fluid treatment method of the present disclosure has the following beneficial effects:

In any cycle, the sustainability of the cycle can be maintained by a dynamic equilibrium of the total amount of fluid in the cycle, so that the duration of the fluid treatment method can be determined based on a preset treatment target.

The fluid treatment method of the present disclosure can selectively change the structure or concentration of molecules or molecular combinations in the fluid through the treatment unit. Meanwhile, a controllable environment for the contact between the treatment unit and the to-be-treated fluid is constructed by forming the cycle. Thus, the present disclosure cannot only achieve highly selective treatment of the mixture system, but also adjust the efficiency, effect and the duration of the treatment method.

Based on a dynamic environment formed by the cycle, components of the fluid in the cycle change dynamically, the supplemented to-be-treated fluid can be treated continuously by the treatment unit during the treatment process, thereby the efficiency of the treatment unit can be improved. The to-be-treated fluid is better mixed and dispersed through the flowing cycle environment.

The flow rate inside the pipeline in the cycle and the flow rate of the to-be-treated fluid introduced into the cycle can be relatively independent, thus the average contact time or action time between the to-be-treated fluid and the treatment unit can be controlled by controlling the flow rate of the to-be-treated fluid introduced into the cycle, and the flow rate of the fluid inside the pipeline in the cycle can be controlled based on the processing efficiency.

In the cycle, the inlet and outlet can be connected to the same storage device or human body circulatory system, or the animal body circulatory system. In the process of treatment, the fluid treatment in the storage device or human body cycle can be maintained based on the sustainability of the cycle, and the continuous generation of waste liquid can be avoided in the process of treatment.

The cycle can be provided with a catalytic unit to achieve the removal or generation of specific target molecules. Based on the specificity of the catalytic unit, the removal or generation of specific molecules or molecular combinations in the fluid can be achieved. The continuous replenishment of the to-be-treated fluid containing the target substances in the cycle can ensure the continuous catalytic effect (efficiency) and activity stability of the catalytic unit.

At the same time, the catalytic unit can be set as a free form to participate in the cycle and be intercepted in the cycle by the separation component, which can avoid and slow down the catalytic unit from being continuously impacted and scoured by the fluid and reduce the resulted fragmentation. In embodiments where the catalytic unit is an enzyme, the protein deposition and the formation of the adhesive layer can be reduced. The fluid treatment method of the present disclosure can be used to form a dynamic environment for the reaction between the catalytic unit and the target substance within the pipeline. The catalytic unit is distributed in the pipeline in a free form, which is conducive to full contact with the target substance. Meanwhile, the catalytic unit can flow along the cycle direction driven by the cycle in the pipeline, and the catalytic unit flows tangentially along the inner wall of the pipeline, thereby the collision problem of the catalytic unit can be reduced. Through the fluid treatment method of the present disclosure, not only the target substance can be fully contacted to improve the catalytic effect, but also the probability of the catalytic unit being damaged can be reduced.

The catalytic unit is intercepted in the cycle, which can effectively avoid or reduce the loss of the catalytic unit. In specific scenarios, such as medical applications, when the catalytic unit is an enzyme, it can effectively avoid or reduce the problem of the immune response in vivo caused by enzyme shedding in traditional technology. That is, the present disclosure also provides a method for acting on the human body or altering the concentration of specific molecules or molecule combinations in the human body using an enzyme or enzyme preparation.

The fluid treatment method can realize the immediate update, replacement and supplement of the catalytic unit, which is beneficial to controlling the catalytic efficiency of the fluid treatment in practical applications, and at the same time, can effectively expand the scope of suitable storage environment of the catalytic unit; the catalytic unit and the pipeline can adopt different storage conditions respectively, thus relaxing the overall storage conditions of the equipment used to perform the fluid treatment method, and contributing to preserving activity of the catalytic unit.

By replacing and updating the catalytic unit, the activity and stability of the catalytic unit in the cycle can be ensured, or the treatment of different fluids or different target substances can be realized in the cycle module. For example, in medical applications, different types of disease treatment can be achieved by replacing a current catalytic unit with another catalytic unit.

The flow rate of the fluid in the cycle can be adjusted to control the substance exchange efficiency or filtration effect of the separation module.

When multiple cycles are employed for the fluid treatment method, the corresponding type of the cycle module, the connection mode, the specific form of the treatment unit in the cycle, and the settings of the catalytic unit are determined based on the preset treatment target, which can realize a catalytic treatment or other treatment of one or more components of the fluid, multiple catalytic treatments or other treatments of the same component in the fluid, as well as a catalytic treatment and other treatment of different material components in the fluid. Any one of the cycles is in an equilibrium state, and the multiple cycles employed for the fluid treatment method are also sustainable.

The multiple cycles enable enrichment of different components of the fluid in different cycles, or gradual separation of the fluid components in different cycles, thus achieving the removal or generation of specific components with strong selectivity, and effectively avoiding the problem of continuous loss of beneficial components in fluid treatment in the prior art. At the same time, the catalytic unit can process a mixture system obtained after the composition of the fluid is simplified due to the gradual separation of the fluid components, and the catalytic efficiency of the catalytic unit can be improved.

Based on the sustainability of the cycle, the hardware device implementing the fluid treatment method may be configured to be wearable to achieve continuous treatment of the patient in medical applications.

The second aspect of the present disclosure discloses a cycle treatment device, comprising at least one cycle module, wherein a cycle is formed by introducing a to-be-treated fluid into a pipeline of the cycle module, wherein a treated fluid is generated in the cycle and then is discharged from the cycle module, and a fluid margin is retained in the cycle module; wherein the at least one cycle module further comprises a treatment unit, the treatment unit performs treatment on the fluid in the cycle to selectively change structures or concentrations of molecules or molecular combinations in the fluid, wherein the treatment comprises at least one of a catalytic treatment, a filtration treatment, an adsorption treatment, a heating treatment, an enrichment treatment, a chemical treatment, an optical treatment, and an electrical treatment.

The cycle treatment device includes one cycle module, or a combination of two or more cycle modules. That is, the cycle treatment device of this application introduces the to-be-treated fluid into a previous cycle module, and the treated fluid will be introduced into a subsequent cycle module after leaving the previous cycle module, wherein the subsequent cycle module is adjacent to the previous cycle module, at which time the different cycle modules can be regarded as forming a series relationship. Alternatively, the fluid can be introduced into different cycle modules after being divided for parallel treatments and then collected after the treatments, in which case the different cycle modules can be regarded as forming a parallel relationship.

In some embodiments provided by the second aspect of the present disclosure, the fluid contains a target substance. The fluid includes, but is not limited to, one or more of blood, plasma, serum, body fluid, tissue fluid, cleaning fluid, dialysate, recombinant protein solution, cell culture medium, microbial culture medium, pharmaceutical and medical water, liquid medicine, fluid food, animal and plant extract, natural water, industrial wastewater, and recycled water. In some embodiments, the fluid may also be a component obtained after a fluid, such as blood, plasma, etc., has undergone treatment such as filtering. In other embodiments, the fluid may also be a mixture of gas, such as a gas mixture containing methane.

In some embodiments provided by the second aspect of the present disclosure, the cycle module further includes at least one driving device, connected to a pipeline for driving the fluid to flow to form the cycle.

In some embodiments provided by the second aspect of the present disclosure, the total amount or total velocity of the fluid introduced into the pipeline in the cycle module is equal to the total amount or total velocity of the fluid discharged from the cycle module.

In some embodiments provided by the second aspect of the present disclosure, the cycle may regulate the treatment efficiency through at least one of the following methods: controlling the ratio of the total amount of the fluid introduced into the cycle module to the total amount of the fluid in the cycle module per unit time to adjust the treatment efficiency; controlling the ratio of the total amount of the fluid discharged from the cycle module to the total amount of the fluid in the cycle module per unit time to adjust the treatment efficiency.

In some embodiments of the second aspect of the present disclosure, the treatment unit realizes a catalytic treatment by controlling a catalytic unit in the cycle, where the treatment unit controls the catalytic unit in at least one of the following ways: the treatment unit controls the type and total amount of the catalytic unit in the cycle by adding, supplementing, replacing, or updating the catalytic unit in the cycle module, and the treatment unit is configured to adjust the activity of the catalytic unit in the cycle module.

In some embodiments of the second aspect of the present disclosure, the catalytic unit is used to change the chemical structure of a target substance in the fluid to generate a target product, or to change the concentration of the target substance in the fluid.

In some embodiments of the second aspect of the present disclosure, the catalytic unit includes a biocatalytic unit and a non-biocatalytic unit, The biocatalytic unit includes at least one of a cell, a protein, an enzyme, a polypeptide, a nucleic acid, and a derivative, a conjugate, a complex, and an assembly in the form of a microsphere or microcapsule formed by at least one of the cell, protein, enzyme, polypeptide, and nucleic acid; wherein the non-biocatalytic unit includes a metal catalyst, and a derivative, a conjugate, a complex and an assembly in the form of a microsphere, or microcapsule formed based on the metal catalyst.

In some embodiments of the second aspect of the present disclosure, the catalytic unit is a cyclic catalytic unit participating in the cycle along with the fluid margin; alternatively, the catalytic unit is a fixed catalytic unit limited to or fixed in a preset area of the pipeline.

In some embodiments of the second aspect of the present disclosure, the cycle module further includes an interception module, which is arranged in the pipeline. The interception module has an interception component to intercept the cyclic catalytic unit or/and to a previously fixed catalytic unit that has detached, so as to prevent the detached catalytic unit from leaving the cycle module.

In some embodiments of the second aspect of the present disclosure, the cycle module further includes a channel-adjusting device, the channel-adjusting device is configured to regulate the flow direction of the fluid in the cycle to clean or replace the cyclic catalytic unit.

In some embodiments of the second aspect of the present disclosure, the interception component is a porous membrane or a reverse osmosis membrane, where the porous membrane includes one or more of a microfiltration membrane, an ultrafiltration membrane, and a nanofiltration membrane.

In some embodiments of the second aspect of the present disclosure, the interception component includes one or more of a plane membrane, a tubular membrane, a roll membrane, a spiral membrane, and a hollow fiber membrane.

In some embodiments of the second aspect of the present disclosure, the interception module is a tangential flow filtration (TFF) module.

In some embodiments of the second aspect of the present disclosure, the interception component separates the interception module into a first side and a second side, and the cycle includes at least one of the following: a first-type metabolic cycle module, which is located at the first side and in communication with an entrance and an exit of the pipeline, has at least one inlet communicated with the pipeline and at least one outlet communicated with the second side; a second-type metabolic cycle module, which is located at the second side and in communication with the entrance and the exit of the pipeline, has at least one inlet communicated with the first side and at least one outlet communicated with the first side.

In some embodiments of the second aspect of the present disclosure, in the first type of metabolic cycle module, the to-be-treated fluid is introduced to the cycle from the inlet and then driven by the driving device to the interception module.

In some embodiments of the second aspect of the present disclosure, the driving device controls the fluid in the pipeline to flow at a preset flow rate so that the catalytic unit flows to the pipeline through the interception module.

In some embodiments of the second aspect of the present disclosure, the preset flow rate is related to at least one of a structure of the catalytic unit, composition of the fluid, temperature of the fluid, structure of the interception component, material of the interception component, cavity structure of the interception module, diameter of the pipeline, and fluid exchange efficiency.

In some embodiments of the second aspect of the present disclosure, the average pore diameter or molecular weight cutoff of the interception component is related to at least one of the catalytic unit, the target substance, and target product.

In some embodiments of the second aspect of the present disclosure, the cycle module further includes a sampling device for adding reaction substrates, drugs, or the catalytic units to the pipeline, and for supplementing, or replacing the same.

In some embodiments of the second aspect of the present disclosure, the sampling device includes at least one sampling port communicated with the pipeline, or the sampling device is a component suitable for injection, that is, the sampling device allows for injection of samples.

In some embodiments of the second aspect of the present disclosure, the cycle module further includes a collecting device, the collecting device has a collecting chamber for mixing the cyclic catalytic unit, the fluid margin, and the liquid to be treated, so that the catalytic unit is in contact with the target substance.

In some embodiments of the second aspect of the present disclosure, the collecting device is also configured to be provided with at least one of a sampling port, an air inlet and outlet, and a liquid outlet.

In some embodiments of the second aspect of the present disclosure, the cycle module includes a pipeline, with an entrance and an exit; a separation module, including a separation component to separate the separation module into a first side and a second side, where two opposite ends of the first side of the separation module are respectively communicated with at least one inlet and at least one outlet, and the two opposite ends of the second side of the separation module are respectively communicated with the entrance and exit of the pipeline; at least one driving device, where the driving device is arranged in the pipeline to drive the fluid in the pipeline to flow from the entrance to the exit at a preset flow rate, so as to dynamically balance the total amount of the fluid in the pipeline in a cyclic separation mode.

In some embodiments of the second aspect of the present disclosure, the fluid is introduced into N cycle modules for treatment, and the N cycle modules are connected in series or/and in parallel with each other, where N is a positive integer equal to or greater than 2.

In some embodiments of the second aspect of the present disclosure, the N cycle modules are connected in series with each other; in line with the connection order, the average pore size or molecular weight cutoff of the separation components of the N cycle modules decreases one by one. That is, the N cycle modules includes at least a first cycle module, and a last cycle module, and the to-be-treated fluid is first introduced into the first cycle module; from the first cycle module to the last cycle module, the average pore size or molecular weight cutoff of the separation component of each cycle module decreases in sequence.

In some embodiments of the second aspect of the present disclosure, the separation component is a porous membrane or a reverse osmosis membrane, where the porous membrane includes one or more of a microfiltration membrane, an ultrafiltration membrane, and a nanofiltration membrane.

In some embodiments of the second aspect of the present disclosure, the separation component includes one or more of a plane membrane, a tubular membrane, a roll membrane, a spiral membrane, and a hollow fiber membrane.

In some embodiments of the second aspect of the present disclosure, the preset flow rate is related to at least one of the target substance, composition of the fluid, temperature of the fluid, structure of the separation component, material of the separation component, cavity structure of the separation module, diameter of the pipeline, and fluid exchange efficiency.

In some embodiments of the second aspect of the present disclosure, the cycle treatment device includes N cycle modules, and different molecules or molecular combinations in the fluid are treated by the N groups of treatment units corresponding to the N cycle modules, so that different components in the fluid are treated respectively in the N cycle modules; where N is a positive integer equal to or greater than 2.

In some embodiments of the second aspect of the present disclosure, the cycle treatment device includes N cycle modules, where the N cycle modules are connected in series with each other, and specific molecules or molecular combinations in the fluid perform continuous reactions under the action of N groups of treatment units corresponding to the N cycle modules; in line with the connection order of the N cycle modules, intermediate products generated by the action of the treatment units in the previous cycle module are used as substrates to be treated in the subsequent cycle module; where N is a positive integer equal to or greater than 2.

Here, for more details of the type (such as a metabolic cycle module or a cycle module including a separation module) or specific structure of each cycle module, the connection manner between adjacent cycle modules, and the treatment effect of the N cycle modules for the fluid in each example of the cycle treatment device including N cycle modules, reference can be made to the embodiments of the fluid treatment method provided by the first aspect of the present disclosure, for example, the embodiment where more than one of the first-type metabolic cycle, the second-type metabolic cycle, the first-type cycle modules, and the second-type cycle modules are cascaded, and for example, the aforementioned embodiment A, embodiment B, and embodiment C.

In some embodiments of the second aspect of the present disclosure, an inlet and an outlet of the cycle treatment device are connected to a same storage section, where the storage section includes one or more of a container, a storage device, a human body, and an animal body.

In some embodiments of the second aspect of the present disclosure, the cycle treatment device further includes at least one treatment module, the treatment module is configured to perform pre-treatment or re-treatment on the fluid in the fluid treatment device, where the pre-treatment or re-treatment includes at least one of a filtration treatment, an adsorption treatment, a heating treatment, a catalytic treatment, an enrichment treatment, a concentration treatment, a chemical treatment, an optical treatment, and an electrical treatment.

In some embodiments of the second aspect of the present disclosure, the cycle treatment device further includes at least one of a control device, a fluid storage device, a flow limiting device, a flow rate detection device, a pressure detection device, a temperature detection device, a temperature control device, an oxygen detection device, a bubble detection and elimination device, an alarm device, and a concentration detection device.

In some embodiments of the second aspect of the present disclosure, the control device provides information for adjusting the internal working state of the pipeline based on at least one of the flow rate detection device, the pressure detection device, and the concentration detection device.

In some embodiments of the second aspect of the present disclosure, the cycle treatment device is configured for disease treatment by selectively removing or generating specific molecules or molecular combinations. These specific molecules or molecular combinations (also referred to as target molecules) are often pathogenic factors or outcomes after the development of the disease, or are essential to the development of the disease or the maintenance of health. Controlling concentrations of the target molecules is conducive to the treatment of diseases or the control of the complications thereof, where the diseases includes, but are not limited to, at least one of familial hypercholesterolemia, hyperlipoproteinemia, systemic lupus erythematosus, autoimmune diseases, myasthenia gravis, rapidly progressive glomerulonephritis, fatty liver, liver cirrhosis, acute liver failure, hyperlipidemia, severe acute pancreatitis, sepsis, Guillain-Barré syndrome, obesity, phenylketonuria, mucopolysaccharidosis, hypophosphatasia, hereditary hyperammonemia, hyperuricemia, gout, hyperglycemia, uroketosis, diabetes, and cancer.

It should be understood that the fluid treatment method described in any one of the embodiments provided in the first aspect of the present disclosure can be realized by the cycle treatment device provided by the second aspect of the present disclosure. Correspondingly, the specific structure (such as the pipeline, the interception module, the separation module, the driving device, the sampling device, the treatment unit, and the like) of each cycle module in the cycle treatment device, connection manner of the cycle modules, combination mode of the cycle module and the treatment module, and the achieved fluid treatment effect are detailed in the embodiments provided in the first aspect of the present disclosure.

In some scenarios, the cycle module in the cycle treatment device is designed as an individual saleable unit. Here, the cycle treatment device can be in a form of a device that has a connection relationship, or in a form of independent components, i.e., independent cycle modules, that can be connected in a connection relationship. The connection relationship can be one or more, for example, the cycle treatment device includes multiple cycle modules, where the cycle modules can be connected in different connection relationships to meet different treatment requirements or different scene requirements, optionally only part of the components of the multiple components can be connected.

A third aspect of the present disclosure further provides a cycle treatment system, including at least one cycle treatment device as described in any embodiment in the second aspect of the present disclosure, and a pipeline system, where the pipeline system includes a fluid-introducing pipeline and a fluid-returning pipeline.

In some embodiments, the pipeline system further includes at least one of an anticoagulation system, a control device, a fluid storage device, a pressure detection device, a temperature detection device, a temperature control device, an oxygen detection device, a bubble detection and elimination device, an alarm device, a flow limiting device, and a concentration detection device.

In some embodiments, the cycle treatment system is an in vitro cyclic metabolic system, where the fluid-introducing pipeline is used to introduce the to-be-treated fluid from a body, and the fluid-returning pipeline is used to return the treated fluid to the body.

Here, the to-be-treated fluid is any body fluid or component of body fluid from a human or animal body, such as blood, serum, plasma, and the like. The to-be-treated fluid is treated by the cycle treatment device, and then the treated fluid is returned to the body.

Here, the treatment is in vitro metabolic treatment; in contrast to in vivo treatment, the cyclic metabolic system of the present disclosure have fewer limitations in the treatment of body fluids or components of body fluid imposed by biological safety concerns since it is in vitro; for example, physical methods such as high temperature or ionization can be used in the process of selectively removing or generating specific molecules or molecular combinations.

In some embodiments, in the in vitro cyclic metabolic system, an enzyme or enzyme-based product is used on the to-be-treated fluid, which is extracted from a body, to selectively remove or generate specific molecules or molecular combinations in the fluid and to prevent the enzyme or enzyme-based product from entering the human body or animal body, so as to better control the molecular composition and concentration in the body fluid of the human body or animal body. That is, in this example, the in vitro cyclic metabolic system provides a way for the enzyme or enzyme-based product to only act on or change the concentration of a specific molecule or molecular combination in the human body, without affecting the rest of the human body.

For example, the enzyme or enzyme-based product n can be used as a catalytic unit in the metabolic cycle, and the to-be-treated fluid, which is extracted from a body, is exposed to the enzyme or enzyme-based product in the in vitro metabolic system, thereby a catalytic treatment is performed to change the molecular composition and molecular concentrations. At the same time, based on the interception module in the metabolic cycle, the enzyme or enzyme-based product used as the catalytic unit is intercepted in the cycle by the interception module, thereby preventing the enzyme or enzyme preparation from entering the human or animal body.

It should be understood that the in vitro metabolic system includes the pipeline system and at least one cycle treatment device described in any one of the embodiments provided in the second aspect of the present disclosure, and as the embodiments shown in FIGS. 18a-20, the fluid treatment method for in vitro metabolism described in any one of the embodiments provided in the first aspect of the present disclosure can be realized by the in vitro metabolic system. The specific structure and connection manner of the cycle treatment device in the in vitro metabolic system are detailed in the embodiments provided by the first aspect of the present disclosure.

A fourth aspect of the present disclosure further provides a medical device, where the medical device includes the cycle treatment system according to the embodiments provided by the third aspect of the present disclosure.

The medical device may be a device used for medical purposes, may be instruments, equipment, appliances, materials or other items, which act on the human body and can be used alone or in combination, may also include required software, to realize the prevention, diagnosis, treatment, monitoring, mitigation and compensation of diseases.

In an embodiment of the present disclosure, the medical device is, for example, a blood purification device, an extracorporeal cycle clearance system, an extracorporeal enrichment clearance device, a hemodialysis device, a plasma exchange device, an extracorporeal peritoneal dialysis device, or an extracorporeal membrane oxygenation device. In other embodiments, the medical device may be a component module grafted to other extracorporeal cycle devices, such as an artificial liver, an artificial kidney, a hemodialysis device, a peritoneal dialysis device, a plasma exchange device, a plasma purification device, a blood-lipid purification device, a molecular adsorbent recirculating system, an extracorporeal membrane oxygenation device, a leukocyte depletion device, an extracorporeal cycle life support system, etc. In some embodiments, the medical device itself may act as a standalone medical machine or therapeutic device, and the medical device may also be integrated into other medical devices or machines related to the extracorporeal treatment of blood or other body fluids to form a new device.

Here, when the cycle treatment system provided by the third aspect of the present disclosure is used for medical purposes, it can be used as a medical device.

The medical purpose includes the treatment of fluids obtained on the basis of the human body, and also includes the use to obtain medicines, pharmaceutical water, medical water, etc. during treatment. For example, the cycle treatment system can be used for processing the tap water to obtain a diluted water that can be used as concentrated dialysis solution.

In some embodiments provided by the fourth aspect of this disclosure, the medical device is configured for disease treatment by selectively removing or generating specific molecules or molecular combinations. These target molecules are often pathogenic factors or outcomes of the development of diseases, or are essential to the development of diseases or the maintenance of health. Controlling concentrations of the target molecules is beneficial to the treatment of the diseases or the control of complications thereof, where the diseases include, but are not limited to, at least one of familial hypercholesterolemia, hyperlipoproteinemia, systemic lupus erythematosus, autoimmune diseases, myasthenia gravis, rapidly progressive glomerulonephritis, fatty liver, liver cirrhosis, acute liver failure, hyperlipidemia, severe acute pancreatitis, sepsis, Guillain-Barré syndrome, obesity, phenylketonuria, mucopolysaccharidosis, hypophosphatasia, hereditary hyperammonemia, hyperuricemia, gout, hyperglycemia, uroketosis, and diabetes.

It should be understood that in clinical applications, the in vitro cyclic metabolic system of this disclosure can be used to change concentrations of specific molecules or molecular combinations in the patient's body. And considering different disease types, the medical intervention required for the patient may include other means, for example, for patients with renal insufficiency, the medical device of this disclosure can achieve in vitro metabolism to eliminate the accumulated pathogenic factors in the patient's body, but at the same time, drugs and other treatment methods such as surgery, diet nursing, etc. may be used in combination with the present disclosure to deal with complications or comorbidities accompanying the renal insufficiency, such as anemia, pyelonephritis, urinary tract diseases, etc.

In certain embodiments, the medical device may be used in combination with a drug for the treatment of a disease. For example, changing the concentration of a specific molecule or combination of molecules in a patient's body through the medical device of the present disclosure, such as reducing the concentration of a specific molecule or generating a specific molecule, and at the same time, using drug therapy in combination with the medical device which is used for the patient's disease treatment; and the drug is, for example, a drug for disease complications, an anticoagulant drug for extracorporeal cyclic metabolism, a vasoactive drug for the disease itself, an anti-infective drug and other disease treatment-related drugs, as long as the treatment device described in the present disclosure and drugs can independently treat the disease or be beneficial to health, or the two can work together to realize a therapeutic effect or achieve a better therapeutic effect.

A fifth aspect of the present disclosure provides a non-transitory computer-readable storage medium for storing at least one program, wherein when the at least one program is invoked by the processor, the at least one program executes and realizes the fluid treatment method described in any one of the embodiments provided in the first aspect of the present disclosure.

If the function is implemented in the form of a software function unit and is sold or used as an individual product, it can be stored in a computer-readable storage medium. Based on the above understanding, a part of the technical solution of the present disclosure that essentially contributes to the prior art or a part of the technical solution may be in the form of a software product, which is stored in a storage medium and includes several instructions to enable a computer device (may be a personal computer, a server, or a network device, etc.) to perform all or part of the steps of the method described in the embodiments of the present disclosure.

In an embodiment provided by the present disclosure, the computer-readable storage medium may include a read-only memory, a random-access memory, an EEPROM, a CD-ROM, or other optical disk memory, a magnetic disk memory, or other magnetic storage device, a flash memory, a USB flash disk, a mobile hard disk, or any other medium that can be used to store desired program code in the form of instructions or data structures and can be accessed by a computer. In addition, any connection can be appropriately referred as a computer-readable medium. For example, if the instruction is sent from a website, a server, or other remote source using coaxial cable, optical fiber and cable, twisted-pair cable, digital subscriber line (DSL), or wireless technology such as infrared ray, radio, and microwave, then the coaxial cable, optical fiber and cable, twisted-pair cable, DSL, or wireless technology such as infrared ray, radio, and microwave are included in the definition of the medium. However, it should be understood that the computer readable and writable storage media and data storage media do not include connections, carrier waveforms, signals, or other transient media, but are intended to include non-transitory, tangible storage media. Magnetic disks and optical disks used in the present disclosure include compact disc (CD), laser disc, optical disc, digital versatile disc (DVD), floppy disc, and Blu-ray disc, in which the magnetic disks typically copy data magnetically, and the optical disks copy data optically with a laser.

In one or more exemplary aspects, the functions of the computer program for the fluid treatment method described in the first aspect of the present disclosure may be implemented in the way of hardware, software, firmware, or any combination thereof. When the functions of the computer program for the fluid treatment method is implemented in the way of software, these functions can be stored or transmitted to the computer-readable media as one or more instructions or codes. The steps of the method or algorithm disclosed in this disclosure may be embodied as a processor executable software module, where the processor executable software module may be on a tangible, non-temporary computer readable and writable storage medium. The tangible, non-temporary computer readable and writable storage media can be any available media that a computer can access.

The flowcharts and block diagrams in the above-mentioned drawings of the present disclosure illustrate the architectures, functions, and operations of possible implementations of systems, methods, and computer program products in accordance with various embodiments of the present disclosure. Each box in the flowchart or block diagram may represent a module, a program segment, or a part of codes that contains one or more executable instructions for implementing the specified logical function. It should be noted that in some alternative implementations, the functions marked in the box can also be achieved in a different order other than those marked in the drawings. For example, two boxes represented in succession can actually be executed substantially in parallel, and depending on the function involved, they can sometimes be executed in reverse order. It should also be noted that each box in the block diagram and/or flow chart, as well as the combination of the boxes in the block diagram and/or flow chart, can be implemented by a dedicated hardware-based system that performs specified functions or operations, or can be implemented by a combination of dedicated hardware and computer instructions.

The above embodiments only illustrate the principles and efficacy of the present disclosure, and are not intended to limit the disclosure. Those skilled can make modifications or changes to the above-mentioned embodiments without going against the spirit and the scope of the present disclosure. Therefore, all equivalent modifications or changes made by those who have common knowledge in the art without departing from the spirit and technical concept disclosed by the present disclosure shall be still covered by the claims of the present disclosure.

What is claimed is:

1. A fluid treatment method, comprising:
introducing a to-be-treated fluid into a pipeline to flow to form a cycle; wherein the fluid in the cycle is driven by at least one driving device connected to the pipeline;
discharging a treated fluid from the cycle, and retaining a fluid margin in the cycle;
a total amount or total velocity of the to-be-treated fluid introduced into the pipeline is equal to that of the treated fluid discharged from the cycle, so that a total amount of fluid in the pipeline is in a state of dynamical equilibrium;
wherein the fluid treatment method is carried out by at least one cycle, the at least one cycle further comprises a catalytic unit, the catalytic unit catalyzes the fluid in the cycle to change a structure of a target substance in the fluid and generate a target product; or the catalytic unit changes a concentration of the target substance; the catalytic unit is a cyclic catalytic unit participating in the cycle along with the fluid margin; the catalytic unit comprises a biocatalytic unit and a non-biocatalytic unit;
the cycle further comprises an interception module arranged in the pipeline, the interception module is a tangential flow filtration (TFF) module, the interception module has an interception component to intercept the cyclic catalytic unit to prevent it from leaving the cycle; the driving device controls the fluid in the pipeline to flow at a preset flow rate so that the catalytic unit flows to the pipeline through the interception module; the interception component divides the interception module into a first side and a second side, and the cycle comprises at least one of the following:
a first-type metabolic cycle, wherein an entrance and an exit of the pipeline are connected to the first side of the interception module, and the first-type metabolic cycle has at least one inlet connected to the pipeline and at least one outlet connected to the second side of the interception module; and
a second-type metabolic cycle, wherein an entrance and an exit of the pipeline are connected to the second side of the interception module, and the second-type metabolic cycle has at least one inlet connected to the first side and at least one outlet connected to the first side of the interception module.

2. The fluid treatment method according to claim 1, treatment efficiency of the cycle is adjusted by at least one of the following ways:
controlling the ratio of a total amount of the to-be-treated fluid introduced into the pipeline to a total amount of the fluid in the cycle per unit time; and
controlling the ratio of a total amount of the treated fluid discharged from the pipeline to the total amount of the fluid in the cycle per unit time.

3. The fluid treatment method according to claim 1, wherein a treatment unit controls the catalytic unit in at least one of the following ways:
the treatment unit controls a type and total amount of the catalytic unit in the cycle by adding, supplementing, or replacing the catalytic unit;
the treatment unit is configured to adjust activity of the catalytic unit in the cycle.

4. The fluid treatment method according to claim 3, wherein the biocatalytic unit is selected from the group consisting of:

a cell, a protein, an enzyme, a polypeptide, a nucleic acid, and a derivative, a complex, and an assembly in the form of a microsphere or microcapsule formed by at least one of the cell, protein, enzyme, polypeptide, and nucleic acid; and wherein the non-biocatalytic unit is selected from the group consisting of:

a metal catalyst, and a derivative, a complex and an assembly in the form of a microsphere or microcapsule formed based on the metal catalyst.

5. The fluid treatment method according to claim 1, wherein the cycle is provided with a channel-adjusting device, and the channel-adjusting device is configured to regulate a flow direction of the fluid in the cycle to clean or replace the cyclic catalytic unit.

6. The fluid treatment method according to claim 1, wherein the interception component is a porous membrane or a reverse osmosis membrane, wherein the porous membrane is selected from the group consisting of a microfiltration membrane, an ultrafiltration membrane, and a nanofiltration membrane.

7. The fluid treatment method according to claim 1, wherein the interception component is selected from the group consisting of a planar membrane, a tubular membrane, a roll membrane, and a hollow fiber membrane.

8. The fluid treatment method according to claim 1, wherein in the first-type metabolic cycle, the to-be-treated fluid is driven to the interception module by the driving device after being introduced into the cycle.

9. The fluid treatment method according to claim 1, wherein the preset flow rate is related to at least one of a structure of the catalytic unit, a composition of the fluid, a temperature of the fluid, a structure of the interception component, a material of the interception component, a cavity structure of the interception module, a diameter of the pipeline, and a fluid exchange efficiency.

10. The fluid treatment method according to claim 1, wherein an average pore diameter or molecular weight cutoff of the interception component is related to at least one of the catalytic unit, the target substance, and the target product.

11. The fluid treatment method according to claim 1, wherein the cycle is provided with a sampling device for adding reaction substrates, drugs, or catalytic units to the pipeline, or supplementing or replacing of the same.

12. The fluid treatment method according to claim 11, wherein the sampling device comprises at least one sample inlet connected to the pipeline, or the sampling device is a component allowing for injection of samples.

13. The fluid treatment method according to claim 1, wherein the cycle module is equipped with a collecting device, and the collecting device has a collecting chamber for mixing the cyclic catalytic unit, the fluid margin, and the to-be-treated liquid to bring the catalytic unit into contact with the target substance.

14. The fluid treatment method according to claim 13, wherein the collecting device is further provided with at least one of a sample inlet, an air inlet, and a liquid outlet.

15. The fluid treatment method according to claim 1, wherein the fluid is introduced into a cycle module to form the cycle, wherein the cycle module comprises:

a pipeline, with an entrance and an exit;

a separation module, comprising a separation component that divides the separation module into a first side and a second side, wherein two opposite ends of the first side of the separation module are respectively connected to at least one inlet and at least one outlet, and two opposite ends of the second side of the separation module are respectively connected to the entrance and exit of the pipeline; and at least one driving device, wherein the driving device is arranged in the pipeline to drive the fluid in the pipeline to flow from the entrance to the exit at a preset flow rate, so as to dynamically balance the total amount of the fluid in the pipeline in a cyclic separation mode.

16. The fluid treatment method according to claim 15, further comprising: introducing the fluid into N cycle modules for treatment, wherein the N cycle modules are connected in series or parallel with each other, wherein the N is a positive integer equal to or greater than 2.

17. The fluid treatment method according to claim 16, wherein the N cycle modules are connected in series with each other; according to the connection order, the average pore size or molecular weight cutoff of the separation component of each cyclic separation module decreases in sequence.

18. The fluid treatment method according to claim 15, wherein the separation component is a porous membrane or a reverse osmosis membrane, wherein the porous membrane is selected from the group consisting of a microfiltration membrane, an ultrafiltration membrane, and a nanofiltration membrane.

19. The fluid treatment method according to claim 15, wherein the separation component is selected from the group consisting of a planar membrane, a tubular membrane, a roll membrane, and a hollow fiber membrane.

20. The fluid treatment method according to claim 15, the preset flow rate is related to at least one of the target substance, a composition of the fluid, a temperature of the fluid, a structure of the separation component, a material of the separation component, a cavity structure of the separation module, a diameter of the pipeline, and a fluid exchange efficiency.

21. The fluid treatment method according to claim 1, wherein the fluid treatment method is realized by N cycles, and different molecules or molecular combinations in the fluid are treated by N treatment units corresponding to the N cycles, so that different components in the fluid are treated respectively in the N cycles; wherein N is a positive integer equal to or greater than 2.

22. The fluid treatment method according to claim 1, wherein the fluid treatment method is realized by N cycles, wherein the N cycles are connected in series with each other, and specific molecules or molecular combinations in the fluid react continuously under the action of N treatment units corresponding to the N cycles; according to the connection order of the N cycles, intermediate products generated by the action of the treatment unit in a previous cycle are used as substrates to be treated in a subsequent cycle, wherein the previous cycle and the subsequent cycle are two adjacent cycles of the N cycles connected in series; wherein the N is a positive integer equal to or greater than 2.

23. The fluid treatment method according to claim 1, wherein the fluid contains a target substance, the fluid is selected from the group consisting of cleaning fluid, dialysate, recombinant protein solution, cell culture medium, microbial culture medium, fluid food, animal and plant extract, natural water, industrial wastewater, and recycled water.

24. The fluid treatment method according to claim 1, wherein the fluid is introduced from a storage section into the at least one cycle for treatment, and the fluid treated by the at least one cycle is connected to the storage section, wherein the storage section comprises a storage device.

25. The fluid treatment method according to claim 1, further comprising: performing pretreatment or retreatment on the fluid by at least one treatment module, wherein the pretreatment or retreatment is selected from the group consisting of a filtration treatment, an adsorption treatment, a heating treatment, a catalytic treatment, an enrichment treatment, a concentration treatment, an optical treatment, and an electrical treatment.

26. The fluid treatment method according to claim 1, wherein the cycle is selected from the group consisting of a control device, a fluid storage device, a flow limiting device, a flow rate detection device, a pressure detection device, a temperature detection device, a temperature control device, an oxygen detection device, a bubble detection and elimination device, an alarm device, and a concentration detection device.

27. The fluid treatment method according to claim 26, wherein the control device forms an information for adjusting an internal working state of the pipeline based on the flow rate detection device, or the pressure detection device, or the concentration detection device.

28. A cycle treatment device, comprising at least one cycle module, wherein a cycle is formed by introducing a to-be-treated fluid into a pipeline of the cycle module, wherein a treated fluid is generated in the cycle and then is discharged from the cycle module, and a fluid margin is retained in the cycle module; wherein the at least one cycle module further comprises a catalytic unit, the catalytic unit is configured to catalyze the fluid in the cycle to change a structure of a target substance in the fluid and generate a target product; or the catalytic unit is configured to change a concentration of the target substance; the catalytic unit is a cyclic catalytic unit participating in the cycle along with the fluid margin; the catalytic unit comprises a biocatalytic unit and a non-biocatalytic unit;
 wherein a total amount or total velocity of the fluid introduced into the pipeline is equal to that of the treated fluid when discharged from the cycle module; wherein the cycle module further comprises at least one driving device connected to the pipeline for driving the fluid to flow to form the cycle;
 wherein the cycle further comprises an interception module, and the interception module is arranged in the pipeline, and has an interception component to intercept the cyclic catalytic unit to prevent it from leaving the cycle module; wherein the driving device controls the fluid in the pipeline to flow at a preset flow rate so that the catalytic unit flows to the pipeline through the interception module; wherein the interception module is a TFF module; the interception component divides the interception module into a first side and a second side, and the cycle comprises at least one of the following:
 a first metabolic cycle module, wherein an entrance and an exit of the pipeline are connected to the first side of the interception module, and the first metabolic cycle module has at least one inlet connected to the pipeline and at least one outlet connected to the second side of the interception module; and
 a second metabolic cycle module, wherein an entrance and an exit of the pipeline are connected to the second side of the interception module, and the second metabolic cycle module has at least one inlet connected to the first side and at least one outlet connected to the first side of the interception module.

29. The cycle treatment device according to claim 28, wherein the cycle module adjusts treatment efficiency of the cycle in at least one of the following ways:
 controlling the ratio of a total amount of the to-be-treated fluid introduced into the pipeline to a total amount of the fluid in the cycle per unit time; and
 controlling the ratio of a total amount of the treated fluid discharged from the pipeline to the total amount of the fluid in the cycle per unit time.

30. The cycle treatment device according to claim 28, wherein the cycle module further comprises a treatment unit, wherein the treatment unit controls the catalytic unit in at least one of the following ways:
 the treatment unit controls a type and total amount of the catalytic unit in the cycle by adding, supplementing, or replacing the catalytic unit;
 the treatment unit is configured to adjust activity of the catalytic unit in the cycle module.

31. The cycle treatment device according to claim 28, wherein the biocatalytic unit is selected from the group consisting of:
 a cell, a protein, an enzyme, a polypeptide, a nucleic acid, and
 a derivative, a complex, and an assembly in the form of a microsphere or microcapsule formed by at least one of the cell, protein, enzyme, polypeptide, and nucleic acid; and
 wherein the non-biocatalytic unit is selected from the group consisting of:
 a metal catalyst, and
 a derivative, a complex and an assembly in the form of a microsphere or microcapsule formed based on the metal catalyst.

32. The cycle treatment device according to claim 28, wherein the cycle module further comprises a channel-adjusting device, the channel-adjusting device is configured to regulate a flow direction of the fluid in the cycle to clean or replace the cyclic catalytic unit.

33. The cycle treatment device according to claim 28, wherein the interception component comprises a porous membrane or a reverse osmosis membrane, wherein the porous membrane is selected from the group consisting of a microfiltration membrane, an ultrafiltration membrane, and a nanofiltration membrane.

34. The cycle treatment device according to claim 28, wherein the interception component is selected from the group consisting of a planar membrane, a tubular membrane, a roll membrane, and a hollow fiber membrane.

35. The cycle treatment device according to claim 28, wherein in the first metabolic cycle module, the to-be-treated fluid is driven to the interception module by a driving device after being introduced into the cycle.

36. The cycle treatment device according to claim 35, wherein the preset flow rate is related to at least one of a structure of the catalytic unit, a composition of the fluid, a temperature of the fluid, a structure of the interception component, a material of the interception component, a cavity structure of the interception module, a diameter of the pipeline, and a fluid exchange efficiency.

37. The cycle treatment device according to claim 28, wherein an average pore diameter or molecular weight cutoff of the interception component is related to at least one of the catalytic unit, the target substance and the target product.

38. The cycle treatment device according to claim 28, wherein the cycle module is provided with a sampling device for adding reaction substrates, drugs, or catalytic units to the pipeline, or supplementing or replacing of the same.

39. The cycle treatment device according to claim 38, wherein the sampling device comprises at least one sample inlet connected to the pipeline, or the sampling device is a component allowing for injection of samples.

40. The cycle treatment device according to claim 28, wherein the cycle module is equipped with a collecting device, the collecting device has a collecting chamber for mixing the cyclic catalytic unit, the fluid margin, and the to-be-treated liquid to bring the catalytic unit into contact with the target substance.

41. The cycle treatment device according to claim 40, wherein the collecting device is further provided with at least one of a sample inlet, an air inlet-outlet, and a liquid outlet.

42. The cycle treatment device according to claim 28, wherein the cycle module comprises:
a pipeline, with an entrance and an exit;
a separation module, comprising a separation component that divides the separation module into a first side and a second side, wherein two opposite ends of the first side of the separation module are respectively connected to at least one inlet and at least one outlet, and two opposite ends of the second side of the separation module are respectively connected to the entrance and exit of the pipeline; and
at least one driving device, wherein the driving device is arranged in the pipeline to drive the fluid in the pipeline to flow from the entrance to the exit at a preset flow rate, so as to dynamically balance a total amount of the fluid in the pipeline under a separation cycle mode.

43. The cycle treatment device according to claim 42, wherein the fluid is introduced into N cycle modules for treatment, and the N cycle modules are connected in series or parallel with each other, wherein the N is a positive integer equal to or greater than 2.

44. The cycle treatment device according to claim 43, wherein the N cycle modules are connected in series with each other; according to the connection order, the average pore size or molecular weight cutoff of the separation component of each cyclic separation module decreases in sequence.

45. The cycle treatment device according to claim 42, wherein the separation component comprises a porous membrane or a reverse osmosis membrane, wherein the porous membrane is selected from the group consisting of a microfiltration membrane, an ultrafiltration membrane, and a nanofiltration membrane.

46. The cycle treatment device according to claim 42, wherein the separation component is selected from the group consisting of a planar membrane, a tubular membrane, a roll membrane, and a hollow fiber membrane.

47. The cycle treatment device according to claim 42, the preset flow rate is related to at least one of the target substance, a composition of the fluid, a temperature of the fluid, a structure of the separation component, a material of the separation component, a cavity structure of the separation module, a diameter of the pipeline, and a fluid exchange efficiency.

48. The cycle treatment device according to claim 28, wherein the cycle treatment device comprises N cycle modules, and different molecules or molecular combinations in the fluid are treated by the N treatment units corresponding to the N cycle modules, so that different components in the fluid are treated respectively in the N cycle modules; wherein the N is a positive integer equal to or greater than 2.

49. The cycle treatment device according to claim 28, wherein the cycle treatment device comprises N cycle modules, wherein the N cycle modules are connected in series, and specific molecules or molecular combinations in the fluid react continuously under the action of N treatment units corresponding to the N cycle modules; according to the connection order of the N cycle modules, intermediate products generated by the action of the treatment units in a previous cycle module are used as substrates to be treated in a subsequent cycle module, wherein the previous cycle module and the subsequent cycle module are two adjacent cycle module of the N cycle module connected in series; wherein the N is a positive integer equal to or greater than 2.

50. The cycle treatment device according to claim 28, wherein the fluid contains a target substance, the fluid is selected from the group consisting of blood, plasma, serum, body fluid, tissue fluid, cleaning fluid, dialysate, recombinant protein solution, cell culture medium, microbial culture medium, fluid food, animal and plant extract, natural water, industrial wastewater, and cycled water.

51. The cycle treatment device according to claim 28, wherein an inlet and an outlet of the cycle treatment device are connected to a same storage section, wherein the storage section comprises one or more of a storage device, a human body, and an animal body.

52. The cycle treatment device according to claim 28, wherein the cycle treatment device further comprises at least one treatment module, the treatment module is configured to perform pretreatment or retreatment on the fluid, wherein the pretreatment or retreatment is selected from the group consisting of a filtration treatment, an adsorption treatment, a heating treatment, a catalytic treatment, an enrichment treatment, a concentration treatment, an optical treatment, and an electrical treatment.

53. The cycle treatment device according to claim 28, wherein the cycle treatment device further comprises one device selected from the group consisting of a control device, a fluid storage device, a flow limiting device, a flow rate detection device, a pressure detection device, a temperature detection device, a temperature control device, an oxygen detection device, a bubble detection and elimination device, an alarm device, and a concentration detection device.

54. The cycle treatment device according to claim 53, wherein the control device generates information for adjusting an internal working state of the pipeline based on the flow rate detection device, or the pressure detection device, or the concentration detection device.

55. The cycle treatment device according to claim 28, wherein the cycle treatment device is configured to selectively remove or generate specific molecules or molecular combinations to control the molecular composition and molecular concentrations of the fluid, realizing disease treatment or health monitoring, wherein the diseases comprise one or more of familial hypercholesterolemia, hyperlipoproteinemia, autoimmune diseases, rapidly progressive glomerulonephritis, fatty liver, liver cirrhosis, acute liver failure, hyperlipidemia, severe acute pancreatitis, sepsis, Guillain-Barre syndrome, obesity, phenylketonuria, mucopolysaccharidosis, hypophosphatasia, hereditary hyperammonemia, hyperuricemia, gout, hyperglycemia, uroketosis, and diabetes.

56. A cycle treatment system, comprising:
- at least one cycle treatment device according to claim 28; and
- a pipeline system comprising a fluid-introducing pipeline and a fluid-returning pipeline.

57. The cycle treatment system according to claim 56, wherein the pipeline system further comprises at least one of an anticoagulation system, a control device, a fluid storage device, a pressure detection device, a temperature detection device, a temperature control device, an oxygen detection device, a bubble detection and elimination device, an alarm device, a flow limiting device, and a concentration detection device.

58. The cycle treatment system according to claim 56, wherein the cycle treatment system comprises an in-vitro cyclic metabolic system, wherein the fluid-introducing pipeline is configured to introduce a to-be-treated fluid from a body, and the fluid-returning pipeline is configured to return a treated fluid to the body, wherein the body is a human body or an animal body.

59. The cycle treatment system according to claim 56, wherein the to-be-treated fluid that is introduced from the body is treated by an enzyme or an enzyme-based product to selectively remove or generate specific molecules or molecular combinations in the fluid and to prevent the enzyme or enzyme-based product from entering the body, so as to control the molecular composition and molecular concentrations in body fluid of the human body or animal body.

60. A medical device, comprising a cycle treatment system according to claim 56.

61. The medical device according to claim 60 wherein the medical device is configured to selectively remove or generate specific molecules or molecular combinations to control the molecular composition and molecular concentrations of the fluid, so as to realize disease treatment or health monitoring, wherein the diseases comprise one or more of familial hypercholesterolemia, hyperlipoproteinemia, auto-immune diseases, rapidly progressive glomerulonephritis, fatty liver, liver cirrhosis, acute liver failure, hyperlipidemia, severe acute pancreatitis, sepsis, Guillain-Barre syndrome, obesity, phenylketonuria, mucopolysaccharidosis, hypophosphatasia, hereditary hyperammonemia, hyperuricemia, gout, hyperglycemia, uroketosis, and diabetes.

62. The medical device according to claim 60, wherein the fluid treatment method is used for disease treatment through combination with drugs.

63. A non-transitory computer-readable storage medium, wherein at least one program is stored on the computer-readable storage medium, and the fluid treatment method according to claim 1 is implemented when the at least one program is executed by a processor.

* * * * *